United States Patent
Seder et al.

(10) Patent No.: US 11,938,177 B2
(45) Date of Patent: *Mar. 26, 2024

(54) PEPTIDE VACCINE FORMULATIONS AND USE THEREOF FOR INDUCING AN IMMUNE RESPONSE

(71) Applicant: The United States of America, as represented by the Secretary, Department of Health and Human Services, Bethesda, MD (US)

(72) Inventors: Robert Seder, Chevy Chase, MD (US); Geoffrey Lynn, Bethesda, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 23 days.

This patent is subject to a terminal disclaimer.

(21) Appl. No.: 17/517,597

(22) Filed: Nov. 2, 2021

(65) Prior Publication Data
US 2022/0152170 A1    May 19, 2022

Related U.S. Application Data

(63) Continuation of application No. 16/079,972, filed as application No. PCT/US2017/019748 on Feb. 27, 2017, now Pat. No. 11,191,821.
(Continued)

(51) Int. Cl.
*A61K 39/00* (2006.01)
*A61K 9/00* (2006.01)
(Continued)

(52) U.S. Cl.
CPC ........ *A61K 39/0011* (2013.01); *A61K 9/0019* (2013.01); *A61K 39/001102* (2018.08);
(Continued)

(58) Field of Classification Search
None
See application file for complete search history.

(56) References Cited

U.S. PATENT DOCUMENTS

| | | |
|---|---|---|
| 2009/0081157 A1 | 3/2009 | Korbluth et al. |
| 2012/0141409 A1 | 6/2012 | Seymour et al. |
| | (Continued) | |

OTHER PUBLICATIONS

Li et al., Vaccines 2014, 2, 515-536 (Year: 2014).*
(Continued)

*Primary Examiner* — Karl J Puttlitz
(74) *Attorney, Agent, or Firm* — Klarquist Sparkman, LLP

(57) ABSTRACT

Embodiments of a novel platform for delivering a peptide antigen to a subject to induce an immune response to the peptide antigen are provided. For example, nanoparticle polyplexes are provided that comprise a polymer linked to a peptide conjugate by an electrostatic interaction. The conjugate comprises a peptide antigen linked to a peptide tag through an optional linker. An adjuvant may be included in the nanoparticle polyplex, linked to either the polymer or the conjugate, or admixed with the nanoparticles. The nanoparticle polyplex can be administered to a subject to induce an immune response to the peptide antigen.

27 Claims, 46 Drawing Sheets
Specification includes a Sequence Listing.

Related U.S. Application Data

(60) Provisional application No. 62/300,822, filed on Feb. 27, 2016.

(51) Int. Cl.
    *A61K 39/39*      (2006.01)
    *A61P 35/00*      (2006.01)
    *B82Y 5/00*      (2011.01)

(52) U.S. Cl.
    CPC .............. *A61K 39/39* (2013.01); *A61P 35/00* (2018.01); *A61K 2039/555* (2013.01); *A61K 2039/55555* (2013.01); *A61K 2039/60* (2013.01); *A61K 2039/6093* (2013.01); *B82Y 5/00* (2013.01)

(56) References Cited

U.S. PATENT DOCUMENTS

2014/0127253 A1    5/2014   Salem et al.
2017/0042995 A1    2/2017   Ali et al.

OTHER PUBLICATIONS

Handke et al., Colloids and Surfaces B: Biointerfaces 103 (2013) 298-303 (Year: 2013).*
Aichele, et al. "T cell priming versus T cell tolerance induced by synthetic peptides." *Journal of Experimental Medicine* 182, No. 1 (1995): 261-266.
Aranda, et al. "Trial Watch: Peptide vaccines in cancer therapy." *Oncoimmunology* 2, No. 12 (2013): e26621.
Barouch, et al. "International seroepidemiology of adenovirus serotypes 5, 26, 35, and 48 in pediatric and adult populations." *Vaccine* 29, No. 32 (2011): 5203-5209.
Bijker, et al. "Superior induction of anti-tumor CTL immunity by extended peptide vaccines involves prolonged, DC-focused antigen presentation." *European Journal of Immunology* 38, No. 4 (2008): 1033-1042.
Brito, et al. "Designing and building the next generation of improved vaccine adjuvants." *Journal of Controlled Release* 190 (2014): 563-579.
Calis, et al. "Properties of MHC class I presented peptides that enhance immunogenicity." *PLoS Computational Biology* 9, No. 10 (2013): e1003266.
Calvo et al., "Chitosan and Chitosan/Ethylene Oxide-Propylene Oxide Block Copolymer Nanoparticles as Novel Carriers for Proteins and Vaccines", *Pharmaceutical Research*, vol. 14, No. JO, 1997.
Castle, et al. "Exploiting the mutanome for tumor vaccination." *Cancer Research* (2012).
Chua et al., "Electrostatic-mediated enhancement of protein antigen immunogenicity using charged TLR2-targeting lipopeptides", *Procedia in Vaccinology* vol. 6 (2012) 80-84.
Coffman, et al. "Vaccine adjuvants: putting innate immunity to work." *Immunity* 33, No. 4 (2010): 492-503.
Den Boer, et al. "Longevity of antigen presentation and activation status of APC are decisive factors in the balance between CTL immunity versus tolerance." *The Journal of Immunology* 167, No. 5 (2001): 2522-2528.
Dubensky Jr, et al. "Adjuvants for cancer vaccines." In *Seminars in Immunology*, vol. 22, No. 3, pp. 155-161. Academic Press, 2010.
Hensley, et al. "Type I interferon inhibits antibody responses induced by a chimpanzee adenovirus vector." *Molecular Therapy* 15, No. 2 (2007): 393-403.
Hyde, et al. "CpG-free plasmids confer reduced inflammation and sustained pulmonary gene expression." *Nature Biotechnology* 26, No. 5 (2008): 549.
Jiang, et al. "DNA/PEI/Alginate polyplex as an efficientin vivo gene delivery system." *Biotechnology and Bioprocess Engineering* vol. 12, No. 6 (2007): 684-689.
Kenter, et al. "Vaccination against HPV-16 oncoproteins for vulvar intraepithelial neoplasia." *New England Journal of Medicine* 361, No. 19 (2009): 1838-1847.
Kreiter, et al. "Mutant MHC class II epitopes drive therapeutic immune responses to cancer." *Nature* 520, No. 7549 (2015): 692.
Linnemann, et al. "High-throughput epitope discovery reveals frequent recognition of neo-antigens by CD4+ T cells in human melanoma." *Nature Medicine* 21, No. 1 (2015): 81.
Liu, et al. "Structure-based programming of lymph-node targeting in molecular vaccines." *Nature* 507, No. 7493 (2014): 519.
Lynn, et al. "In vivo characterization of the physicochemical properties of polymer-linked TLR agonists that enhance vaccine immunogenicity." *Nature Biotechnology* 33, No. 11 (2015): 1201.
Melief, et al. "Immunotherapy of established (pre) malignant disease by synthetic long peptide vaccines." *Nature Reviews Cancer* 8, No. 5 (2008): 351.
Noguchi, et al. "A randomized phase II clinical trial of personalized peptide vaccination with metronomic low-dose cyclophosphamide in patients with metastatic castration-resistant prostate cancer." *Cancer Immunology*, Immunotherapy 65, No. 2 (2016): 151-160.
Perez, et al. "A new era in anticancer peptide vaccines." *Cancer* 116, No. 9 (2010): 2071-2080.
Petrizzo, et al. "Functional characterization of biodegradable nanoparticles as antigen delivery system." *Journal of Experimental & Clinical Cancer Research* 34, No. 1 (2015): 1.
Roberts, et al. "Hexon-chimaeric adenovirus serotype 5 vectors circumvent pre-existing anti-vector immunity." *Nature* 441, No. 7090 (2006): 239.
Rosalia, et al. "Dendritic cells process synthetic long peptides better than whole protein, improving antigen presentation and T-cell activation." *European Journal of Immunology* 43, No. 10 (2013): 2554-2565.
Rosario, et al. "Long peptides induce polyfunctional T cells against conserved regions of HIV-1 with superior breadth to single-gene vaccines in macaques." *European Journal of Immunology* 40, No. 7 (2010): 1973-1984.
Sabbatini, et al. "Phase I trial of overlapping long peptides from a tumor self-antigen and poly-ICLC shows rapid induction of integrated immune response in ovarian cancer patients." *Clinical cancer research* (2012): clincanres-2189.
Speetjens, et al. "Induction of p53-specific immunity by a p53 synthetic long peptide vaccine in patients treated for metastatic colorectal cancer." *Clinical Cancer Research* 15, No. 3 (2009): 1086-1095.
Toes, et al. "Peptide vaccination can lead to enhanced tumor growth through specific T-cell tolerance induction." *Proceedings of the National Academy of Sciences* 93, No. 15 (1996): 7855-7860.
Yadav, et al. "Predicting immunogenic tumour mutations by combining mass spectrometry and exome sequencing." *Nature* 515, No. 7528 (2014): 572.
Zhang, et al. "Comparing pooled peptides with intact protein for accessing cross-presentation pathways for protective CD8+ and CD4+ T cells." *Journal of Biological Chemistry* (2009).

\* cited by examiner

FIG. 1A
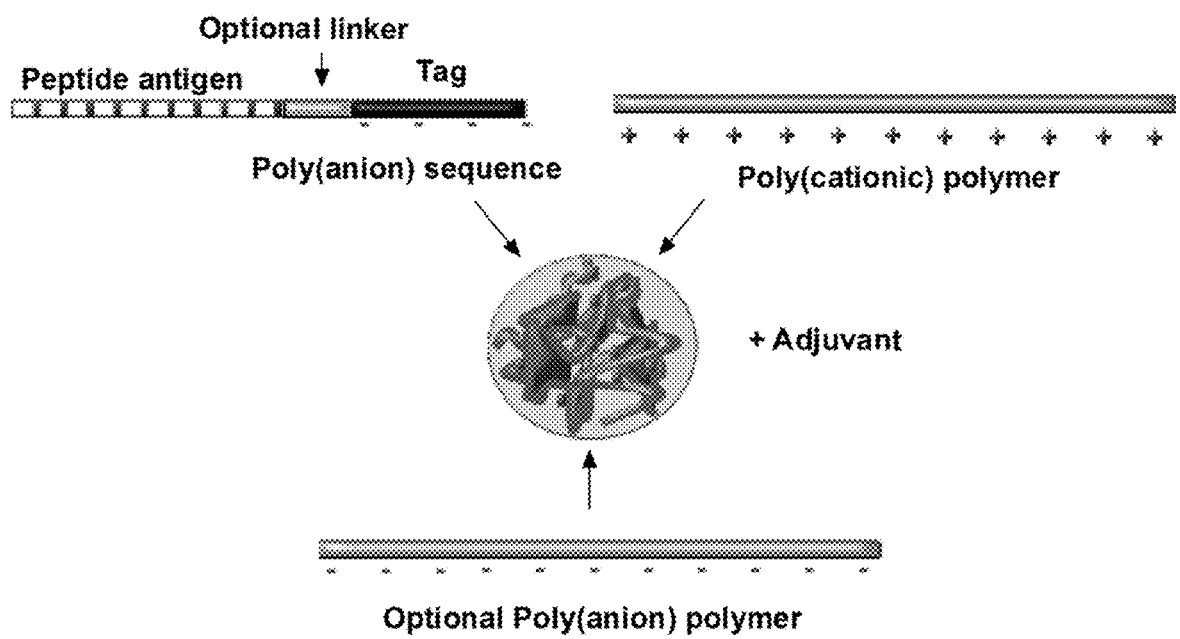
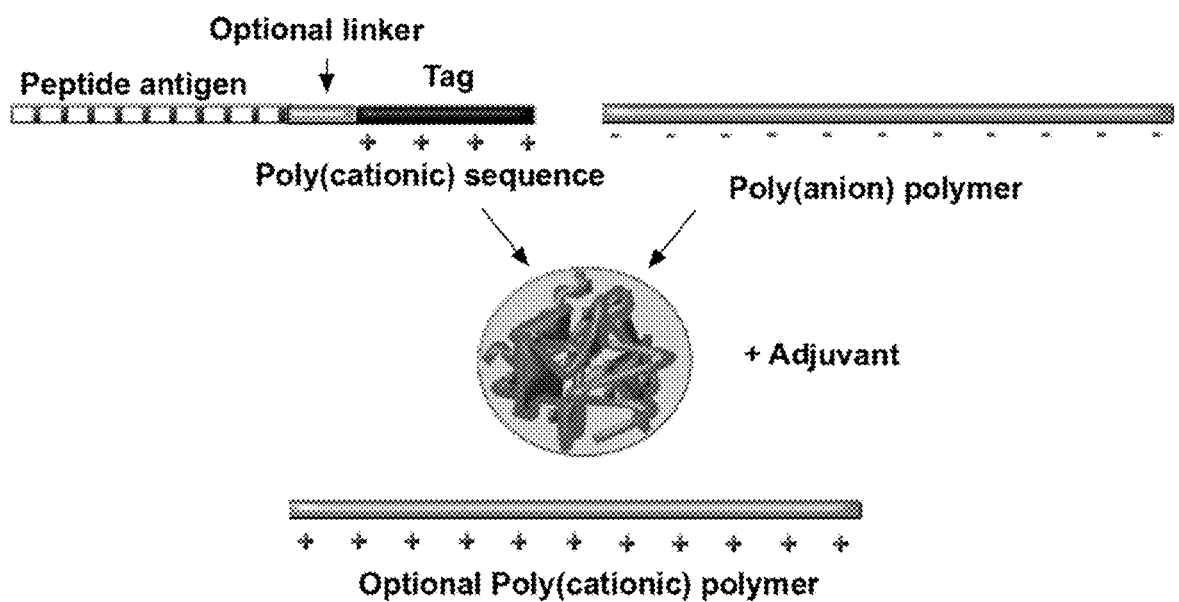

FIG. 2A

Long peptide SIINFEKL insoluble (LSI)

SIINFEKLVFPRSPTVFYNIPPMPLPPSQLK' (SEQ ID NO: 58)

Ser-Ile-Ile-Asn-Phe-Glu-Lys-Leu-Val-Phe-Pro-Arg-Ser-Pro-Thr-Val-Phe-Tyr-Asn-Ile-Pro-Pro-Met-Pro-Leu-Pro-Pro-Ser-Gln-Leu-Lys(N3) (SEQ ID NO: 58)

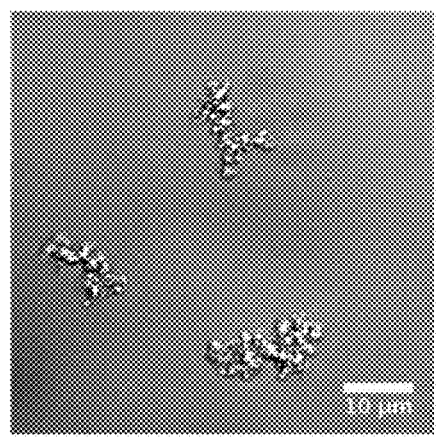

LSI (1)

Long peptide SIINFEKL insoluble-7/8a (LSI-7/8a)

SIINFEKLVFPRSPTVFYNIPPMPLPPSQLK'7/8a (SEQ ID NO: 58)

Ser-Ile-Ile-Asn-Phe-Glu-Lys-Leu-Val-Phe-Pro-Arg-Ser-Pro-Thr-Val-Phe-Tyr-Asn-Ile-Pro-Pro-Met-Pro-Leu-Pro-Pro-Ser-Gln-Leu-Lys(N3-DBCO-TLR-7/8a) (SEQ ID NO: 58)

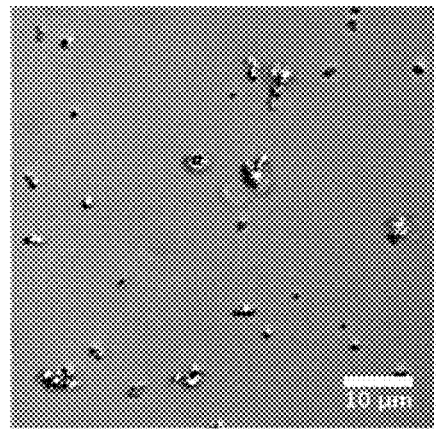

LSI-7/8a (2)

FIG. 2B

Long peptide SIINFEKL soluble (LSS)

SIINFEKLVKPRSPTRFDNSKPSPEPKSQDK* (SEQ ID NO: 59)

Ser-Ile-Ile-Asn-Phe-Glu-Lys-Leu-Val-Lys-Pro-Arg-Ser-Pro-Thr-Arg-
Phe-Asp-Asn-Ser-Lys-Pro-Ser-Pro-Glu-Pro-Lys-Ser-Gln-Asp-Lys(N3) (SEQ ID NO: 59)

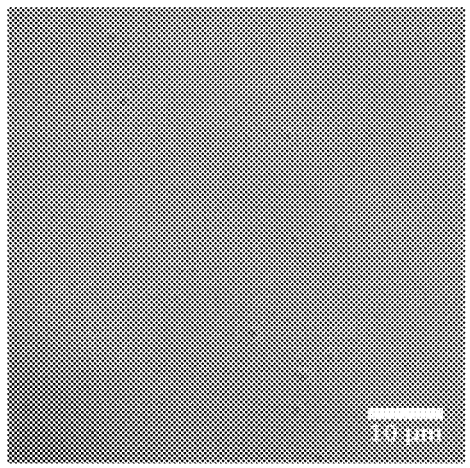

LSS (3)

Long peptide SIINFEKL soluble-7/8 (LSS-7/8a)

SIINFEKLVKPRSPTRFDNSKPSPEPKSQDK*-7/8a (SEQ ID NO: 59)

Ser-Ile-Ile-Asn-Phe-Glu-Lys-Leu-Val-Lys-Pro-Arg-Ser-Pro-Thr-Arg-
Phe-Asp-Asn-Ser-Lys-Pro-Ser-Pro-Glu-Pro-Lys-Ser-Gln-Asp-Lys(N3-
DBCO-TLR-7/8a) (SEQ ID NO: 59)

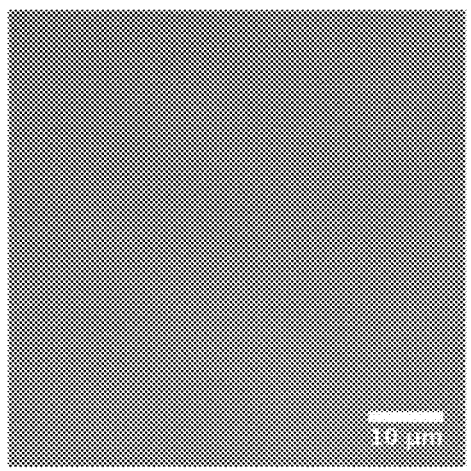
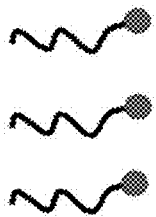

LSS-7/8a (4)

FIG. 2C
Small molecule TLR-7/8 agonist (2BXy)
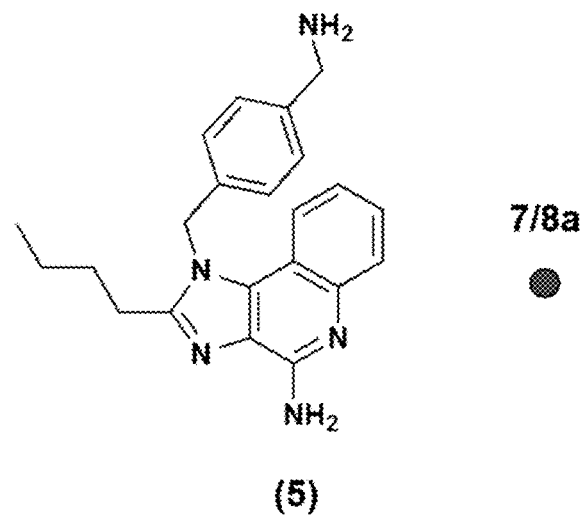
(5)
Particle-forming HPMA-based polymer-TLR-7/8a
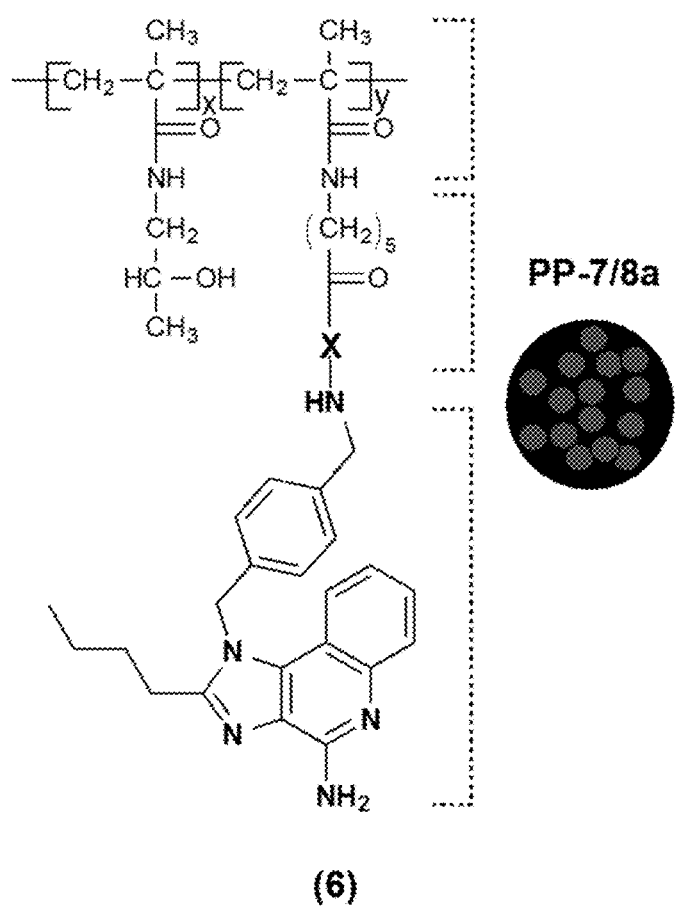
(6)

FIG. 4F
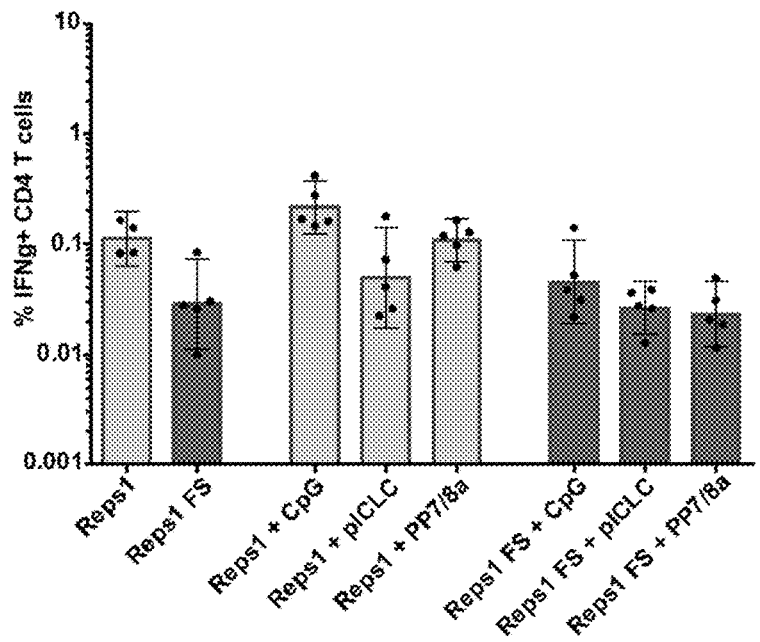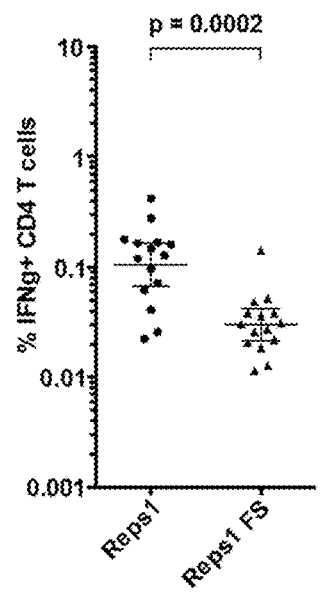
FIG. 4G
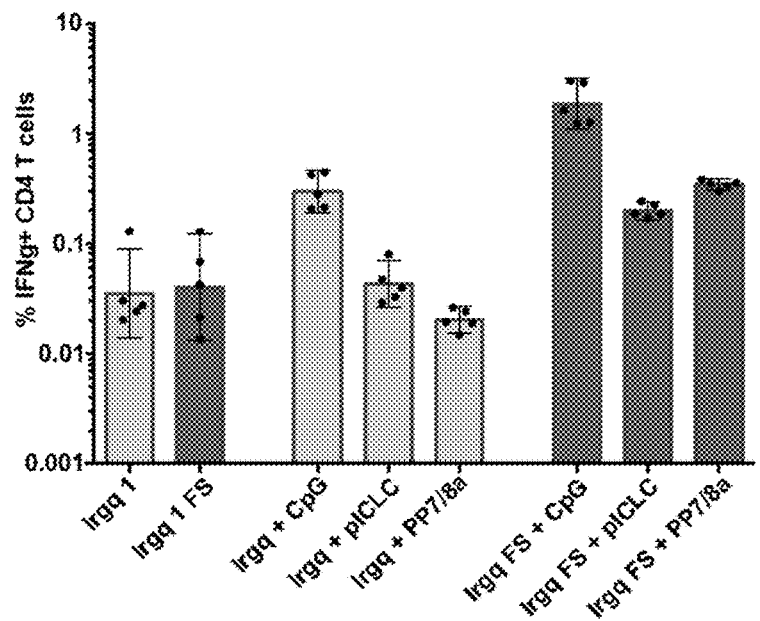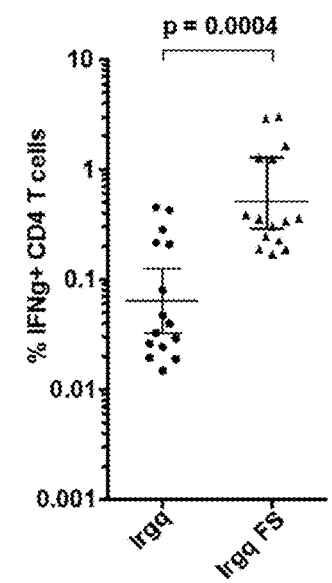

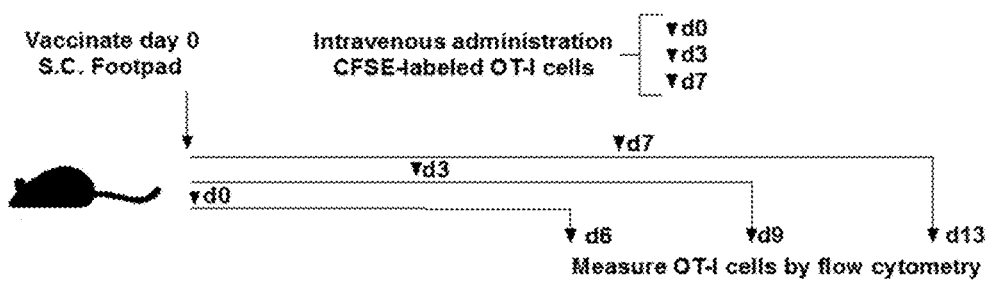
FIG. 5A
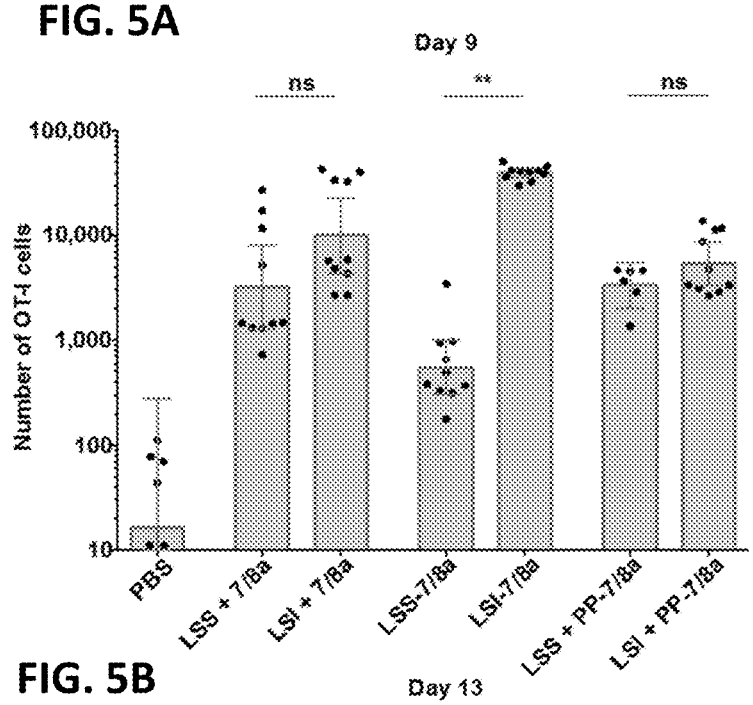
FIG. 5B
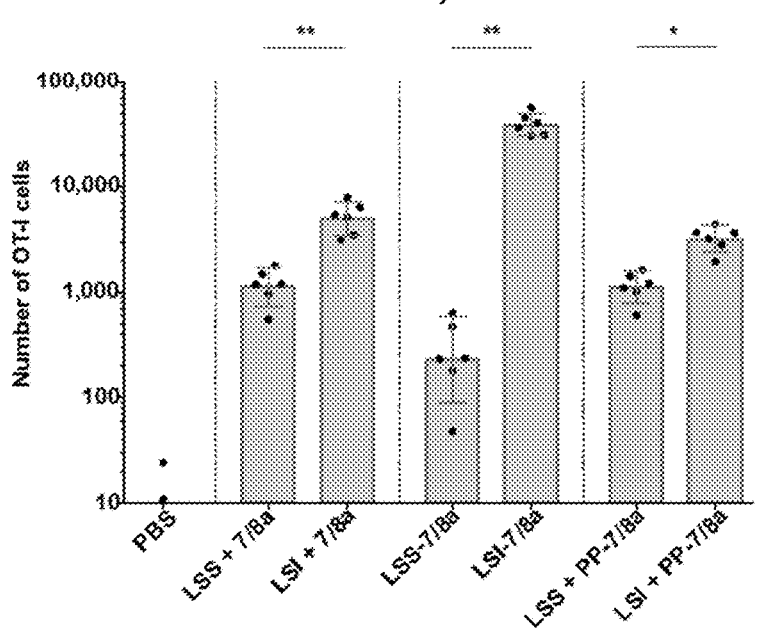

Linear poly(ethylenimine) (L-PEI) based carriers of TLR-7/8 agonists

Particle size of L-PEI 2.5%-PEG4-2BXy (27) complexed with alginate

Zeta potential of L-PEI 2.5%-PEG4-2BXy (27) conjugates complexed with alginate

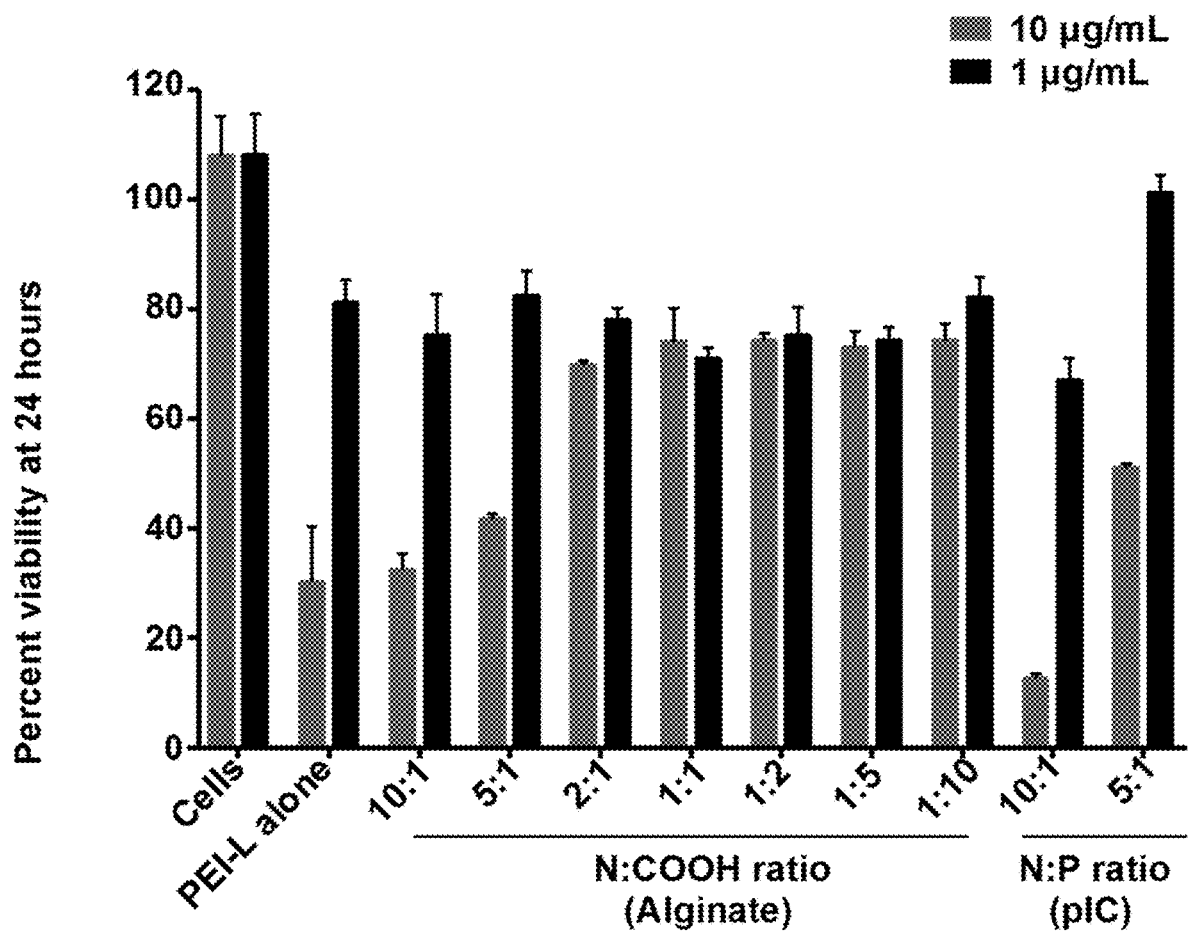

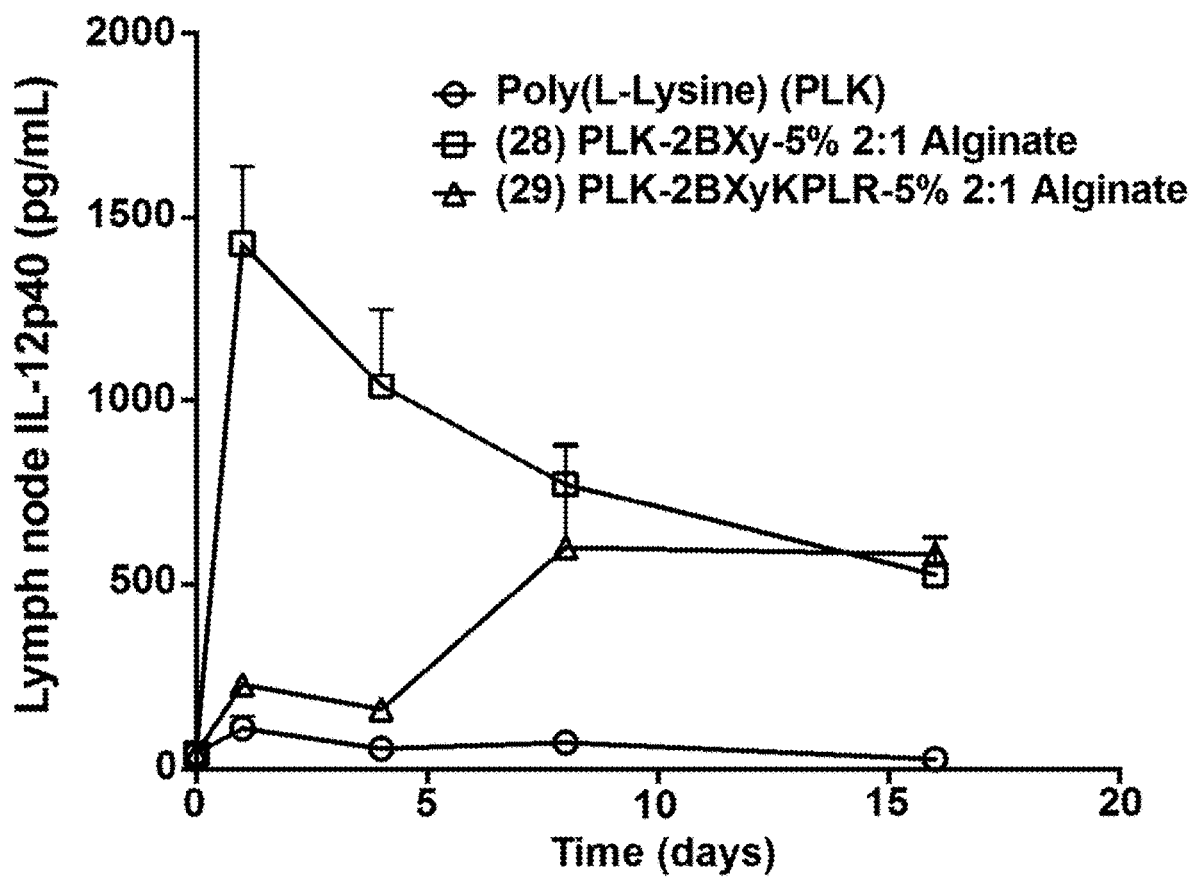

FIG. 14A

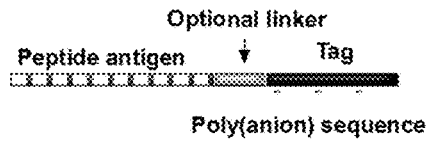

Reps1: Gly-Arg-Val-Leu-Glu-Leu-Phe-Arg-Ala-Ala-Gln-Leu-Ala-Asn-Asp-Val-Val-Leu-Gln-Ile-Met-Glu-Leu-Cys-Gly-Ala-Thr-Arg (SEQ ID NO: 60)

Reps1(E)5: Gly-Arg-Val-Leu-Glu-Leu-Phe-Arg-Ala-Ala-Gln-Leu-Ala-Asn-Asp-Val-Val-Leu-Gln-Ile-Met-Glu-Leu-Cys-Gly-Ala-Thr-Arg-Glu-Glu-Glu-Glu-Glu (SEQ ID NO: 29)

Reps1(E)10: Gly-Arg-Val-Leu-Glu-Leu-Phe-Arg-Ala-Ala-Gln-Leu-Ala-Asn-Asp-Val-Val-Leu-Gln-Ile-Met-Glu-Leu-Cys-Gly-Ala-Thr-Arg-Glu-Glu-Glu-Glu-Glu-Glu-Glu-Glu-Glu-Glu (SEQ ID NO: 30)

Reps1(E)15: Gly-Arg-Val-Leu-Glu-Leu-Phe-Arg-Ala-Ala-Gln-Leu-Ala-Asn-Asp-Val-Val-Leu-Gln-Ile-Met-Glu-Leu-Cys-Gly-Ala-Thr-Arg-Glu-Glu-Glu-Glu-Glu-Glu-Glu-Glu-Glu-Glu-Glu-Glu-Glu-Glu-Glu (SEQ ID NO: 31)

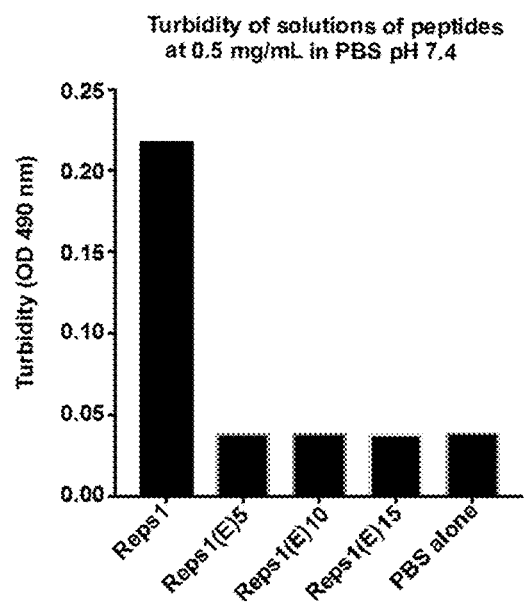

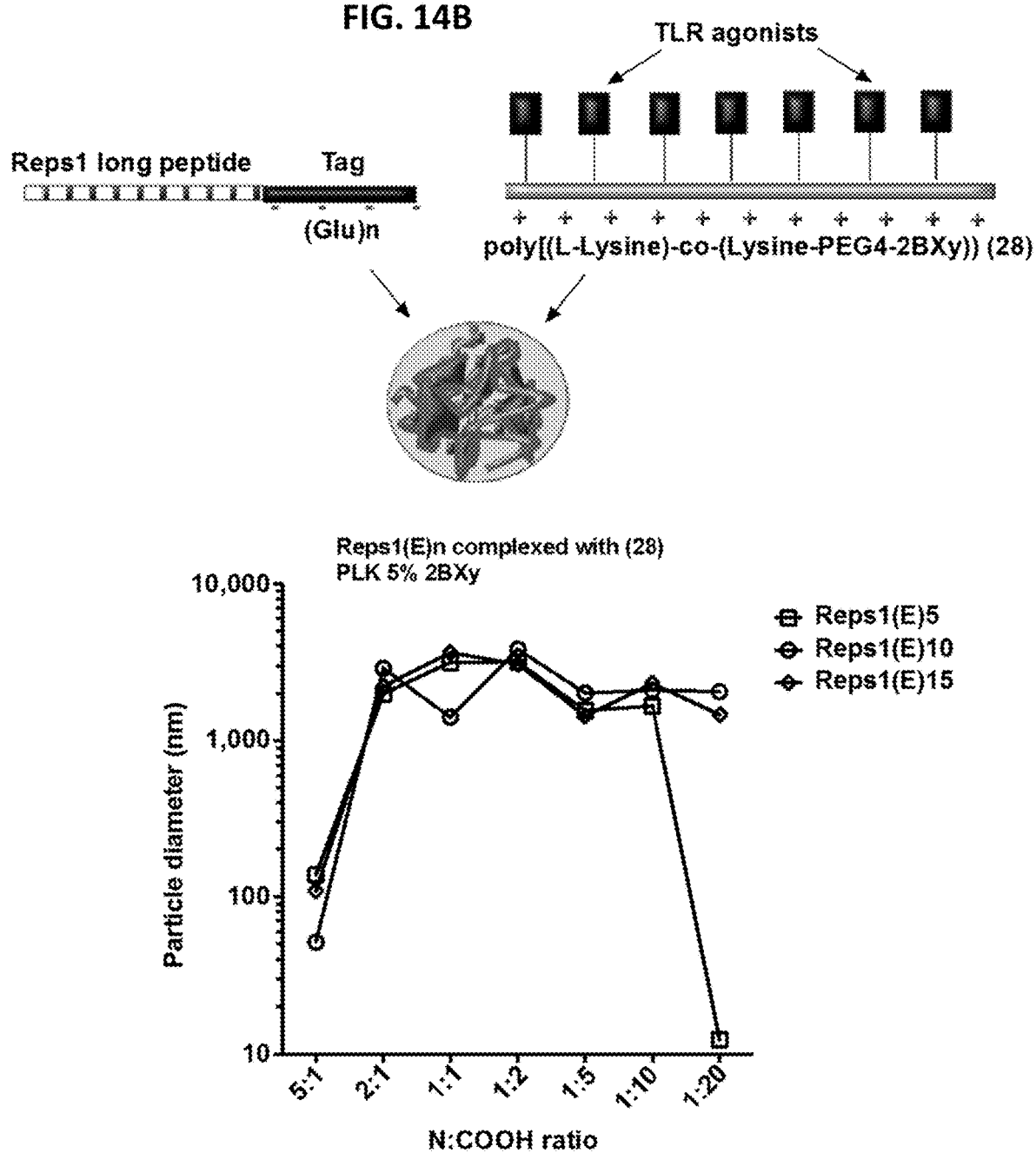

Adpgk R10 conjugate (55):

Minimal CTL epitope → Ala-Ser-Met-Thr-Asn-Met-Glu-Leu-Met-Ser- (SEQ ID NO: 49)
Linker → Ser-Leu-Val-Arg-Lys(N3-DBCO-PEG4-DBCO-
Tag → Arg-Arg-Arg-Arg-Arg-Arg-Arg-Arg-Arg-Arg) (SEQ ID NO: 3)

FIG. 14E
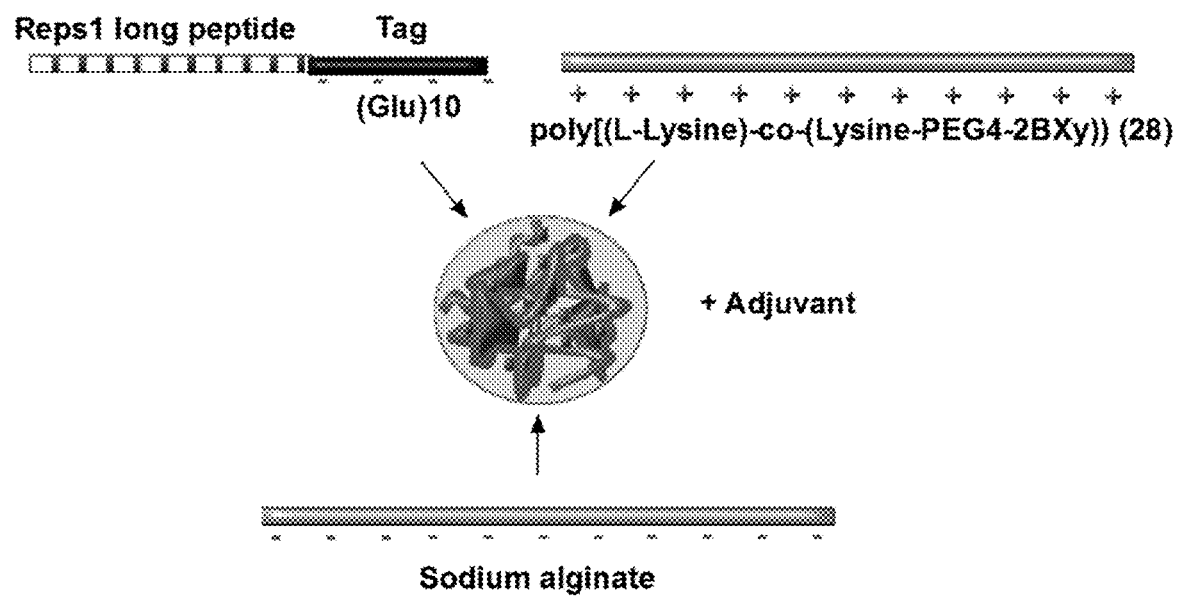
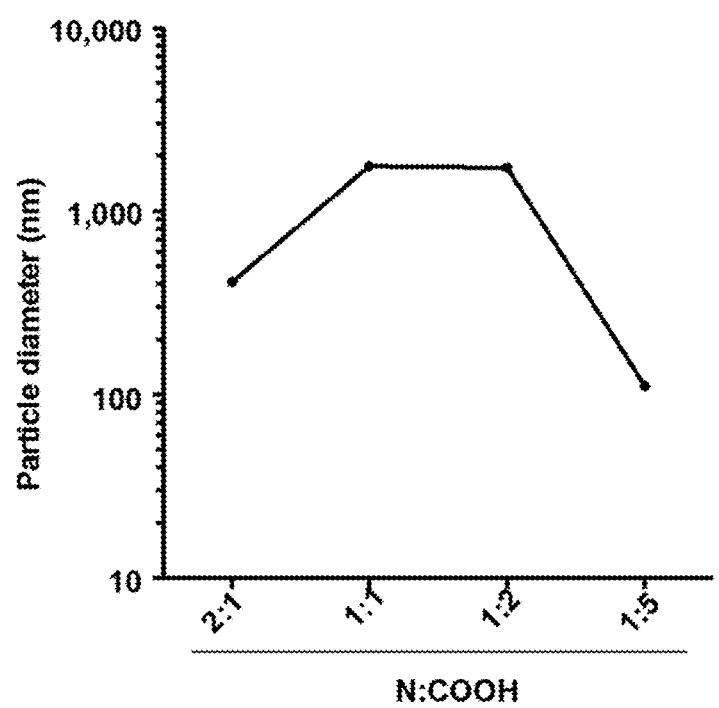

poly[(L-Lysine)-co-(Lysine-PEG4-2BXy)] (28)

(30) SIINFEKL-(E)10: Ser-Ile-Ile-Asn-Phe-Glu-Lys-Leu-Ser-Leu-Val-Arg-Glu-Glu-Glu-Glu-Glu-Glu-Glu-Glu-Glu-Glu (SEQ ID NO: 25)

(31) (E)10-SIINFEKL: Glu-Glu-Glu-Glu-Glu-Glu-Glu-Glu-Glu-Glu-Ser-Leu-Val-Arg-Ser-Ile-Ile-Asn-Phe-Glu-Lys-Leu (SEQ ID NO: 26)

(32) OT-II-(E)10): Ile-Ser-Gln-Ala-Val-His-Ala-Ala-His-Ala-Glu-Ile-Asn-Glu-Ala-Gly-Arg-Glu-Val-Val-Gly-Glu-Glu-Glu-Glu-Glu-Glu-Glu-Glu-Glu-Glu (SEQ ID NO: 27)

CD8: SIINFEKL(E)10 (30) (SEQ ID NO: 25)
N-CD8: (E)10SIINFEKL (31) (SEQ ID NO: 26)
CD4: ISQAVHAAHAEINEAGREVVG(E)10 (32) (SEQ ID NO: 27)

Polyplex(CD8): Poly(lysine) and (30) or (31)

Polyplex(CD8/CD4): Poly(lysine) and (32) and (30) or (31)

Polyplex(CD8/7/8a): PLK 5% PEG4-2BXy (28) and (30) or (31)

Polyplex(CD8/CD4/7/8a): (28) and (32) and (30) or (31)

FIG. 15C
Stratified by charge ratio
FIG. 15D
Stratified by linkage site
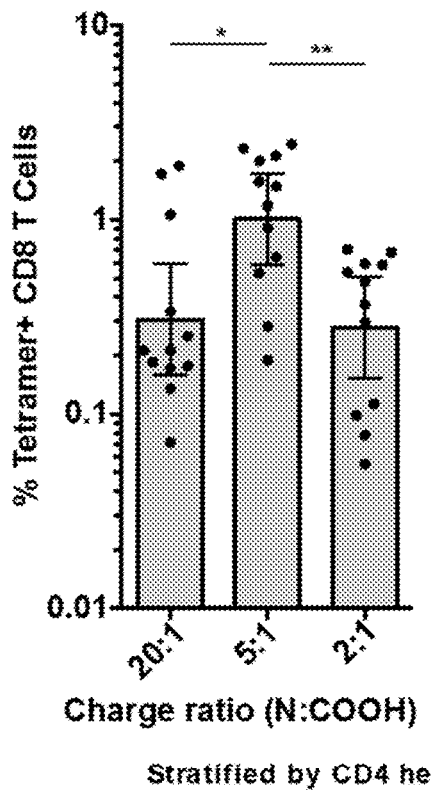
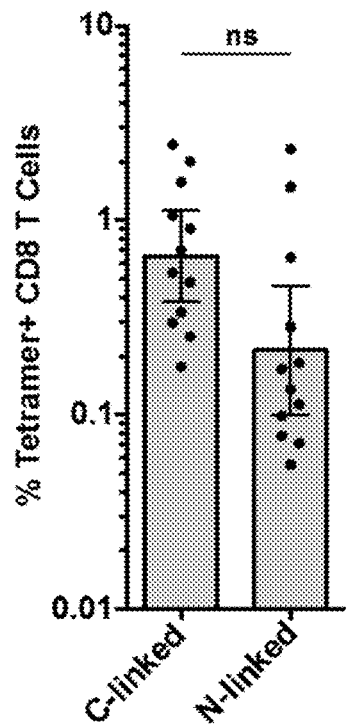
Stratified by CD4 help
FIG. 15E
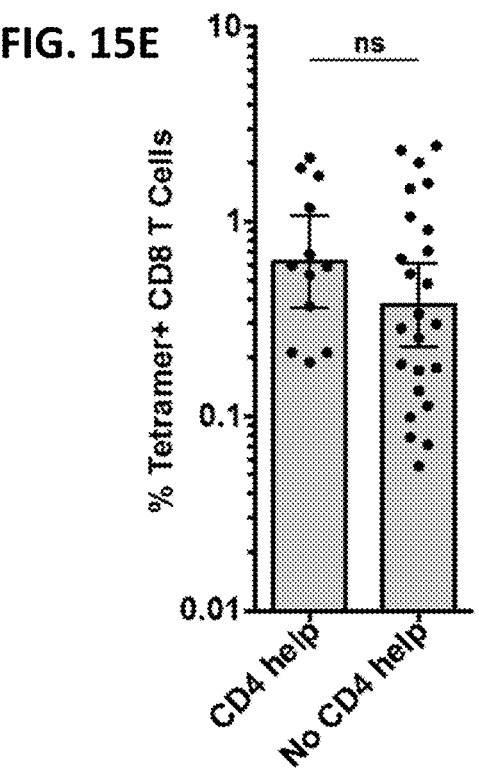

CD8: SIINFEKL(E)10 (30) (SEQ ID NO: 25)
CD4: ISQAVHAAHAEINEAGREVVG(E)10 (32) (SEQ ID NO: 27)

Polyplex(CD8): Poly(lysine) and (30)

Polyplex(CD8/CD4): Poly(lysine) and (32) and (30)

Polyplex(CD8/7/8a): PLK 5% PEG4-2BXy (28) and (30)

Polyplex(CD8/CD4/7/8a): (28) and (32) and (30)

Charge ratio 5:1 (N:COOH)

LSI-7/8a (2)

PP-7/8a (6)

Days post tumor implantation

Polyplex(CD8/CD4/7/8a):
PLK 5% PEG4-2BXy (28) complexed with and (32) and (30) at a 5:1 (N:COOH) charge ratio Days after tumor implantation

(32) OT-II-(E)10: Ile-Ser-Gln-Ala-Val-His-Ala-Ala-His-Ala-Glu-Ile-Asn-Glu-Ala-Gly-Arg-Glu-Val-Val-Gly-Glu-Glu-Glu-Glu-Glu-Glu-Glu-Glu-Glu-Glu(SEQ ID NO: 27)

(33) Irgq(E)10: Ala-Ala-Leu-Leu-Asn-Ser-Ala-Val-Leu-Gly-Gly-Ala-Pro-Glu-Glu-Glu-Glu-Glu-Glu-Glu-Glu-Glu-Glu(SEQ ID NO: 28)

Polyplex(Irgq(E)10): Poly(lysine) and (33)

Polyplex(Irgq(E)10/7/8): PLK 5% PEG4-2BXy (28) and (33)

Polyplex(Irgq(E)10/CD4/7/8a): (28) and (33) and (32)

PP-7/8a (6)

Charge ratio 5:1 (N:COOH)

Polyplex(Irgq(E)10): Poly(lysine) and (33)

Polyplex(Irgq(E)10/7/8): PLK 5% PEG4-2BXy (28) and (33)

Polyplex(Irgq(E)10/CD4/7/8a): (28) and (33) and (32)

PP-7/8a (6)

Charge ratio 5:1 (N:COOH)

FIG. 21C
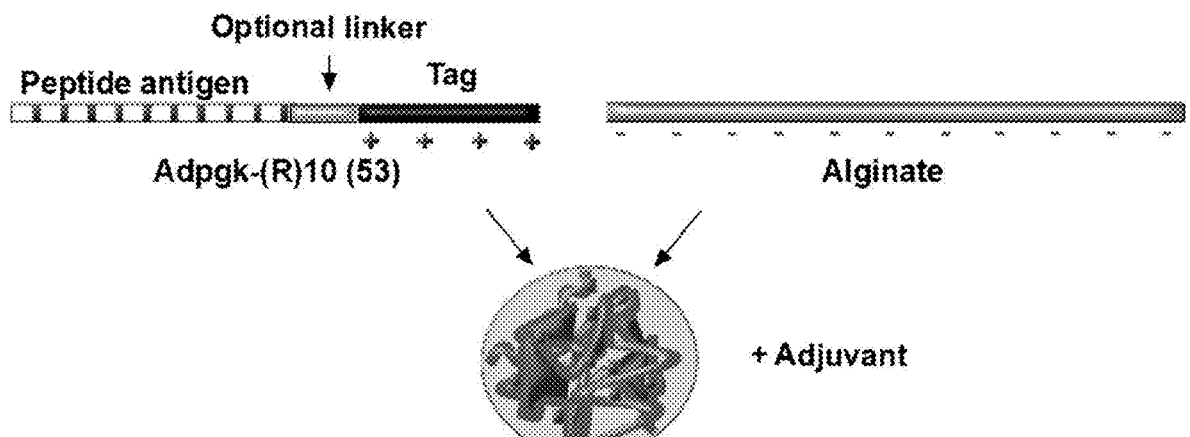
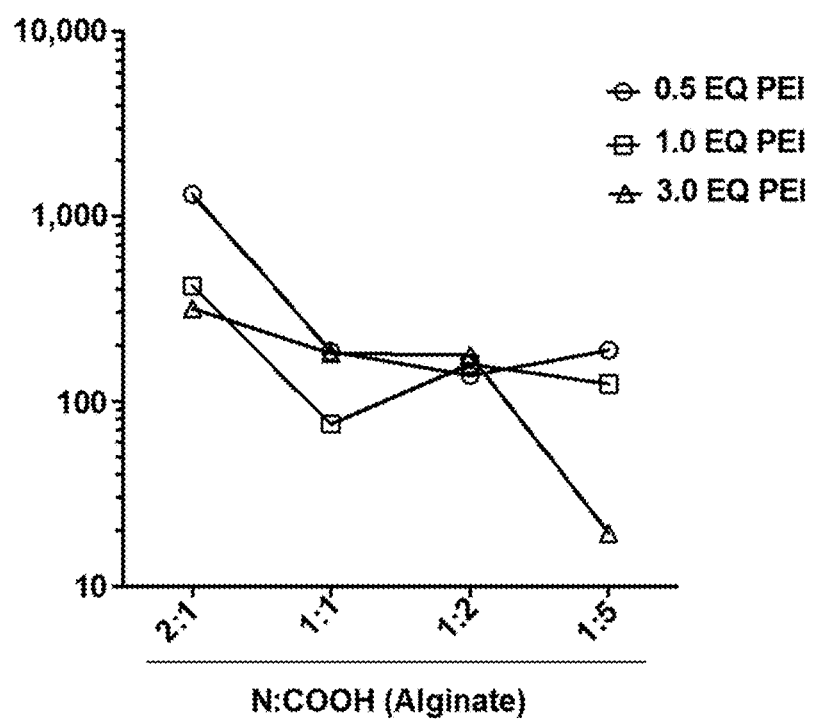

PEPTIDE VACCINE FORMULATIONS AND USE THEREOF FOR INDUCING AN IMMUNE RESPONSE

CROSS REFERENCE TO RELATED APPLICATIONS

This is a continuation of U.S. application Ser. No. 16/079,972, filed Aug. 24, 2018, which is the U.S. National Stage of International Application No. PCT/US2017/019748, filed Feb. 27, 2017, which claims the benefit of U.S. Provisional Application No. 62/300,822, filed Feb. 27, 2016. The prior applications are incorporated herein by reference in their entirety.

FIELD OF THE DISCLOSURE

This disclosure relates to embodiments of a novel platform for delivering a peptide antigen to a subject to induce an immune response to the antigen.

BACKGROUND

Generating tumor specific T cells directed against a specific type of cancer cell requires identification of antigens that are expressed by the cancer cells and are recognized by patient's own T cells. These so-called tumor-associated antigens can either be self-antigens that are expressed by both normal cells and cancer cells, or neoantigens, which are mutated self-antigens that are only present on the cancer cells. Until recently, the majority of cancer vaccine strategies have used tumor-associated self-antigens to generate cancer-specific T cell responses. While adoptive transfer of tumor specific lymphocytes against self-antigens can be effective, these approaches can also result in significant toxicity and morbidity due to immune activation against normal cells expressing self-antigen. As an alternative to self-antigens, recent advances in DNA and RNA sequencing technologies, as well as mass spectrometry, have been used to identify tumor-specific neoantigens from patient tumor samples. Based on these unique antigens, predictive algorithms are then applied to determine which sequences of the neoantigens have the potential to be immunogenic in the context of the patient's own histocompatibility loci. Such tumor specific neoantigens can then be formulated as a subunit vaccine and given to patients to generate lymphocyte responses against these neoantigens. Data show that individual patients have unique set of neoantigens that are distinct to their tumors; however some neoantigens arise from so-called hot-spot mutations and may be shared between patients. Thus, commercial development of an immunization protocol targeting tumor neoantigens may require an individualized vaccine approach that is relatively rapid, safe and scalable for broad application.

Tumor neoantigens can be given as a subunit vaccine to patients using either a peptide or gene delivery platform. Peptide-based vaccines are chemically well defined and can be produced rapidly using solid-phase peptide synthesis. The disadvantage of peptide-based vaccines is that the broad physical and chemical diversity of peptide sequences makes formulation strategies unpredictable and responses variable depending on the pharmacokinetic properties of the peptide.

SUMMARY

Disclosed herein are embodiments of novel immunogenic compositions for delivering a peptide antigen to a subject to induce an immune response to the peptide antigen. The disclosed immunogenic compositions, as well as methods of their use, overcome prior difficulties of inducing an effective immune response to peptide antigens in a subject, particularly with regard to soluble peptide antigens.

In some embodiments, the immunogenic composition comprises polymer nanoparticles that comprise a polymer linked to a conjugate by an electrostatic interaction. The conjugate comprises a peptide antigen linked to a peptide tag, optionally via a linker. An adjuvant is included in the nanoparticles, and may be linked to either the polymer or the conjugate, or the adjuvant may be admixed separately into the nanoparticles. In some embodiments, the polymer is an adjuvant, such as a negatively charged nucleic acid sequence, e.g., CpG. The peptide tag comprises a net electrostatic charge opposite that of the polymer. Charge neutralization between the peptide tag and polymer of opposite charge results in formation of polymer nanoparticles including a complex of peptide antigen and polymer, referred to as polyplexes. The polymer nanoparticles can enter immune cells under physiological conditions to induce the immune response to the peptide antigen in the subject.

In several embodiments, the peptide antigen is a soluble peptide antigen; for example, a peptide consisting of the peptide antigen can dissolve to at least 0.1 mg/mL in phosphate buffered saline, pH 7.4 at room temperature. In some embodiments, the peptide tag can be C-terminal to the peptide antigen in the conjugate. In some embodiments, one or more aromatic amino acids (such as tryptophan) can be included on the peptide tag or the polymer to increase stability of the polyplexes through Van der Waals (hydrophobic) interactions or Pi orbital stacking.

Methods for inducing an immune response to a peptide antigen are also provided, the method including administering an effective amount of a disclosed immunogenic composition to the subject to induce the immune response.

The foregoing and other features and advantages of this disclosure will become more apparent from the following detailed description of several embodiments, which proceeds with reference to the accompanying figures.

BRIEF DESCRIPTION OF THE FIGURES

FIGS. 1A-1D: Schematics of the nanoparticle polyplexes disclosed herein. (1A) Peptide antigen conjugates comprised of peptide antigens linked to peptide tags of net negative or positive charge that are complexed with polymers through electrostatic interactions to form polymer complexes, or polyplexes. (1B) Peptide antigen conjugates comprised of peptide antigens linked to peptide tags of net negative charge that are complexed with poly(cationic) polymer carriers of TLR agonists. (1C) Peptide antigen conjugates comprised of peptide antigens linked to peptide tags of net positive charge that are complexed with poly(anionic) polymer carriers of TLR agonists. (1D) Peptide antigen conjugates that are linked to peptide tags of either or both positive and negative charge that assemble into polyplexes.

FIGS. 2A-2E: Impact of adjuvant and the composition of amino acids flanking minimal epitopes on CD8 T cell responses induced by synthetic long peptide vaccines. (2A and 2B) Synthetic long peptides delivering the minimal CTL epitope from Ovalbumin (OVA$_{257-264}$: SIINFEKL, SEQ ID NO: 1) were prepared with either hydrophobic or hydrophilic flanking sequences to provide insoluble (LSI, 1) or soluble (LSS, 3) peptides alone or linked to a TLR-7/8a through a C-terminal azide to yield a LSI-7/8a (2) and LSS-7/8a (4). Bright field microscopy images are shown of peptides 3-6 at 0.1 mg/mL in PBS at pH 7.4. (2C) The TLR-7/8a adjuvant was delivered as either a small molecule (7/8a, 5) or as a particle (PP-7/8a, 6) with the peptide antigens. (2D and 2E) Long peptides (4 nmol) alone or admixed with or covalently attached to adjuvant (4 nmol) were subcutaneously administered into the hind footpads of mice at days 0 and 14. At day 28, tetramer+ CD8 T cell responses were evaluated from whole blood of mice (n=5-25).

FIGS. 4A-4G: Influence of neoantigen flanking sequences on long peptide morphology and CD8 T cell immunity. (4A) The sequences flanking two minimal CD8 T cell neoantigen epitopes, Reps1 (7) and Irgq (9), derived from murine MC38 melanoma were exchanged to create two chimeric synthetic long peptides, Reps1 FS (8) and Irgq FS (10). Bright field microscopy images are shown for peptides 7-10 at 0.1 mg/mL in PBS at pH 7.4. (4B-4G) The synthetic long peptide-based neoantigens (7-10) (4 nmol) were admixed with adjuvant (4 nmol) and subcutaneously administered into the hind footpads of C57BL/6 mice at days 0 and 14 and on day 28 whole blood was assessed for the percent of total CD8 T cells that were dextramer$^+$ for Reps1 (4B) and Irgq (4C); the percent of total CD8 T cells that were IFNγ following stimulation with either Reps1 (4D) or Irgq (4E); or, the percent of total CD4 T cells that were IFNγ following stimulation with either Reps1 (4F) or Irgq (4G). Data on log scale are reported as geometric mean with 95% confidence interval (CI). Data are representative of two or more independent experiments. Student's T test was used for comparison of 2 groups; ns, not significant (P>0.05); *, P<0.05; **, P<0.01.

FIGS. 5A-5B: Long peptide aggregation increases the persistence of antigen presentation in vivo. (AandB) Synthetic long peptides (4 nmol) delivering the minimal CTL epitope from Ovalbumin ($OVA_{257-264}$: SIINFEKL, SEQ ID NO: 1) covalently admixed with or covalently linked to adjuvant (4 nmol) were subcutaneously administered to mice at day 0. CFSE-labeled OT-I cells were transferred to mice at either day 3 or at day 7 following vaccination and both the number of OT-I cells and percent of fully divided cells were assessed from whole blood 6 days after transfer, days 9 (5A) and 13 (5B). Individual groups of data are reported as median and grouped data are presented as geometric mean with 95% confidence interval (CI). Data are representative of two or more independent experiments. Student's T test was used for comparison of 2 groups; ns, not significant (P>0.05); *, P<0.05; **, P<0.01.

FIG. 9: Impact of charge ratio on the cytotoxicity of nanoparticle polyplexes. Linear PEI was complexed with either sodium alginate or the nucleic acid, poly(I:C) at different charge ratios and then incubated with HEK293. Viability of the HEK293 cells was assessed 24 hours after incubation.

FIGS. 13A-13B: In vivo activity of poly(L-lysine) (PLK)-based carriers of TLR-7/8a. (13A) Structure of a PLK-based carrier of TLR-7/8a. (13B) Mice were administered either compound (28) or compound (29) (normalized for Molarity of the TLR-7/8a, 50 μM) complexed with sodium alginate at a charge ratio of 2:1 delivered in 50 μL volume of PBS pH 7.4 solution given into both hind footpads at day 0. Lymph nodes draining the site of immunization were isolated at serial timepoints thereafter and then assessed for IL-12 (13B) by ELISA.

FIGS. 14A-14E: Impact of the tag sequence on the solubility of peptide antigen conjugates and complexation with different cationic polymers. (14A) The native Reps1 antigen, or peptide antigen conjugates comprised of the Reps1 antigen linked to peptide tags comprised of different lengths of glutamic acids, (Glu)$_5$ (residues 1-5 of SEQ ID NO: 23), (Glu)$_{10}$ (residues 1-10 of SEQ ID NO: 23), (Glu)$_{15}$ (SEQ ID NO: 23) were assessed for aqueous solubility by measuring absorbance at 490 nm (turbidity). (14B-14E) Dynamic light scattering was used to assess the particle sizes of the polyplexes formed by complexing the Resp1-(Glu)$_n$ peptide antigen conjugates with different poly(cationic) polymers over a range of charge ratios.

FIGS. 15A-15E: Optimization of peptide antigens in nanoparticle polyplexes to induce CD8 T cell immunity. (15A) Schematic representation of a generalizable approach for linking minimal CD8 and CD4 epitopes to polymer-TLR-7/8a conjugates that assemble into particles through electrostatic interactions. Synthetic long peptides were prepared with CD8 and CD4 epitopes fused to linker sequences comprised of 10 glutamic acid residues that are negatively charged at physiologic pH (7.4). The CD8 and CD4 epitopes with poly(glutamic acid) linkers electrostatically complex poly(L-lysine) (PLK)-based copolymer conjugates of TLR-7/8a (PLK-7/8a) to form nanoparticle electrostatic polymer complexes, referred to as polyplexes. Polyplexes formed using different charge ratios (15B), antigen-linkage sites (N-terminal versus C-terminal) (15C) and co-delivered CD4 T helper epitopes (15D) were assessed for their impact on tetramer+ CD8 T cell responses measured from whole blood at day 14 following immunizations at day 0 and 7.

Figure 16A:
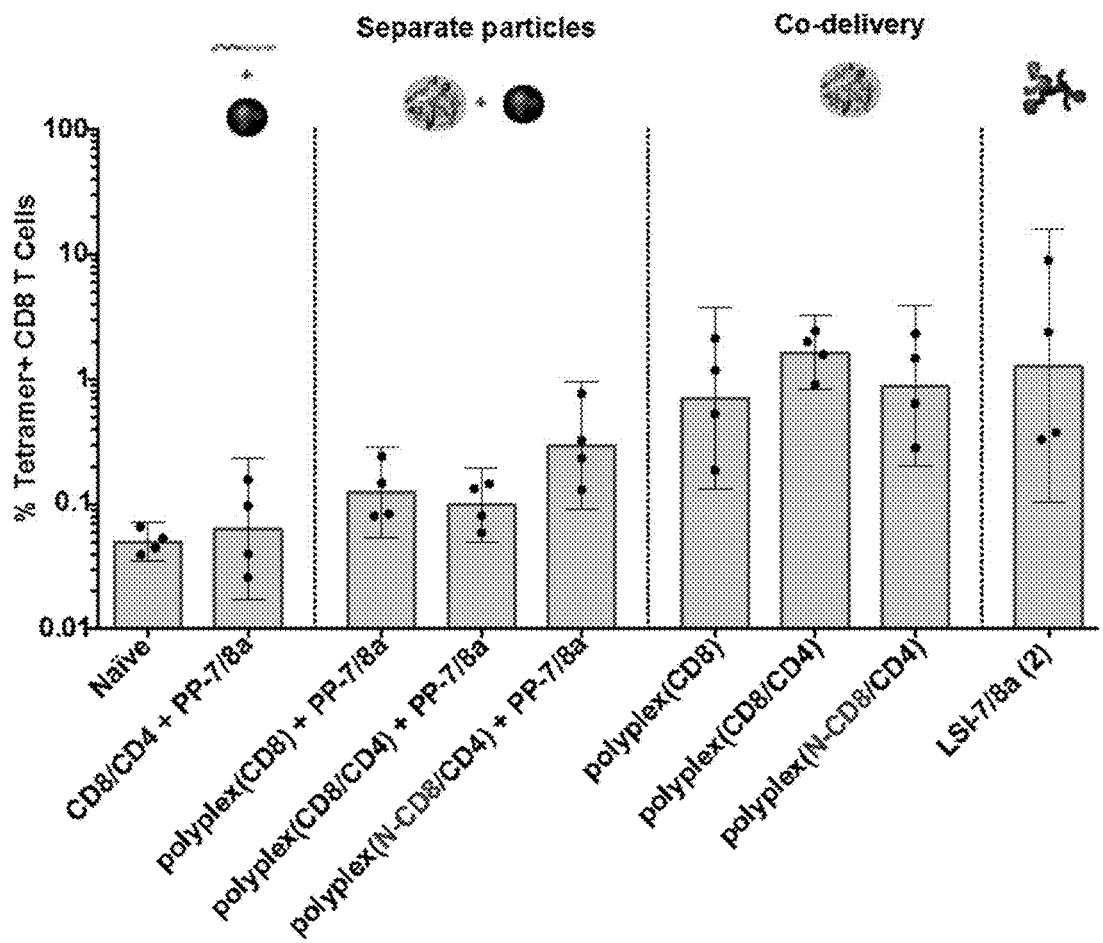
Figure 16B:
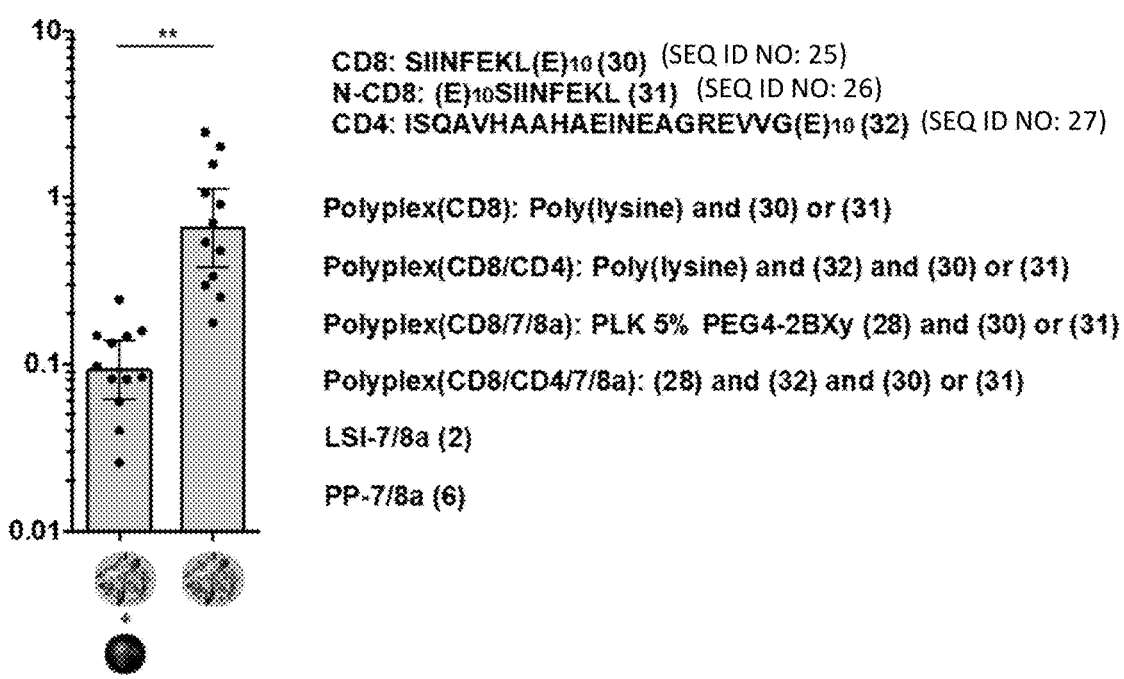

FIGS. 16A-16B: Co-delivery of TLR-7/8a with peptide antigens in polyplexes increases magnitude of CD8 T cells responses. (16A and 16B) Mice were immunized with polyplexes delivering antigen alone admixed with particulate TLR-7/8a or with polyplexes co-delivering TLR-7/8a and mice were bled 2 weeks following 2 immunizations and were assessed for % tetramer positive of total CD8 T cells. Data on log scale are reported as geometric mean with 95% confidence interval (CI). Student's T test was used for comparison of 2 groups; comparison of multiple groups for statistical significance was determined using one-way ANOVA with Bonferroni correction; ns, not significant (P>0.05); *, P<0.05; **, P<0.01.

Figure 17:
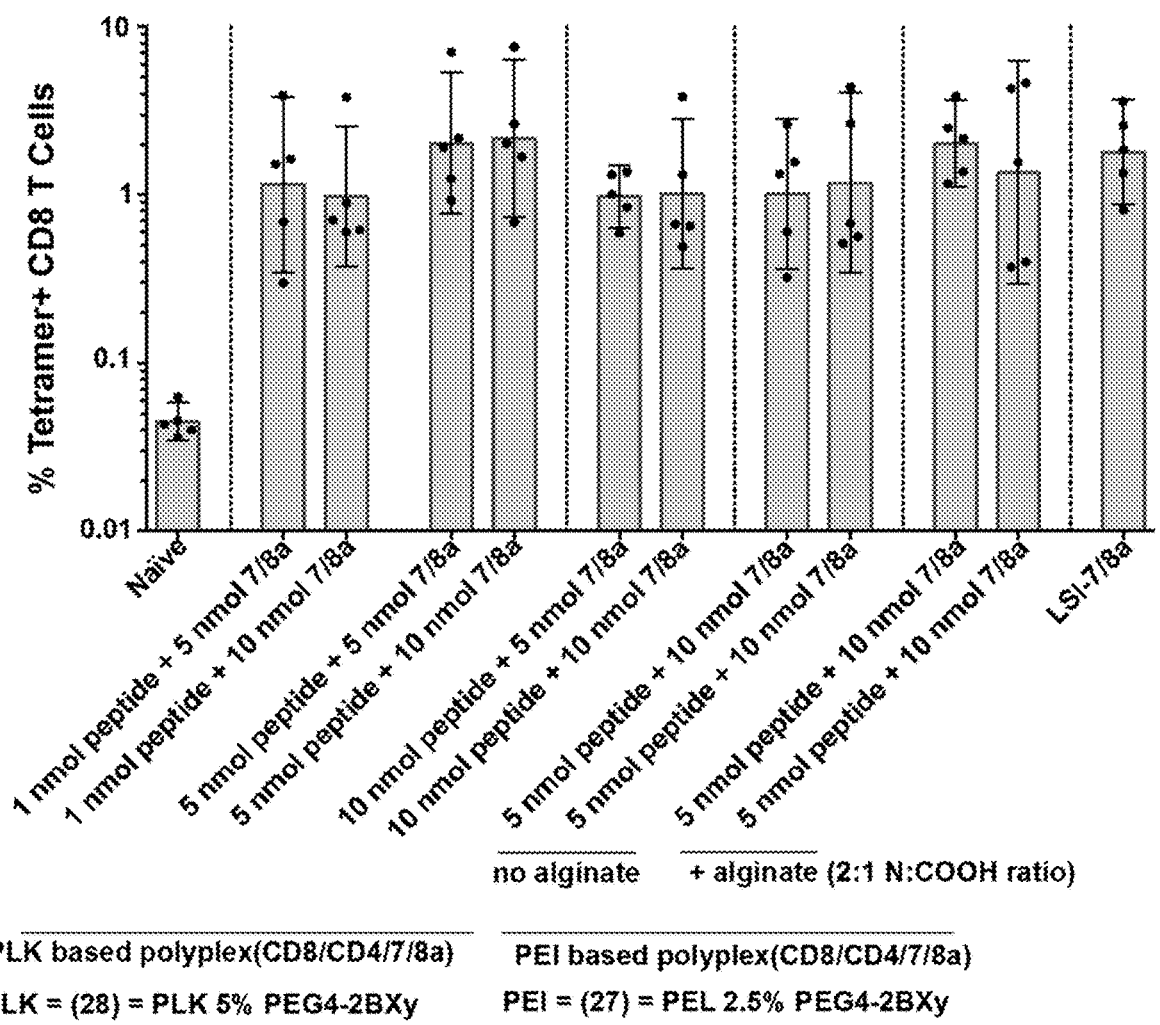
Figure 18A:
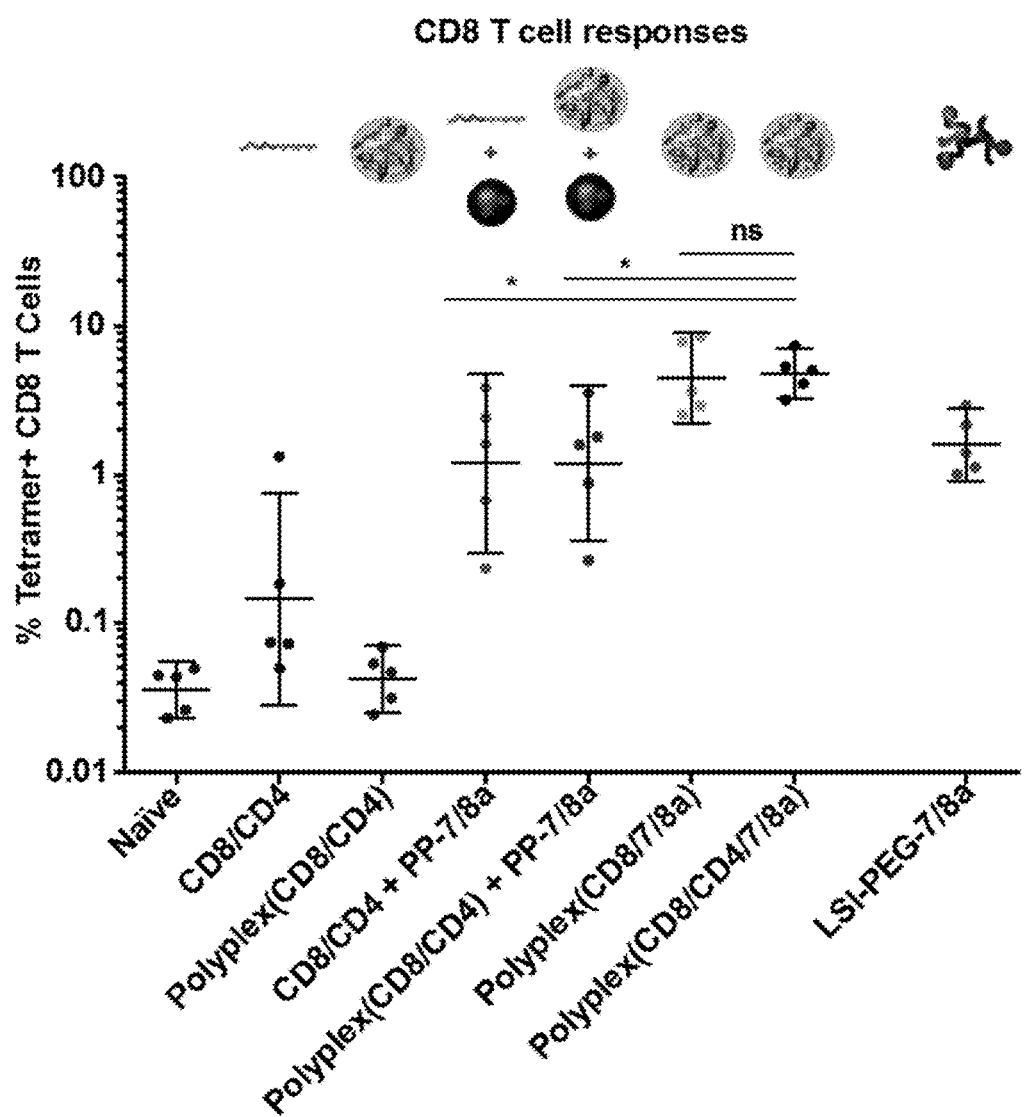
Figure 18B:
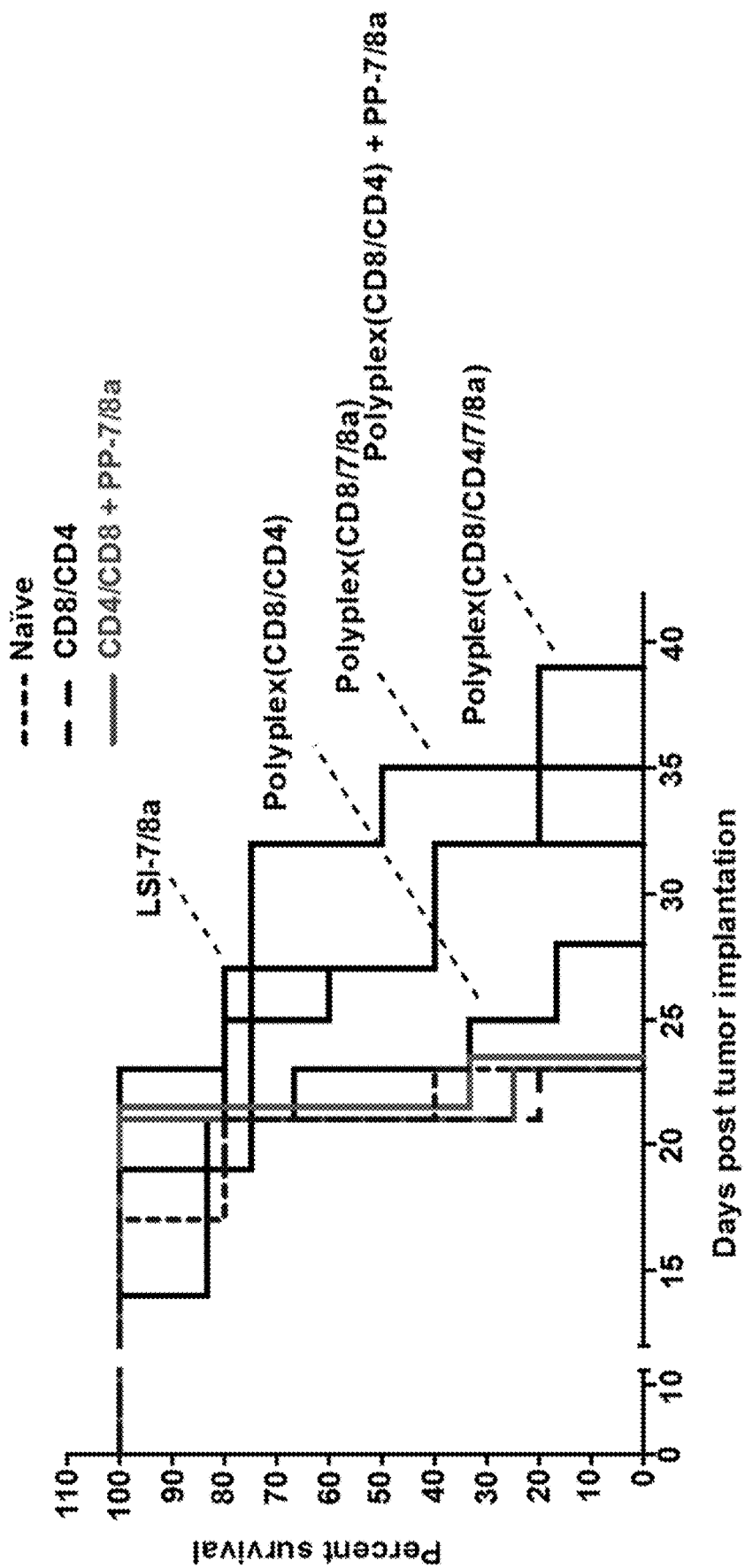
Figure 18C:
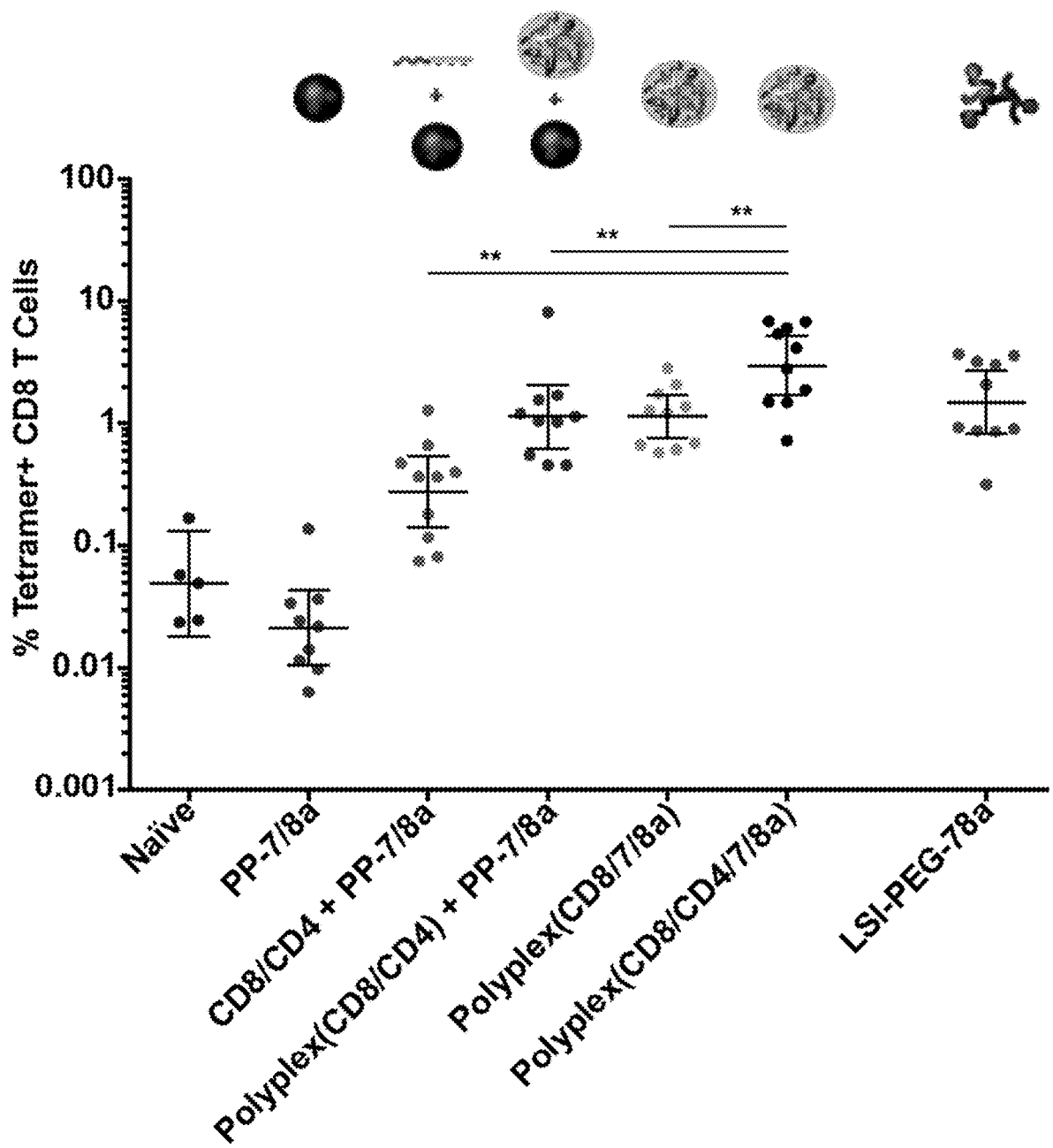
Figure 18D:
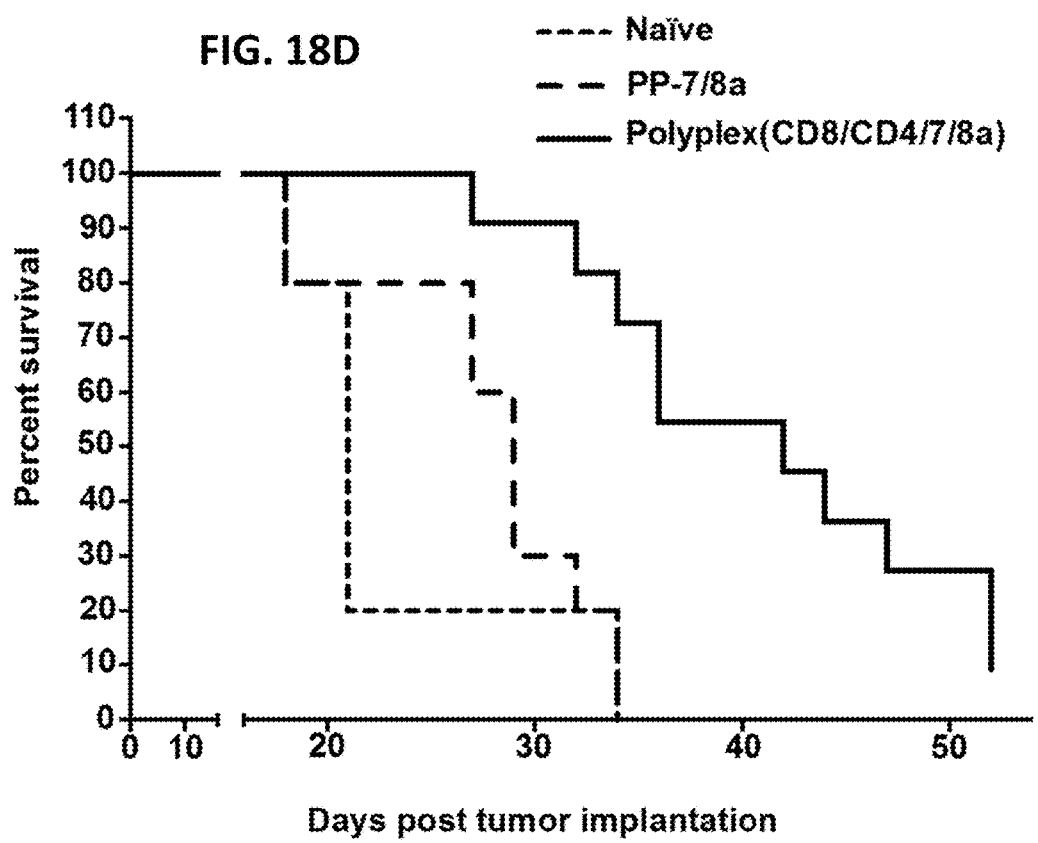

FIG. 17: The magnitude of CD8 T cell responses induced by polyplexes is independent of both the polymer comprising the polyplex and surface charge. Polyplexes were formed using CD8 and CD4 epitopes with C-terminal poly (glutamic acid) sequences complexed to either poly(lysine) (PLK)- or poly(ethylenimine) (PEI)-based TLR-7/8a carriers at a 5:1 positive to negative charge ratio. PEI-based polyplexes were combined with alginate to form particles with a net negative charge. The different polyplex compositions were delivered subcutaneously to the footpads of mice at days 0 and 7 and tetramer+ were administered from whole blood 1 week after 2 immunizations. Data on log scale are reported as geometric mean with 95% confidence interval (CI).

FIGS. 18A-18D: Co-delivering minimal CTL epitopes with CD4 help and TLR-7/8a within self-assembling nanoparticles enhances CD8 T cell immunity and tumor clearance. (18A) Synthetic long peptides were prepared with CD8 and CD4 epitopes fused to linker sequences comprised of 10 glutamic acid residues that are negatively charged at physiologic pH (7.4). The CD8 and CD4 epitopes with poly(glutamic acid) linkers were combined with poly(L-lysine)-based copolymer conjugates of TLR-7/8a (PLK-7/8a) at a 5:1 charge ratio to prepare nanoparticle electrostatic polymer complexes, referred to as polyplexes. (18A and 18B) Peptides alone or delivered as polyplexes admixed or co-delivered with TLR-7/8a were injected subcutaneously into the hind footpads of mice at days 0 and 14. At day 28, tetramer+ CD8 T cell responses were evaluated from whole blood of mice (n=5). (18B) Immunized mice were injected subcutaneously in the flank with 1×10$^5$ B16 melanoma cells expressing full-length Ovalbumin at day 42 and survival was assessed from 0 to 40 days post tumor inoculation. (18C and 18D) Mice were injected subcutaneously in the flank with 1×10$^5$ B16 melanoma cells expressing full-length Ovalbumin at day 0 and then were vaccinated subcutaneously in the footpad at days 3 and 17 post. (18C) Tetramer+ CD8 T cell responses were evaluated from whole blood of mice after a single immunization at day 16 (n=10) and (18D) survival (n=10) was followed out to day 50. Data are representative of two independent experiments. Data on log scale are reported as geometric mean with 95% confidence interval (CI). Student's T test was used for comparison of 2 groups; comparison of multiple groups for statistical significance was determined using one-way ANOVA with Bonferroni correction; ns, not significant (P>0.05); *, P<0.05; **, P<0.01.

Figure 19A:
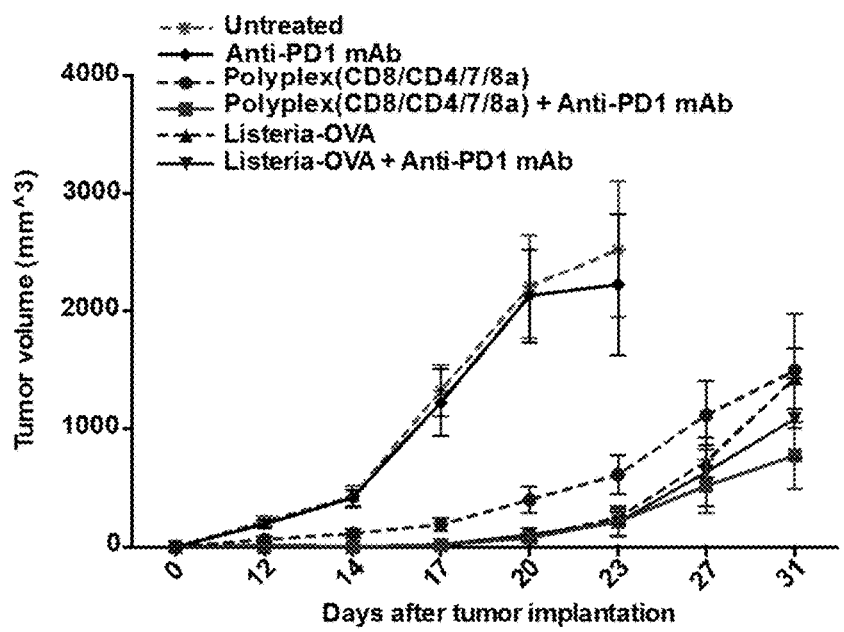
Figure 19B:
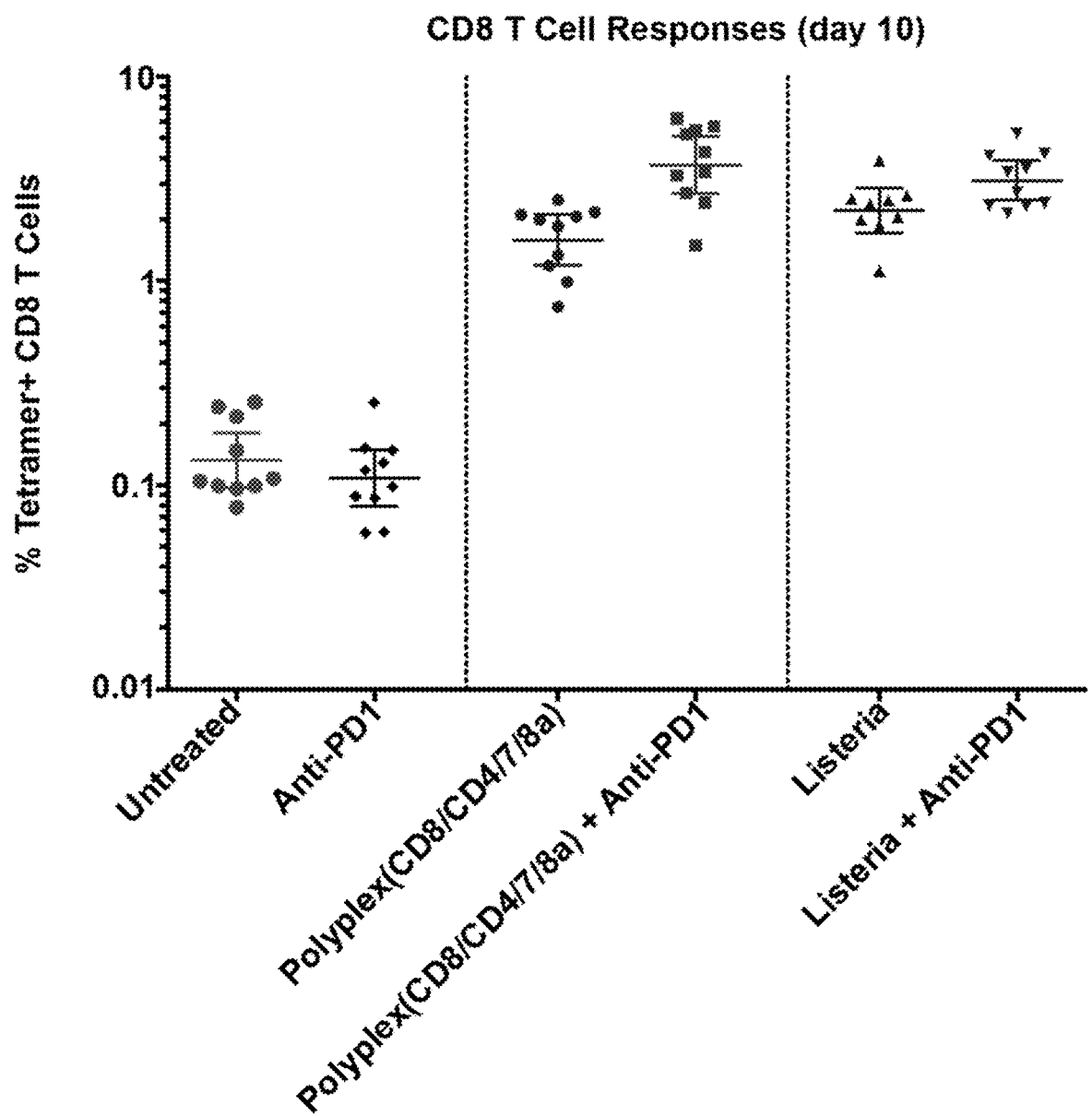
Figure 19C:
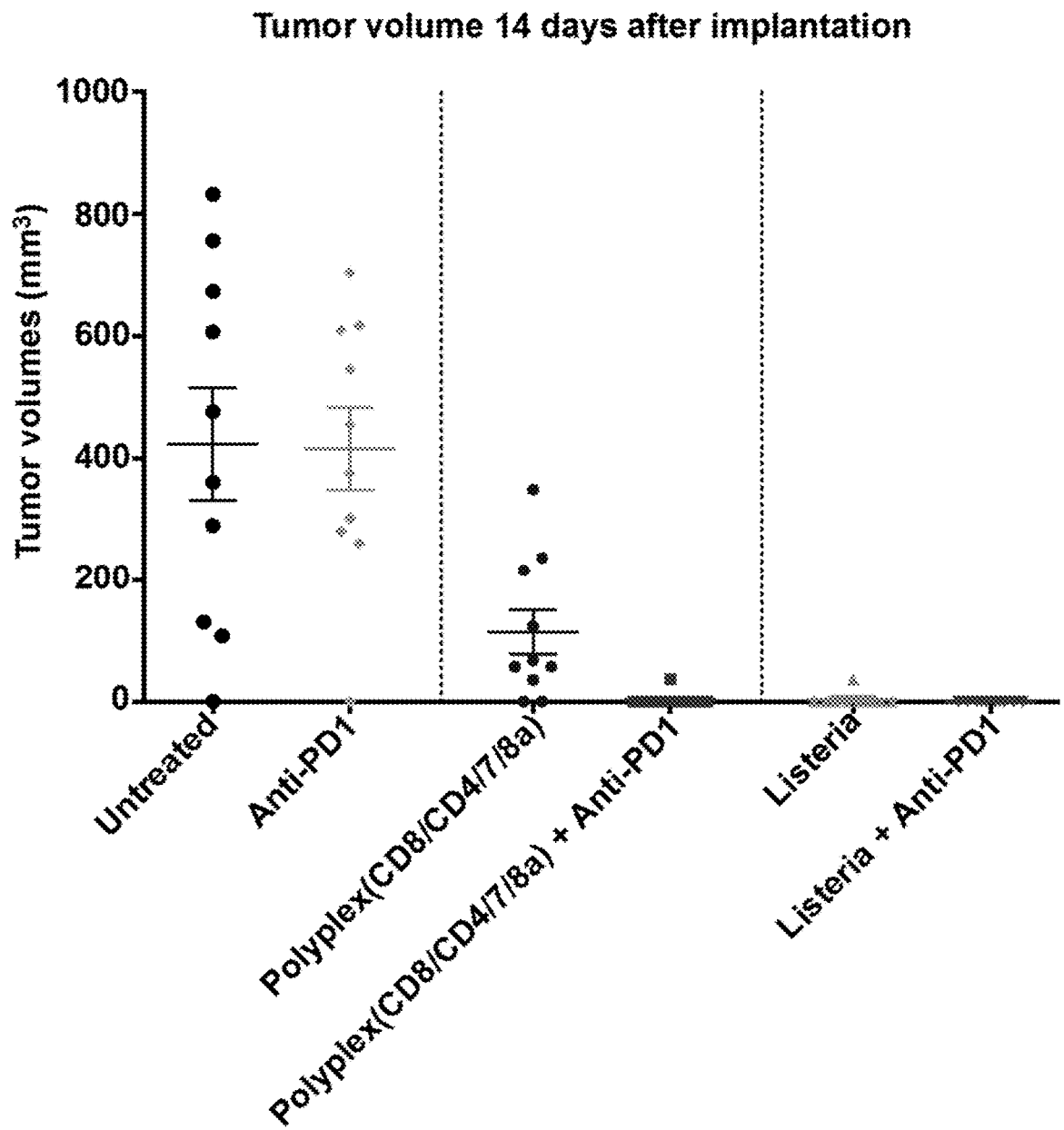

FIGS. 19A-19C: Peptide-based polyplex vaccines combined with anti-PD1 enhanced anti-cancer T cell immunity. (19A-19C) Mice were injected subcutaneously in the flank with 1×10$^5$ B16 melanoma cells expressing full-length Ovalbumin at day 0 and then were either vaccinated subcutaneously in the footpad at days 3 and 17 with peptide-based polyplexes or were injected intravenously with Listeria-expressing full-length Ovalbumin at day 3. Mice that received the anti-PD1 antibody (250 µg) were given IP injections at days 3, 7, 10, 14 and 17. (19A) Tumor size was monitored following tumor inoculation. Whole blood of mice was assessed at day 16 for tetramer+ CD8 T cell responses (19B) and tumor volumes at day 14 is provided (19C). Data on log scale are reported as geometric mean with 95% confidence interval (CI).

Figure 20A:
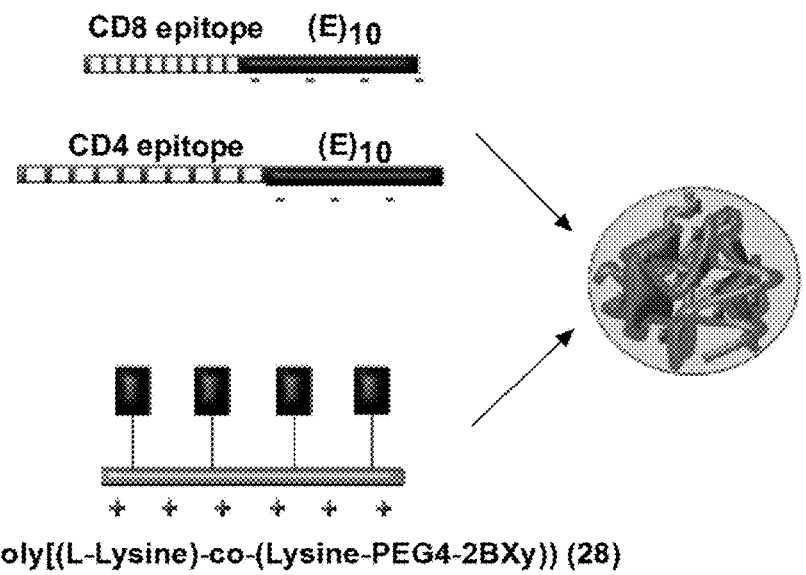
Figure 20B:
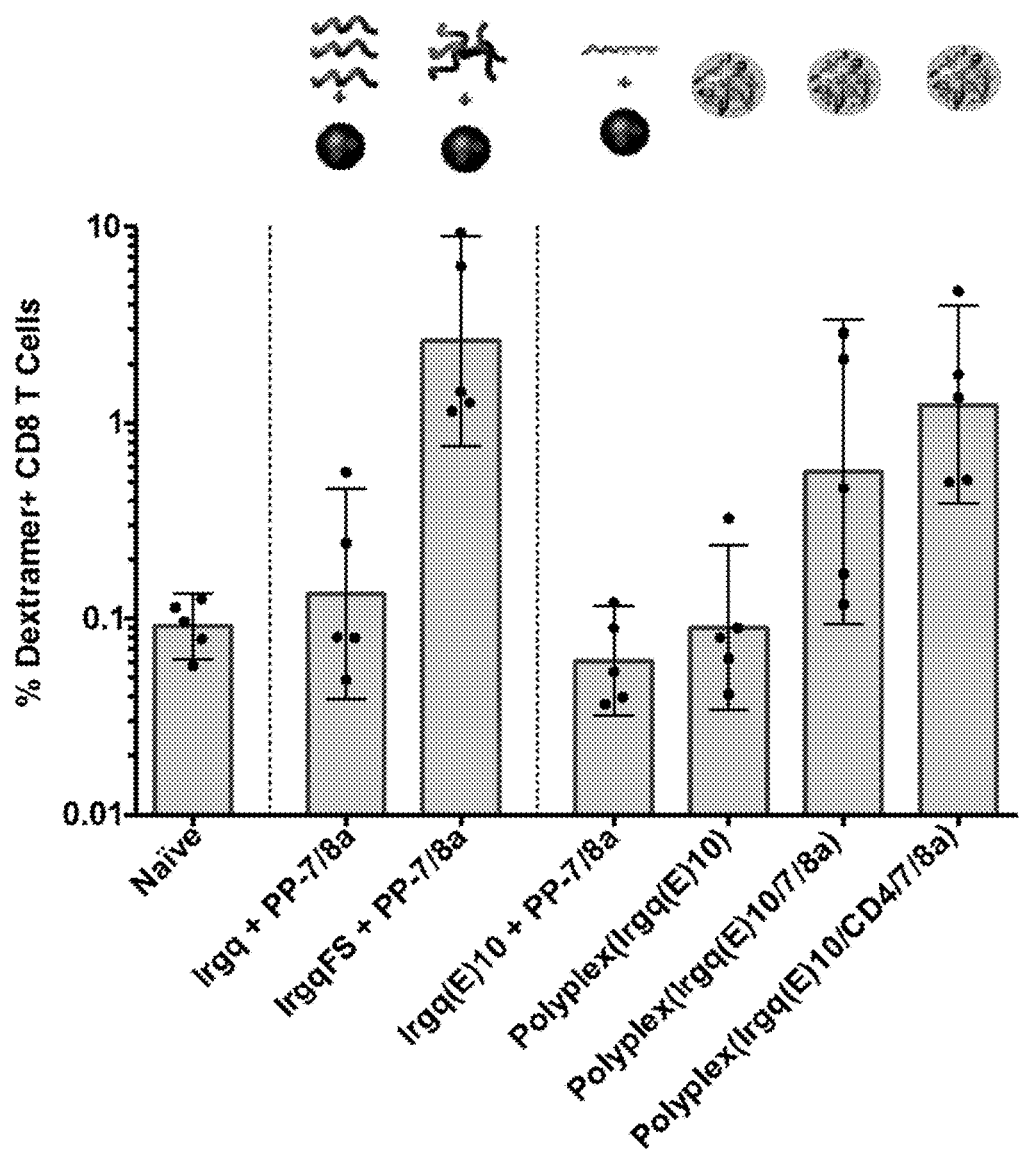

FIGS. 20A and 20B: CD8 T cell immunity to a peptide neoantigen is improved through co-delivery of a peptide antigen conjugates with TLR-7/8a in polymer nanoparticle polyelectrolyte complexes or polyplexes. (A) Synthetic long peptides were prepared with CD8 (33) and CD4 (32) epitopes fused to linker sequences comprised of 10 glutamic acid residues that are negatively charged at physiologic pH (7.4). The CD8 and CD4 epitopes with poly(glutamic acid) linkers were combined with poly(L-lysine)-based copolymer conjugates of TLR-7/8a (PLK-7/8a) (compound 28) at a 5:1 charge ratio to prepare nanoparticle electrostatic polymer complexes, referred to as polyplexes. (20B) Peptides alone or delivered as polyplexes admixed or co-delivered with TLR-7/8a were injected subcutaneously into the hind footpads of mice at days 0 and 14. At day 28, Dextramer+ CD8 T cell responses were evaluated from the whole blood of mice (n=5).

Figure 21A:
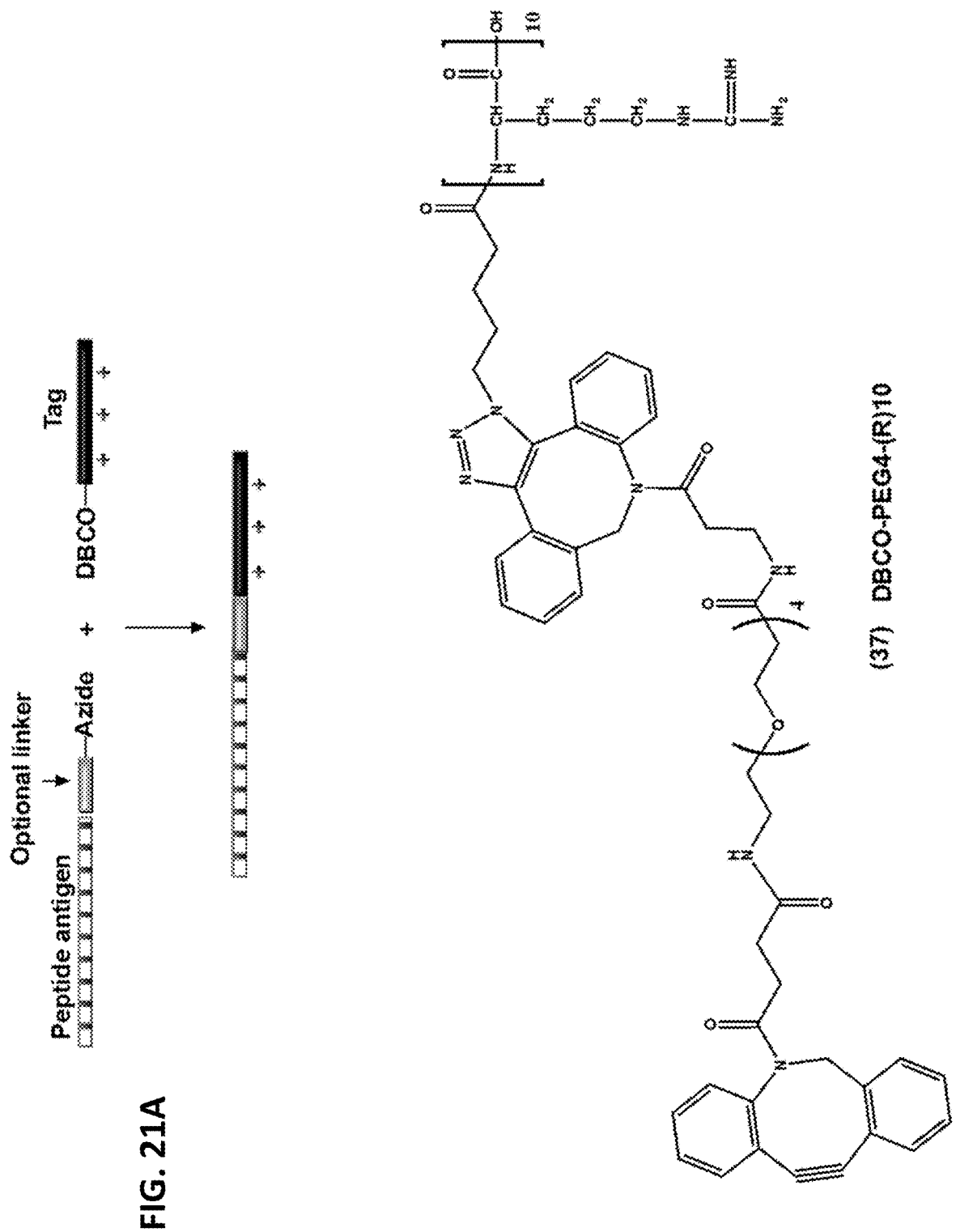
Figure 21B:
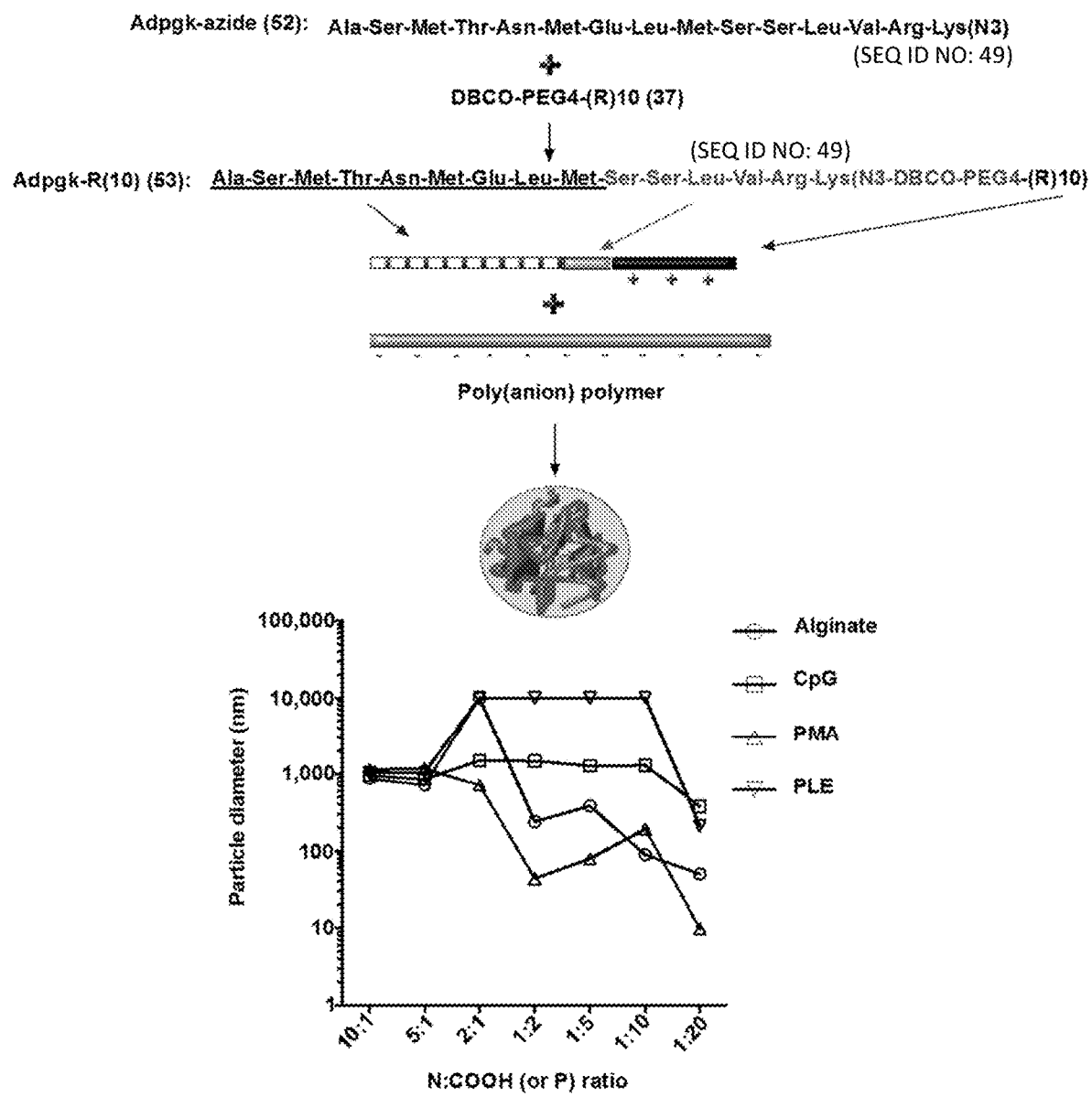

FIGS. 21A-21C: Positively charged peptide antigen conjugates formed by click chemistry coupling of a poly(cationic) peptide tag to peptide-based neoantigens. (21A) Schematic for the coupling of peptide tag sequences to peptide antigens through click chemistry and structure of DBCO-(R)$_{10}$ (compound 37), a poly(arginine) peptide tag that was coupled to azide modified peptide antigens to generate peptide antigen conjugates. (21B) A peptide antigen modified with an azide, Apdgk-azide (compound 52), was coupled to a compound 37 to generate a peptide antigen conjugate, compound 53. Compound 53 was used as an exemplary peptide antigen conjugate that was complexed with different poly(anions), sodium alginate, CpG nucleic acid, poly(methacrylic acid) and poly(L-glutamic acid) over a range of charge ratios in PBS, pH 7.4 to generate polyelectrolyte complexes that were assessed for particle sized by dynamic light scattering. (21C) Compound 53 was combined with different amounts (either 0.5, 1.0 or 3.0 mass equivalents relative to compound 53) of 25 kDa linear PEI (L-PEI) that were complexed in PBS, pH 7.4 with sodium alginate over a range of different charge ratios to generate polyelectrolyte complexes that were assessed for particle sized by dynamic light scattering.

Figure 22:
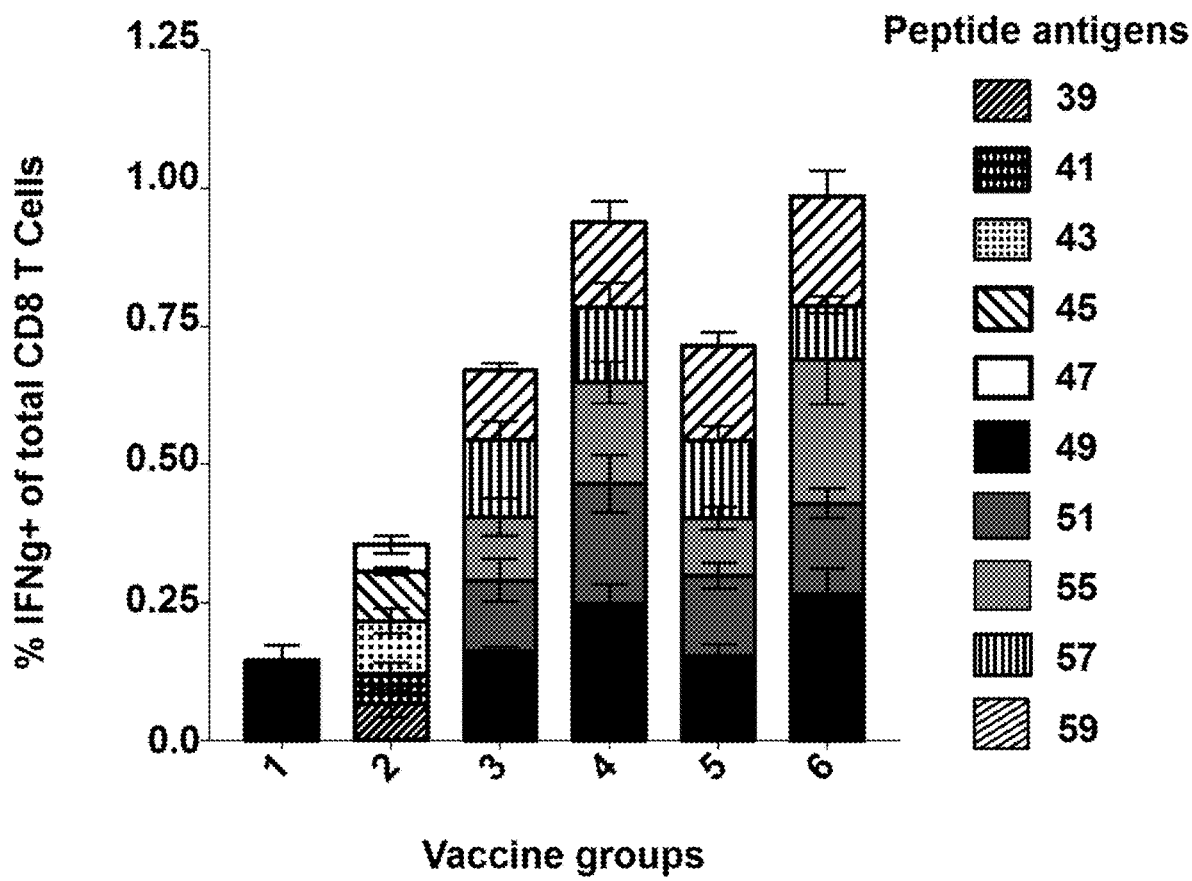

FIG. 22: Peptide-based neoantigens delivered as positively charged peptide antigen conjugates complexed with poly(anions) elicits neoantigen-specific CD8 T cell responses. Peptide antigen conjugates (compounds 39, 41, 43, 45, 47, 49, 51, 55, 57 and 59) comprised of 10 unique peptide-based neoantigens derived the MC38 tumor cell line were linked to a linker that was linked to $(Arg)_{10}$, and then either complexed with alginate at a charge ratio of 1:5 (N:COOH) and mixed with compound 5 (Groups 1 and 2); co-complexed with a PEI-based carrier of TLR-7/8a, compound 27, and alginate at a ratio of 1:5 (N:COOH); co-complexed with a poly(Arg)-based carrier of TLR-7/8a, compound 62; and alginate at a charge ratio of 1:5 (N:COOH); or complexed with the nucleic acid CpG at a charge ratio of 5:1 (N:P). The immunogenic compositions comprised of the polyelectrolyte complexes were administered into the hind footpad of mice at day 0. Whole blood was collected 6 days after 1 immunization for the magnitude of antigen-specific CD8 T cell responses. Responses to individual peptide antigens are represented as stacked bars.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~20 kb), which was created on Nov. 2, 2021, which is incorporated by reference herein.

DETAILED DESCRIPTION

Most contemporary peptide-based vaccine approaches for cancer treatment use CD4 and CD8 T cell epitopes of cancer antigens embedded within synthetic long peptides (~20-40 amino acids in length) that are admixed with vaccine adjuvants, such as emulsions (e.g., ISA-51 and CFA) and TLR agonists (e.g., polyICLC, CpG, etc.). The preference for the use of long peptides as a vaccine delivery platform is based on prior studies showing that long peptides improve antigen presentation and T cell priming in vivo as compared with minimal T cell epitopes delivered as short peptides or within the context of whole proteins. (see, e.g., Melief, C. J. & van der Burg, S. H. Immunotherapy of established (pre)malignant disease by synthetic long peptide vaccines. *Nat Rev Cancer* 8, 351-360 (2008). Kenter, G. G. et al. Vaccination against HPV-16 oncoproteins for vulvar intraepithelial neoplasia. *N Engl J Med* 361, 1838-1847, 2009. Speetjens, F. M. et al. Induction of p53-specific immunity by a p53 synthetic long peptide vaccine in patients treated for metastatic colorectal cancer. *Clin Cancer Res* 15, 1086-1095, 2009. Perez, S. A. et al. A new era in anticancer peptide vaccines. *Cancer* 116, 2071-2080, 2010. Rosario, M. et al. Long peptides induce polyfunctional T cells against conserved regions of HIV-1 with superior breadth to single-gene vaccines in macaques. *Eur J Immunol* 40, 1973-1984, 2010. Sabbatini, P. et al. Phase I trial of overlapping long peptides from a tumor self-antigen and poly-ICLC shows rapid induction of integrated immune response in ovarian cancer patients. *Clin Cancer Res* 18, 6497-6508, 2012. Yadav, M. et al. Predicting immunogenic tumour mutations by combining mass spectrometry and exome sequencing. *Nature* 515, 572-576, 2014. Kreiter, S. et al. Mutant MHC class II epitopes drive therapeutic immune responses to cancer. *Nature* 520, 692-696, 2015). Improved retention at the sites of vaccine administration, improved antigen presenting cell processing (i.e., increased access of long peptides to the cytosol) to promote cross-presentation and increased persistence of antigen presentation have all been reported as mechanisms of improved activity by long peptide-based vaccines. (den Boer, A. T. et al. Longevity of antigen presentation and activation status of APC are decisive factors in the balance between CTL immunity versus tolerance. *J Immunol* 167, 2522-2528 (2001). Bijker, M. S. et al. Superior induction of anti-tumor CTL immunity by extended peptide vaccines involves prolonged, DC-focused antigen presentation. *Eur J Immunol* 38, 1033-1042 (2008). Zhang, H. et al. Comparing pooled peptides with intact protein for accessing cross-presentation pathways for protective CD8+ and CD4+ T cells. *J Biol Chem* 284, 9184-9191 (2009)).

In contrast to this conventional wisdom, however, it was unexpectedly found that long peptides alone are not sufficient to elicit an immune response against minimal CD8 and CD4 T cell epitopes delivered within the context of the long peptide. Instead, it was observed that peptide assembly into particles (e.g., nano-sized supramolecular associates, nanoparticles or even microparticles and aggregates) together with an innate immune stimulator (adjuvant) that provides persistent innate immune stimulation in lymph nodes, are minimal requirements for eliciting T cell responses to peptide antigens. These results show that insoluble, particle forming, long peptides—but not water-soluble long peptides that do not undergo particle formation—are immunogenic in vivo. These results are unexpected since prior studies have focused on peptide length, but not solubility (i.e., propensity to undergo particle formation) as a parameter that strongly correlates with the capacity of peptide-based vaccines to elicit T cell responses. Though minimal epitopes that distribute systemically have been shown to induce tolerance and weak T cell responses as compared with minimal epitopes or long peptides delivered within emulsions that create an antigen depot, the influence of peptide solubility on immunogenicity has not been studied (Aichele, P., Brduscha-Riem, K., Zinkernagel, R. M., Hengartner, H. & Pircher, H. T cell priming versus T cell tolerance induced by synthetic peptides. *J Exp Med* 182, 261-266 (1995). den Boer, A. T. et al. Longevity of antigen presentation and activation status of APC are decisive factors in the balance between CTL immunity versus tolerance. *J Immunol* 167, 2522-2528 (2001). Toes, R. E., Offringa, R., Blom, R. J., Melief, C. J. & Kast, W. M. Peptide vaccination can lead to enhanced tumor growth through specific T-cell tolerance induction. *Proc Natl Acad Sci USA* 93, 7855-7860 (1996)).

Recent studies highlight the unexpected nature of the results disclosed herein, and their implications for the development of personalized cancer vaccines. For instance, in silico algorithms are currently being used to predict the immunogenicity of peptide neoantigens from patient tumor biopsies as a means of selecting only peptide antigens predicted to be immunogenic in vivo (i.e., capable of generating a T cell response) for inclusion in individualized cancer vaccines that are unique to each patient (see, e.g., Yadav, M. et al. Predicting immunogenic tumour mutations by combining mass spectrometry and exome sequencing. *Nature* 515, 572-576 (2014). Calis, J. J. et al. Properties of MHC class I presented peptides that enhance immunogenicity. *PLoS Comput Biol* 9, e1003266 (2013)). A limitation with this approach is that these predictive algorithms were trained on data sets using long peptide-based vaccines without taking into account the influence of the amino acid composition on the solubility of the peptide. As a result, these predictive algorithms underestimate the potential immunogenicity of soluble peptide sequences. As an example, it is shown herein that several neoantigens, including the Irgq, Cpne1 and Aatf neoantigens reported to be non-immunogenic based on the aforementioned predictive algorithm as well as in vivo testing (see, e.g., Yadav, M. et al. Predicting immunogenic tumour mutations by combining mass spectrometry and exome sequencing. *Nature* 515, 572-576 (2014)), can be rendered immunogenic by inducing the Irgq neoantigen to assemble into insoluble particles admixed or co-delivered with vaccine adjuvants. These results highlight the unexpected findings that the immunogenicity of soluble peptide sequences that may otherwise be predicted to be "non-immunogenic" using conventional methods of identifying peptide immunogens, can be rendered highly potent for inducing T cell responses by incorporating the soluble peptide sequences, or inducing their assembly, into particles. Moreover, as conventional wisdom suggested that long peptides may be more favorably processed than minimal peptide epitopes that directly bind to MHC molecules on the surfaces of APCS or larger proteins (or overlapping peptides expressed as proteins), it may be considered unexpected that insoluble and particulate peptides are found to be favorable for eliciting T cell responses in vivo, since single unimolecular long peptides have been considered heretofore to be optimal for eliciting CTL responses (Rosalia, R. A. et al. Dendritic cells process synthetic long peptides better than whole protein, improving antigen presentation and T-cell activation. *Eur J Immunol* 43, 2554-2565 (2013). Zhang, H. et al. Comparing pooled peptides with intact protein for accessing cross-presentation pathways for protective CD8+ and CD4+ T cells. *J Biol Chem* 284, 9184-9191 (2009)).

Based on the unexpected findings disclosed herein, several strategies are provided to deliver peptide-based neoantigens as particles co-delivered with persistent innate immune stimulation that is restricted to draining lymph nodes. The strategies described herein use electrostatic interactions alone or together with hydrophobic interactions and pi orbital stacking stacking to stabilize the complexes, i.e. polyplexes, formed between the peptide antigen conjugates and polymers of opposite charge, or between peptide antigen conjugates that interact through charge neutralization but are stabilized through a net charge. These strategies represent generalizable, controlled and chemically defined approaches for rendering any weakly immunogenic soluble peptide neoantigen into an immunogenic particle composition that can be co-delivered or admixed with vaccine adjuvants.

I. Terms

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

About: Plus or minus 5% from a set amount. For example, "about 5" refers to 4.75 to 5.25. A ratio of "about 5:1" refers to a ratio of from 4.75:1 to 5.25:1.

Adjuvant: Any material added to vaccines to enhance the immunogenicity of an antigen.

Adjuvants can include a suspension of minerals (alum, aluminum hydroxide, or phosphate) on which antigen is adsorbed; or water-in-oil emulsion, for example, in which antigen solution is emulsified in mineral oil (Freund's incomplete adjuvant), sometimes with the inclusion of killed mycobacteria (Freund's complete adjuvant) to further enhance immunogenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and Toll-like receptor (TLR) agonists, such as TLR-7/8 agonists. The person of ordinary skill in the art is familiar with adjuvants (see, e.g., Singh (ed.) Vaccine Adjuvants and Delivery Systems. Wiley-Interscience, 2007).

Administration: To provide or give to a subject an agent, for example, a composition including polymer nanoparticles comprising a peptide antigen and an adjuvant as described herein, by any effective route. Exemplary routes of administration include, but are not limited to, oral, injection (such as subcutaneous, electroporation (such as by endoscope electroporation), intramuscular, intradermal, intraperitoneal, and intravenous), sublingual, rectal, transdermal (for example, topical), intranasal, vaginal, and inhalation routes.

"Administration of" and "administering a" compound should be understood to mean providing a compound, a prodrug of a compound, or a pharmaceutical composition as described herein. The compound or composition can be administered by another person to the subject or it can be self-administered by the subject.

Antigen-presenting cell (APC): A cell that can present antigen bound to MHC class I or class II molecules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

Aromatic: Aromatic compounds or groups are typically unsaturated, cyclic hydrocarbons having alternate single and double bonds. Benzene, a 6-carbon ring containing three double bonds, is a typical aromatic compound. An aromatic amino acid is an amino acid having a side chain comprising an aromatic group, such as phenylalanine, tyrosine, or tryptophan.

Biocompatible: Exerting minimal destructive or host response effects while in contact with body fluids or living cells or tissues. Thus a biocompatible group may contain an aliphatic, alicyclic, heteroaliphatic, heteroalicyclic, aryl or heteroaryl moiety, which falls within the definition of the term biocompatible. The term "biocompatibility" is alternatively taken to mean minimal interactions with recognition proteins, e.g., naturally occurring antibodies, cell proteins, cells and other components of biological systems. However, substances and functional groups specifically intended to cause the above effects, e.g., drugs and prodrugs, are considered to be biocompatible.

CD4: Cluster of differentiation factor 4, a T cell surface protein that mediates interaction with the MHC Class II molecule. Cells that express CD4 are often helper T cells.

CD8: Cluster of differentiation factor 8, a T cell surface protein that mediates interaction with the MHC Class I molecule. Cells that express CD8 are often cytotoxic T cells.

Effective amount: The amount of an agent that alone, or together with one or more additional agents, induces the desired response, such as, for example induction of an immune response to a peptide antigen.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogenic composition: A composition comprising a peptide antigen that induces a measurable CTL response against the antigen, or induces a measurable B cell response (such as production of antibodies) against the peptide antigen.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties). As used herein, "linked" and variations thereof refer to components that maintain a chemical or physical association after immunization at least until they contact a cell, such as an immune cell.

In several embodiments, linked components are associated in a chemical or physical manner so that the components are not freely dispersible from one another, at least until contacting a cell, such as an immune cell. For example, two components may be covalently bound to one another so that the two components are incapable of separately dispersing or diffusing. Linking is specifically distinguished from a simple mixture of antigen and adjuvant such as may be found, for example, in a conventional vaccine. In a simple mixture, the components can be free to independently disperse within the vaccinated environment.

Linker: A molecule or group of atoms positioned between two moieties. For example, a monomer in a polymer that is conjugated to an adjuvant may include a linker between the monomer and the adjuvant. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker.

Nanoparticle: A nano-sized particle structure including a peptide antigen that can form in aqueous solution and can be taken up into cells (e.g., immune cells). The nano-particle can be a supra-molecular structure comprised of an assembly of molecules, including micelles, bilayers and other types of ordered or random assemblies. Nanoparticles used in the disclosed embodiments include a peptide that can be taken up into cells (e.g., immune cells). The nanoparticles used in the disclosed embodiments have an average diameter of from 20 to 1000 nm. In some embodiments, the nanoparticles may be included in larger particle structures, including those that are too large for uptake by immune cells (e.g., particles larger than about 5000 nm) and that slowly release the nanoparticles including the peptide antigen as a function of their degradation.

In several embodiments, the disclosed nanoparticles are peptide nanoparticles that are formed by association of peptides including a peptide antigen into the nanoparticle structure. In several embodiments, such peptide nanoparticles can be administrated to a subject without causing toxic side effects.

In several embodiments, the disclosed nanoparticles are polymer nanoparticles that are formed by association of polymers linked to a peptide antigen into the nanoparticle structure. In some embodiments, an adjuvant is also linked to the polymer. In several embodiments, such polymer nanoparticles can be administrated to a subject without causing toxic side effects.

In some embodiments, nanoparticles (such as peptide nanoparticles or polymer nanoparticles) can be prepared that include an adjuvant (such as a TLR-7/8 agonist) by admixing the adjuvant with the nanoparticle.

Pattern recognition receptor: A protein receptor expressed by cells of the immune system to identify pathogen-associated molecular patterns (PAMPS) as well as damage associated molecular patterns (DAMPs). PAMP or DAMP activation of pattern recognition receptors induces an intracellular signaling cascade resulting in the alteration of the host cell's transcription profile to induce expression of pro-inflammatory and pro-survival genes that enhance adaptive immunity. Non-limiting examples of pattern recognition receptors (PRRs) include Toll-like receptors (TLR), Stimulator of Interferon Genes receptor (STING), C-type lectin receptors (CLR), RIG-I-like receptors (RLR), and NOD-like receptors (NLR). Agonists of such pattern recognition receptors can be used as adjuvants for enhancing an immune response to a target antigen.

Toll-like receptors (TLRs) 1-13 are transmembrane PRRs that recognize a diverse range of PAMPs. TLRs can be divided into two broad categories—those that are localized to the cell surface and those that are localized to the endosomal lumen. TLRs that are present on the cell surface are important in recognition of bacterial pathogens. TLRs that are localized to the lumen of endosomes, such as TLRs 3, 7, 8, and 9, serve to recognize nucleic acids and are thus thought to be important in the promotion of antiviral immune responses. TLR-7 and TLR-8 recognize ssRNA. Several different imidazoquinoline compounds are known TLR-7/8 agonists. TLR-9 recognizes unmethylated deoxycytidylate-phosphate-deoxyguanylate (CpG) DNA, found primarily in bacteria.

The NOD-like receptors (NLRs) and the RIG-I-like receptors (RLRs) are localized to the cytoplasm. Non-limiting examples of RLRs include RIG-I, MDA5, and LGP2. There are 22 human NLRs that can be subdivided into the five structurally related NLR families A, B, C, P, and X. All NLRs have three domains: an N-terminal domain involved in signaling, a nucleotide-binding NOD domain, and a C-terminal leucine rich region (LRR) important for ligand recognition. Non-limiting examples of NLRs include NALP3 and NOD2.

For more information on pattern recognition receptors, see Wales et al., Biochem Soc Trans., 35:1501-1503, 2007.

Peptide: A polymer in which the monomers are amino acid residues that are joined together through amide bonds. The amino acids included in a peptide may be subject to post-translational modification (e.g., glycosylation or phosphorylation). In some embodiments, a peptide can be between 8 and 30 amino acids in length, such as from 8 to 12 amino acids in length or 22-26 amino acids in length. In several embodiments, a polypeptide or peptide is at most 50 amino acids in length, for example, 9, 10, 11 or 12 amino acids in length.

Peptide Antigen: A peptide that can stimulate the production of antibodies or a T cell response in an animal. A peptide antigen contains an epitope that can react with the products of specific humoral or cellular immunity to induce an immune response to the epitope. "Epitope" refers to the region of a peptide antigen to which B and/or T cells respond.

In some examples, a peptide antigen can include a portion of a polypeptide from a pathogen of interest (such as a virus) or a diseased tissue of interest (such as a tumor). A peptide antigen that can stimulate the production of antibodies or a T cell response in a subject to a polypeptide expressed by a virus is a viral antigen.

A peptide antigen that can stimulate the production of antibodies or a T cell response in a subject to a polypeptide primarily expressed by tumor tissue, but not healthy tissue, is a tumor associated peptide antigen. A tumor associated peptide antigen typically comprises an allele-specific motif or other sequence of a tumor associated antigen, such that the peptide will bind an MHC molecule and induce a cytotoxic T lymphocyte ("CTL") response, or a B cell response (e.g. antibody production) against the antigen from which the tumor associated peptide antigen is derived.

Peptide Modifications: Immunogenic peptides include synthetic embodiments of peptides described herein. In addition, analogs (non-peptide organic molecules), derivatives (chemically functionalized peptide molecules obtained starting with the disclosed peptide sequences) and variants (homologs) of these peptides can be utilized in the methods described herein. Each peptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide for the incorporation of certain functionalities of linkage of ligand molecules, such as an adjuvant.

Hydroxyl groups of the peptide side chains may be converted to $C_1$-$C_{16}$ alkoxy or to a $C_1$-$C_{16}$ ester using well-recognized techniques to introduce hydrophobic characteristics to the peptide. Alternatively, the hydroxyl groups may be sulfated or phosphorylated to introduce negative charge and increase water solubility. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Thiols may be reacted with maleimides or disulfides. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic peptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, IL, pp. 165-174 and *Principles of Pharmacology*, Munson (ed.) 1995, Ch. 102, for descriptions of techniques used in CADD. Also included are mimetics prepared using such techniques.

Peptide tag: A peptide that can be linked to a heterologous molecule (such as another peptide) to provide a function to the resultant conjugate. In some embodiments a peptide tag can be linked to a heterologous peptide using genetic engineering; the linkage can be direct, or indirect via a peptide linker. In several embodiments, a peptide tag can be used to functionalize a heterologous molecule with an electrostatic charge. In such embodiments, the peptide tag can include amino acids having the charge (positive or negative) of interest.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, PA, 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymer: A molecule of repeating structural units (monomers). The polymers included in the disclosed embodiments can form polymer nanoparticles that can be administrated to a subject without causing toxic side effects. Further, the polymers included in the disclosed embodiments include a side chain with a functional group that can be utilized, for example, to facilitate linkage to an adjuvant. In several embodiments, the polymer can be a cationic polymer (that is, a polymer with a predominantly positive charge) that can form a complex with a conjugate comprising a peptide antigen by electrostatic interaction. Non-limiting examples of cationic polymers that can be used in the disclosed embodiments include poly(amino acids), such as poly(arginine) or poly(lysine), polyphosphoesters bearing cationic functionalities (e.g., amine groups), poly(amidoamines)s, poly(ethylenimine) (PEI), and Poly(beta-amino ester) (PBAE) based polymers. Non-limiting examples of anionic polymers that can be used in the disclosed embodiments include poly(glutamic acid), poly(aspartic acid), a polyphosphoester-based polymer, or the polymer may comprise natural anionic polysaccharides, including, e.g., alginic acid.

Polymerization: A chemical reaction, usually carried out with a catalyst, heat or light, in which a large number of relatively simple molecules (monomers) combine to form a chainlike macromolecule (a polymer). The chains further can be combined, or crosslinked, by the addition of appropriate chemicals. The monomers typically are unsaturated or otherwise reactive substances. Polymerization commonly occurs by addition or condensation. Addition polymerization occurs when an initiator, usually a free radical, reacts with a double bond in the monomer. The free radical adds to one side of the double bond, producing a free electron on the other side. This free electron then reacts with another monomer, and the chain becomes self-propagating. Condensation polymerization involves the reaction of two monomers, resulting in the splitting out of a water molecule.

Polyplex: A polyelectrolyte complex formed through electrostatic condensation between polymers of opposite charge. A poly(amino acid) polymer with a net negative charge may undergo electrostatic condensation with a polymer of opposite (positive) charge to form a polyelectrolyte complex, which can be referred to as a polyplex. Nano-sized polyplexes are referred to as nanoparticle polyplexes. A polymer nanoparticle comprised of a polyelectrolyte complex is a polyplex.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Soluble: Capable of becoming molecularly or ionically dispersed in a solvent to form a homogeneous solution. A soluble peptide is understood to be a single molecule in solution that does not assemble into multimers or other supramolecular structures through hydrophobic or non-specific interactions. In several embodiments, a peptide antigen can be a soluble peptide antigen that dissolves to a concentration of at least 0.1 mg/mL in phosphate buffered saline, pH 7.4 at room temperature. In some embodiments, a peptide antigen conjugate can be a soluble conjugate that dissolves to at least 0.1 mg/mL phosphate buffered saline (PBS), pH 7.4 at room temperature. Solubility can be determined visually or using spectroscopic techniques. Turbidity measurements allow for solubility determination indirectly by using a spectrophotometer to measure absorbance in the visible spectrum, typically between 300-500 nm; insoluble materials scatter light that reduces transmittance, leading to increases in measured absorbance (OD). Herein, absorbance measurements at 490 nm were used to assess solubility.

Subject: Includes both human and non-human subjects, including birds and non-human mammals, such as non-human primates, companion animals (such as dogs and cats), livestock (such as pigs, sheep, cows), as well as non-domesticated animals, such as the big cats.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

Treating, preventing, or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Reducing a sign or symptom of a disease or pathological condition related to a disease, refers to any observable beneficial effect of the treatment. Reducing a sign or symptom associated with a tumor or viral infection can be evidenced, for example, by a delayed onset of clinical symptoms of the disease in a susceptible subject (such as a subject having a tumor which has not yet metastasized, or a subject that may be exposed to a viral infection), a reduction in severity of some or all clinical symptoms of the disease, a slower progression of the disease (for example by prolonging the life of a subject having a tumor or viral infection), a reduction in the number of relapses of the disease, an improvement in the overall health or well-being of the subject, or by other parameters well known in the art (e.g., that are specific to a particular tumor or viral infection). A "prophylactic" treatment is a treatment administered to a subject who does not exhibit signs of a disease or exhibits only early signs for the purpose of decreasing the risk of developing pathology.

In one example, a desired response is to induce an immune response that leads to a reduction in the size, volume, or number (such as metastases) of a tumor in a subject. For example, the agent or agents can induce an immune response that decreases the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Tumor or cancer: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

An "established" or "existing" tumor is an existing tumor that can be discerned by diagnostic tests. In some embodiments, an established tumor can be palpated. In some embodiments, an "established tumor" is at least 500 mm$^3$, such as at least 600 mm$^3$, at least 700 mm$^3$, or at least 800 mm$^3$ in size. In other embodiments, the tumor is at least 1 cm long. With regard to a solid tumor, an established tumor generally has an robust blood supply, and has induced Tregs and myeloid derived suppressor cells (MDSC).

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Therefore, comprising "A" or "B" refers to including A, including B, or including both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described herein. In case of conflict, the present specification, including explanations of terms, will control. In addition, the materials, methods, and examples are illustrative only and not intended to be limiting.

II. Immunogenic Compositions

Disclosed herein are novel immunogenic compositions comprising a peptide antigen conjugate comprising a peptide antigen linked to a peptide tag through an optional linker. In some embodiments, the peptide tag provides an electrostatic charge to the peptide antigen conjugate that facilitates nanoparticle formation in in aqueous buffer, such as phosphate buffered saline, pH 7.4, by the peptide antigen conjugate itself. In additional embodiments, the peptide tag provides an electrostatic charge to the peptide antigen conjugate that facilitates electrostatic interaction with a polymer to form a complex through charge neutralization, and the conjugate/polymer complex can form polymer nanoparticles in aqueous buffers, such as phosphate buffered saline, pH 7.4. The nanoparticle complex of polymers is referred to as a polyplex. The nanoparticles in the composition can be taken up into a cell (such as an immune cell, for example, an antigen presenting cell) under physiological conditions to induce an immune response to the peptide antigen in a subject. A detailed discussion of the components of the disclosed immunogenic compositions follows.

Conjugates

The conjugate comprises (A) peptide antigen, (B) optional linker, and (C) peptide tag sequence. In the discussion that follows, the following letter designations are used to describe peptide antigen conjugates:

Peptide Antigen (A)
   A=A peptide comprised of a sequence of amino acid residues that is antigenic Optional Linker (B):
   B=Denotes the antigen linker sequence, which serves to link the Antigen (A) to the Peptide Tag (C). In preferred embodiment the linker is comprised of hydrophilic non-charged amino acids and non-natural amino acids, such as Serine (Ser), Threonine (Thr) and Glycine (Gly) or hydrophilic linkers (e.g., PEG). In preferred embodiments, amide bonds link the linker to the antigen and peptide tag sequences. In some embodiments, the PEG linker can include ethylene oxide linkers comprised of 2-24 ethylene oxide units. The linker may comprise a cleavable peptide spacer, including a tetrapeptide. Exemplary tetrapeptide sequences include those that are recognized and cleaved by endosomal proteases, wherein the P4 position of a tetrapeptide linker ($P_1$-$P_2$-$P_3$-$P_4$) is optionally selected from Arginine, Citruline, Lysine, Isoleucine, Leucine or Norleucine. In preferred embodiments, the linker links the tag to the C-terminus of the peptide antigen.

Peptide Tag sequence (C):
   X=Positively charged amino acids and non-natural amino acids, such as Arginine (Arg), Lysine (Lys) or N,N,N-Trimethyllysine
   Y=Negatively charged amino acids and non-natural amino acids, such as Glutamic Acid (Glu) and Aspartic Acid (Asp), or modified amino acids, such as sulfated or phosphorylated Serine, Threonine or Tyrosine.
   Z=Hydrophobic amino acids, particularly those capable of undergoing Pi orbital stacking, including Phenylalanine (Phe), Tyrosine (Tyr), Tryptophan (Trp) and Benzyl Glutamate.

The peptide tag sequence is chosen to (1) promote solubility of the peptide antigen conjugate in common solvents and aqueous buffers over certain pH ranges to facilitate manufacturing; and (2) promote particle assembly through electrostatic interactions. A peptide tag sequence may be placed at either or both the N- and the C-terminus of the peptide antigen via an optional linker.

(1) Peptide Antigen Conjugates that Complex with Polymers Through Electrostatic Interactions to Form Particle Complexes Minimal CD4 and CD8 T cell epitopes of between 8-14 amino acids in length can be delivered as the minimal epitope linked to a Peptide Tag sequence comprised of charged amino acids connected through an optional linker, such as a PEG spacer or cleavable tetrapeptide linker. The charged residues flanking the antigen can be used to drive particle formation through electrostatic interactions with charged polymers that together self-assemble into polymer complexes referred to as polyplexes.

Example peptide antigen conjugates include:
$A_{8-12}$-B-$X_l$+negatively charged poly(anionic) polymer
$A_{8-12}$-B-$Y_m$+positively charged poly(cationic) polymer
$A_{8-14}$-B-$X_l$+negatively charged poly(anionic) polymer
$A_{8-14}$-B-$Y_m$+positively charged poly(cationic) polymer Peptide Tag sequences for this construct are preferably no more than 20 amino acids in length. For instance, for $X_l$, l=20. A non-limiting example could be $(Lys)_{20}$ (SEQ ID NO: 2), or $(Arg)_{20}$ (SEQ ID NO: 3). For instance, for $Y_m$, m=20. In preferred embodiments, the tag sequence is between 5-15 amino acids in length, e.g., 10 amino acids in length.

For the delivery of neoantigens with poorly defined epitopes, an exemplary embodiment is a 29-35 amino acid peptide-based neoantigen defined by the 14-17 N- and C-terminal amino acids on each side of the mutant amino acid (i.e., defining the variant allele of the neoantigen, which defines the mutation) that is linked to a peptide tag sequence comprised of charged amino acids connected through a linker. Note that 29-35 amino acid peptide neoantigen sequences preferably contain all of the CD4 and CD8 T cell epitopes for a given peptide neoantigen. The charged residues flanking the antigen can be used to drive particle formation through electrostatic interactions with charged polymers that together self-assemble into particle complexes referred to as polyplexes.

Example peptide antigen conjugates include:
$A_{12-40}$-B-$X_l$+negatively charged poly(anionic) polymer
$A_{12-40}$-B-$Y_m$+positively charged poly(cationic) polymer Peptide Tag sequences for this construct are preferably no more than 20 amino acids in length. For instance, for $X_l$, l=20. A non-limiting example could be $(Lys)_{20}$ (SEQ ID NO: 2) or $(Arg)_{20}$. (SEQ ID NO: 3). For instance, for $Y_m$, m=20. In preferred embodiments, the tag sequence is between 5-15 amino acids in length, e.g., 10 amino acids in length, such as $(Arg)_{10}$ (residues 1-10 of SEQ ID NO: 3).

In some embodiments, a peptide antigen conjugate is complexed with a peptide antigen conjugate of opposing charge to form nanoparticles complexes, for example:
$A_{12-40}$-B-$X_l$+$A_{12-40}$-B-$Y_m$ (2) Peptide antigen conjugates that complex with polymers through electrostatic interactions combined to form particle complexes stabilized by Pi orbital stacking Minimal CD4 and CD8 T cell epitopes can be linked to a peptide tag sequence comprised of charged amino acids connected through an optional linker. The charged residues flanking the antigen can be used to drive particle formation through electrostatic interactions with charged polymers that together self-assemble into particle complexes referred to as polyplexes. Aromatic groups on either or both the peptide and polymer can further stabilize the particles through Pi orbital stacking and hydrophobic interactions.

Example peptide antigen conjugates include:
$A_{8-12}$-B-$X_l$-$Z_n$+negatively charged poly(anionic) co-polymer with optional aromatic groups
$A_{8-12}$-B-$Y_m$-$Z_n$+positively charged poly(cationic) co-polymer with optional aromatic groups Peptide Tag sequences for this construct are preferably no more than 22-25 amino acids in length, with between 2-5 aromatic amino acid residues. For instance, for $X_l$, l=20 and $Z_n$, z=2. A non-limiting example could be $(Lys)_{20}$-$(Trp)_2$ (SEQ ID NO: 4). For instance, for $Y_m$, m=20 and $Z_n$, z=2. The number or aromatic residues is selected to promote improved stability of the formed polyplexes without causing the peptide antigen conjugate alone, prior to complexation, to be insoluble during manufacturing in common solvent systems used for peptide manufacturing, such as acetonitrile, DMSO, DMF dimethyl acetamide and water.

For the delivery of neoantigens with poorly defined epitopes, an exemplary embodiment is a 29-35 amino acid peptide-based neoantigen defined by the 14-17 N- and C-terminal amino acids on each side of the mutant amino acid (i.e., defining the variant allele of the neoantigen, which defines the mutation) that is linked to a peptide tag sequence comprised of charged amino acids connected through an optional linker. Note that 29-35 amino acid peptide neoantigen sequences preferably contain all of the CD4 and CD8 T cell epitopes for a given peptide neoantigen. The charged residues of the peptide antigen conjugate can be used to drive particle formation through electrostatic interactions with charged polymers that together self-assemble into particle complexes referred to as polyplexes. Aromatic groups on both the peptide and polymer can further stabilize the particles through Pi orbital stacking and hydrophobic interactions.

Example peptide antigen conjugates include:
$A_{12-40}$-B-($X_l$-$Z_n$)+negatively charged poly(anionic) co-polymer with optional aromatic groups
$A_{12-40}$-B-($Y_m$-$Z_n$)+positively charged poly(cationic) co-polymer with optional aromatic groups Peptide Tag sequences for this construct are preferably no more than 22-25 amino acids in length, with between 2-5 aromatic amino acid residues. For instance, for $X_l$, l=20 and $Z_n$, z=2. A non-limiting example could be $(Lys)_{20}$-$(Trp)_2$ (SEQ ID NO: 4). For instance, for $Y_m$, m=20 and $Z_n$, z=2.

(3) Peptide Antigen Conjugates Induced to Form Particles Through Electrostatic Interactions Minimal CD4 and CD8 T cell epitopes can be delivered as the minimal epitope linked to a peptide tag sequence comprised of charged amino acids connected through an optional linker. The charged residues flanking the antigen on the peptide tag sequence can be used to drive particle formation through either inter- or intra-molecular electrostatic interactions that promotes formations of supramolecular assemblies.

Example peptide antigen conjugate: $A_{8-12}$-B-$X_l$-$Y_m$)

Tag sequences for this construct are preferably no more than 20 amino acids in length, with a molar excess of either X or Y. The tag sequences have a molar excess of negatively charged or positively charged residues to provide a net negative or positive charge, respectively. The peptide tag comprises a ratio of positively charged amino acids to negatively charged amino acids of from 1.2 to 6:1 if the conjugate comprises the net positive charge; or the peptide tag comprises a ratio of negatively charged amino acids to positively charged amino acids of from 1.2:1 to 6:1 if the conjugate comprises the net negative charge.

In a non-limiting example the tag sequence may be 20 amino acids in length with excess charge at a ratio of 3:1, e.g., $X_{15}$-$Y_5$ or $X_5$-$Y_{15}$ comprising $(Lys)_{15}$-$(Glu)_5$ (SEQ ID NO: 5) or $(Lys)_5$-$(Glu)_{15}$ (SEQ ID NO: 6). Alternatively, the tag sequence may be $X_{16}$-$Y_4$ or $X_4$-$Y_{16}$, for example, comprising $(Lys)_{16}$-$(Glu)_4$ (SEQ ID NO: 7) or $(Lys)_4$-$(Glu)_{16}$ (SEQ ID NO: 8). In a non-limiting example, the peptide tag is comprised of 20 amino acids and the charge ratio is 1.5:1, e.g., $(Lys)_{12}(Glu)_5$ (SEQ ID NO: 9); X or Y may occur as blocks, e.g., $(Lys)_{12}$-$(Glu)_5$ (SEQ ID NO: 9) or may be alternating, e.g, Lys-Lys-Glu-Lys-Lys-Glu-Lys-Lys-Glu-Lys-Lys-Glu-Lys-Lys (SEQ ID NO: 10), or random, e.g., Glu-Lys-Lys-Lys-Lys-Lys-Glu-Glu-Lys-Glu-Lys-Lys-Lys-Lys-Lys (SEQ ID NO: 11).

For the delivery of neoantigens with poorly defined epitopes, an exemplary embodiment is a 29-35 amino acid peptide-based neoantigen defined by the 14-17 N- and C-terminal amino acids on each side of the mutant amino acid (i.e., defining the variant allele of the neoantigen, which defines the mutation) that is linked to a peptide tag comprised of charged amino acids connected through an optional linker. Note that 29-35 amino acid peptide neoantigen sequences preferably contain all of the CD4 and CD8 T cell epitopes for a given peptide neoantigen. The charged residues flanking the antigen can be used to drive particle formation through electrostatic interactions.

Example peptide antigen conjugate: $A_{12-40}$-B-$(X_l$-$Y_m)$

In a non-limiting example the tag sequence may be 20 amino acids in length with excess charge at a ratio of 3:1, e.g., $X_{15}$-$Y_5$ or $X_5$-$Y_{15}$ comprising $(Lys)_{15}$-$(Glu)_5$ (SEQ ID NO: 5) or $(Lys)_5$-$(Glu)_{15}$ (SEQ ID NO: 6). Alternatively, the tag sequence may be $X_{14}$-$Y_6$ or $X_{14}$-$Y_{16}$ comprising $(Lys)_{16}$-$(Glu)_4$ (SEQ ID NO: 7) or $(Lys)_4$-$(Glu)_{16}$ (SEQ ID NO: 8). In a non-limiting example, the peptide tag is comprised of 20 amino acids and the charge ratio is 1.5:1, e.g., $(Lys)_{12}(Glu)_8$ (SEQ ID NO: 9); X or Y may occur as blocks, e.g., $(Lys)_{12}$-$(Glu)_8$ (SEQ ID NO: 9) or may be alternating, e.g, Lys-Lys-Glu-Lys-Lys-Glu-Lys-Lys-Glu-Lys-Lys-Glu-Lys-Lys (SEQ ID NO: 10), or random, e.g., Glu-Lys-Lys-Lys-Lys-Lys-Glu-Glu-Lys-Glu-Lys-Lys-Lys-Lys-Lys-Lys (SEQ ID NO: 11).

(4) Peptide Antigen Conjugates Induced to Form Particles Through Electrostatic Interactions and Stabilized by Pi Orbital Stacking Minimal CD4 and CD8 T cell epitopes can be delivered as the minimal epitope linked to a peptide tag sequence comprised of charged amino acids connected through an optional linker. The charged residues flanking the antigen can be used to drive particle formation through electrostatic interactions. Aromatic amino acids can be used to further stabilize the interactions of peptides through Pi orbital stacking and hydrophobic interactions.

Example peptide antigen conjugate: $A_{8-12}$-B-$(X_l$-$Y_m$-$Z_n)$

Tag sequences for this construct are preferably between 22-25 amino acids in length, with between a 1.2:1 to a 6:1 molar excess of either X or Y and between 2-5 aromatic residues. In a non-limiting example the tag sequence may be $X_{15}$-$Y_5$-$Z_2$. In some embodiments, the tag sequence can be $(Lys)_{16}$-$(Glu)_4$-$(Trp)_2$ (SEQ ID NO: 12) or $(Lys)_4$-$(Glu)_{16}$-$(Trp)_2$ (SEQ ID NO: 13). X, Y and Z comprising the peptide tag may occur as blocks in the sequence, or they may alternate or be randomly distributed along the sequence.

For the delivery of neoantigens with poorly defined epitopes, an exemplary embodiment is a 29-35 amino acid peptide-based neoantigen defined by the 14-17 N- and C-terminal amino acids on each side of the mutant amino acid (i.e., defining the variant allele of the neoantigen, which defines the mutation) that is linked to a peptide tag sequence comprised of charged amino acids connected through an optional linker. Note that 29-35 amino acid peptide neoantigen sequences preferably contain all of the CD4 and CD8 T cell epitopes for a given peptide neoantigen. The charged residues flanking the antigen can be used to drive particle formation through electrostatic interactions.

Aromatic amino acids can be used to further stabilize the interactions of peptides through Pi orbital stacking and hydrophobic interactions.

Example peptide antigen conjugate: $A_{12-40}$-B-$(X_l$-$Y_m$-$Z_n)$

Peptide Tag sequences for this construct are preferably no more than 22-25 amino acids in length, with between a 4:1 to a 6:1 molar excess of either X or Y and between 2-5 aromatic residues. In a non-limiting example the Peptide Tag sequence may be $X_{15}$-$Y_5$-$Z_2$. In some embodiments, the Peptide Tag sequence can be $(Lys)_{16}$-$(Glu)_4$-$(Trp)_2$ (SEQ ID NO: 12) or $(Lys)_4$-$(Glu)_{16}$-$(Trp)_2$ (SEQ ID NO: 13).

(5) Co-Delivery of Peptide Antigen Conjugate with an Innate Immune Stimulus (e.g., TLR Agonist).

Immunostimulants, such as TLR agonists can be admixed with the peptide antigens that form nanoparticle polyplexes, described above, or the TLR agonists can be directly linked to either peptides or polymers that complex with the peptide antigen conjugate to form nanoparticle polyplexes. The advantage of linking the adjuvant, such as a TLR agonist, to a peptide or polymer that is incorporated into the polyplex through electrostatic interactions is that it ensures co-delivery of the antigen with an innate immune stimulus, thereby preventing tolerance that can occur when an antigen is delivered to an immune cell without adequate innate immune stimulation.

A exemplary embodiment is for a small molecule TLR-7/8a to be linked directly to the C-terminus of the peptide through an amide bond or through the side chains of amino acids comprising the amino acids flanking the antigens at the C-terminus.

Example peptide antigen conjugates co-delivering an adjuvant include:

$A_{8-40}$-B-$X_l$-(Adjuvant), wherein the adjuvant is linked at the C-terminus of the peptide antigen conjugate $A_{8-40}$-B-$Y_m$-(Adjuvant), wherein the adjuvant is linked at the C-terminus of the peptide antigen conjugate $A_{8-40}$-B-$(X_l$-$Y_n)$-(Adjuvant), wherein the adjuvant is linked at the C-terminus of the peptide antigen conjugate $A_{8-40}$-B-$(X_l$-$Y_m$-$Z_n)$-(Adjuvant), wherein the adjuvant is linked at the C-terminus of the peptide antigen conjugate $A_{8-40}$-B-(Amino acid-(Adjuvant) conjugate)$_n$, wherein the adjuvant is linked to amino acid side chains that comprise the peptide antigen conjugate.

Or the adjuvant may be complexed with the peptide antigen conjugate through electrostatic interactions. Example constructs include:

$A_{8-40}$-B-$X_l$+(Adjuvant)-B-$Y_m$ $A_{8-40}$-B-$Y_m$+(Adjuvant)-B-$X_l$ $A_{8-40}$-B-$(X_l$-$Y_m)$+(Adjuvant)-B-$X_l$-$Y_m$ $A_{8-40}$-B-$(X_l$-$Y_m$-$Z_n)$+(Adjuvant)-B-$X_l$-$Y_m$-Z In some embodiments the adjuvant is a polymer, such as a nucleic acid sequence, such as CpG or p(I:C) that can be complexed with the peptide antigen conjugate.

The adjuvant in any of the described embodiments can be a TLR-7/8 agonist, such as an imidazoquinoline-based TLR-7/8 agonist.

The above constructs are based on the unexpected findings that attachment of a TLR-7/8a to long peptides promotes particle formation and that particle formation together with co-delivery of TLR-7/8a leads to enhanced T cell responses. Peptide Tag sequences for these constructs are preferably no more than 20-25 amino acids in length. For construct with X and Y, charge ratio are preferably between 1.2:1 to 6:1. For constructs with X, Y and Z, Z preferably comprise between 2-5 amino acids.

Charge Ratio Considerations for Peptide Antigen Conjugates

The peptide antigen conjugates disclosed herein carry either a net positive or net negative charge at physiologic pH and assemble into nanoparticle complexes through electrostatic interactions. An optimal charge ratio, i.e. the ratio between the molar amount of positive and negatively charged residues, comprising the nanoparticle complex is preferably selected to (1) ensure stable nanoparticle formations occurs; and, (2) that the particles are of an optimal size, typically between 20-200 nm in diameter to promote uptake by dendritic cells. The data presented in the examples indicate that the optimal charge ratio depends on the nature of the peptide antigen conjugate and polymers used to form the nanoparticle polyplex.

In some embodiments, the peptide antigen conjugate has a net negative charge.

Charge ratios of from about 5:1 to about 2:1, or from about 1:10 to about 1:20 (positive to negative, molar charge ratio) are preferred for the formation of stable electrostatic complexes formed between net negatively charged peptide antigen conjugates and poly(cationic) poly(lysine)-based polymers to ensure formation of stable nanoparticles of between 20-200 nm that promote high magnitude T cell responses.

Charge ratios of from about 1:5 to about 1:10 (positive to negative, molar charge ratio) are preferred for the formation of stable electrostatic complexes formed between net negatively charged peptide antigen conjugates and poly(cationic) PEI-based polymers to ensure formation of stable nanoparticles of between 20-200 nm that promote high magnitude T cell responses.

Charge ratios of from about 1:10 to about 1:20 (positive to negative, molar charge ratio) are preferred for the formation of stable electrostatic complexes formed between net negatively charged peptide antigen conjugates and positively charged peptide antigen conjugates to ensure formation of stable nanoparticles of between 20-200 nm that promote high magnitude T cell responses.

Charge ratios of from about 1:5 to about 1:10 (such as about 1:5), or about 2:1 (positive to negative, molar charge ratio) are preferred for the formation of stable electrostatic complexes formed between net negatively charged peptide antigen conjugates co-complexed with a poly(anionic) polysaccharide, sodium alginate and poly(cationic) polymers, such as poly(lysine) and PEI-based polymers to ensure formation of stable nanoparticles of between 20-200 nm that promote high magnitude T cell responses.

In some embodiments, the peptide antigen conjugate has a net positive charge.

Charge ratios of from about 1:2 to about 1:10 (positive to negative, molar charge ratio) are preferred for the formation of stable electrostatic complexes formed between net positively charged peptide antigen conjugates and poly(anionic) polymers based on either alginate or poly(glutamic acid) to ensure formation of stable nanoparticles of between 20-200 nm that promote high magnitude T cell responses.

Charge ratios of about 1:20 (positive to negative, molar charge ratio) are preferred for the formation of stable electrostatic complexes formed between net positively charged peptide antigen conjugates and poly(anionic) polymers based on nucleic acid sequences or poly(acrylic acids) to ensure formation of stable nanoparticles of between 20-200 nm that promote high magnitude T cell responses.

Charge ratios of from about 2:1 to about 1:10 (such as about 2:1, about 1:5, or about 1:10) (positive to negative, molar charge ratio) are preferred for the formation of stable electrostatic complexes formed between net positively charged peptide antigen conjugates co-complexed with a poly(anionic) polysaccharide, sodium alginate and poly(cationic) based polymers such as PEI or poly(lysine) to ensure formation of stable nanoparticles of between 20-200 nm that promote high magnitude T cell responses.

Note that the use of Alginate increases the range of suitable charge ratios that can be used for polyelectrolyte complexes formed between positively charged peptide antigen conjugates and poly(anionic) polymers.

Charge of amino acids and polymers is based on the estimated protonation state of basic and acidic amino acid residues at physiologic pH (7.4). For example, the epsilon amine of Lysine has a pKa of ~10.7 and is predicted to carry a positive charge (NH3+) at pH 7.4, whereas the gamma carboxylic acid of Glutamic acid has a pKa of 4.15 and is predicted to be negatively charged at pH 7.4; however, some cations and anions carry a charge independent of pH, such as tetra-alkylammonium, which has a permanent positive charge.

Peptide antigen conjugates of formula $A_{8-40}$-B-$X_l$-$Y_m$ or $A_{8-40}$-B-$X_l$-$Y_m$-$Z_n$ conjugate (that is, a conjugate not linked to a polymer) preferably provide a charge ratio of between 1.2:1 and 6:1. Exemplary peptide tags sequences for inclusion with provide 2.3:1 ratio of X:Y residues (e.g., $A_{8-40}$-B-Lys-Lys-Lys-Lys-Lys-Lys-Lys-Glu-Glu-Glu, SEQ ID NO: 14) or a 1:2.3 ratio of Y:X residues (e.g., $A_{8-40}$-B-(Glu)$_7$-(Lys)$_3$, SEQ ID NO: 15). The peptide can be constructed such that the positive residues precede the negatively charge residues, or the negatively charged residues can precede the positively charged residues in the sequence. Arginine and tetramethylysine residues can be used in place of Lysine, and Aspartic acid can be used in place of glutamic acid.

For the electrostatic complexation of peptides to charged polymers, a single charge (positive or negative) preferably predominates the peptide to be used to electrostatically complex with polymers with the opposing charge. For example, peptides constructs such as $A_{12-40}$-B-$X_l$ or $A_{12-40}$-B-$Y_m$ are preferably used to complex poly(anionic) and poly(cationic) polymers, respectively. In several embodiments, the number of charged residues (for example, present on the peptide tag) of the conjugate preferably is 5-15. In some embodiments, the number of charged residues (for example, present on the peptide tag) of the conjugate can be 10 charged. The optimal charge ratios for nanoparticles polyplexe formed between peptide antigen conjugates and polymers of opposite charge are described above and exemplified in the examples section.

Use of Aromatic Amino Acids to Promote Pi Orbital Stacking and Hydrophobic Interactions of Peptide Antigen Conjugates Particle formed by electrostatic interactions can be further stabilized by the inclusion of aromatic groups on the peptides and polymers.

In some embodiments, peptide antigen conjugates are designed to self-assemble into particles without polymer (i.e. constructs with the formula: $A_{8-40}$-B-$X_l$-$Y_m$-$Z_n$); from 1-5 (such as 1) aromatic groups (such as a tryptophan residue) can be included on the conjugate to promote Pi orbital stacking that stabilized the particles formed through electrostatic interactions. In some embodiments, for conjugates are designed to self-assemble into particles without polymer (i.e., constructs with the formula: $A_{8-40}$-B-$X_l$-$Y_m$-$Z_n$), 2 tryptophan residues can be included at the C-terminus of the peptide tag included in the conjugate to promote Pi orbital stacking that stabilizes the particles formed through electrostatic interactions. In some embodiments, phenylalanine, benzyl glutamate or tyrosine residues can be used in place of the tryptophan residue(s).

In some embodiments, an adjuvant (e.g., a TLR-7/8 agonist) can be attached to amino acids either N- or C-terminal relative to the aromatic amino acid residues (e.g., Example construct: $A_{12\text{-}40}$-B-$X_l$-$Y_m$-TLR-7/8a-$Z_n$ or $A_{12\text{-}40}$-B-$X_l$-$Y_m$-$Z_n$-TLR-7/8a).

Peptides that alone use aromatic residues to promote particle formation are not preferred as this will lead to highly insoluble peptides that will form uncontrolled aggregation due to low charge density on the surfaces of the formed particles. In contrast, combining both electrostatic interactions and aromatic residues is a novel construct that provides particles with high charge density on the surfaces of particles that are internally stabilized by Pi orbital stacking and hydrophobic interactions. It is notable that the TLR-7/8a on the peptides will further contribute to the stabilization through Pi orbital stacking.

For schemes in which charged peptides are combined with charged polymers, aromatic groups can be placed on either or both the peptide and polymer to stabilize the formed particles. The aromatic groups on the polymer can be the pendantly arrayed adjuvant (e.g., a TLR-7/8 agonist) attached to poly(anionic) or poly(cationic) polymers or they may be immunologically neutral side chains, such as benzyl, napthyl or other fused or heterocyclic ring structures.

Peptide Antigen Sequences

Peptide antigens can be derived from tumor-associated self-antigens or neoantigens. Suitable tumor-associated self-antigens are preferentially expressed by tumor cells but can also be expressed by healthy cells. Alternatively, the peptide antigen can be a neoantigen, which are aberrant proteins, the compositions of which are unique to individual patients.

The process for identifying neoantigens for delivery as peptide-based vaccines involves DNA and RNA sequencing of patient tumor biopsies followed by bio-informatics to identify neoantigens, which are classified as mutations in protein-coding DNA that are expressed as RNA and produce peptides predicted to bind to MHC-I alleles on patient antigen presenting cells (APCs). Neoantigens for use in individualized vaccination schemes are selected based on predicted MHC-I binding and expression levels within tumors, which together suggest that a given neoantigen can be efficiently presented by tumor cells to T cells. For patients with greater than 20 neoantigens, a down-selection process can be used to select peptides predicted to have the highest MHC-I affinity and highest read count or RNA expression levels. For patients with less than 20 predicted neoantigens, a down selection process is not critical.

Peptides comprising the neoantigen preferably encompass the single nucleotide polymorphism arising from a missense mutation or novel chimeric sequence arising from frameshift mutations that create novel sequences of amino acids that are not present in non-cancerous cells derived from the same patient. The peptide-based neoantigen sequence preferably comprise the 10-20 amino acids on both sides flanking the single nucleotide polymorphism or novel junction created by missense and frameshift mutations, respectively. These peptides will be 21-41 amino acids in length and preferably contain all possible CD8 and CD4 T cell epitopes arising from the mutant protein. In some embodiments, two or more (such as 2-10, 2-5, 2, 3, 4, 5, 6, 7, 8, or 10) different peptide antigens can be included on the peptide linked to the polymer. In additional embodiments, several copies (such as two, three, four, five or more copies) of the same peptide antigen can be included on the peptide linked to the polymer. In examples where multiple peptide antigens are included on the peptide linked to the polymer, the peptide antigens can be contiguous or separated by peptide linkers.

In some embodiments, the peptide antigen is an antigen from an infectious agent, such as virus, a bacteria, or a fungus.

Non-limiting examples of infectious viruses include: Retroviridae (for example, human immunodeficiency viruses, such as HIV-1; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses, such as MERS, SARs, etc); Arboviruses (eastern equine, western equine, St. Louis, Venezuelan equine encephalitis, and West Nile viruses); Epstein-Barr virus; Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses).

In some embodiments, the peptide antigen comprises an antigen from a human immunodeficiency virus protein, such as a HIV-1 gag p41 protein, a HIV-1 gp120 protein, a HIV-1 gp41 protein, HIV-1 gp140, HIV-1 gp145, or a HIV-1 Env protein. In some embodiments, the peptide antigen comprises an antigen from an influenza protein, such as a hemagglutinin protein or a neuraminidase protein. In some embodiments, the peptide antigen comprises an antigen from an Ebolavirus protein, such as a GP protein.

In some embodiments, the peptide antigen comprises an antigen from an infectious bacterial protein. Non-limiting examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., Enterococci, *Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Pseudomonas aeruginosa, Clositridium difficilie, Streptobacillus moniliformis, Treponema pallidium, Treponema pertenue*, Leptospira, and *Actinomyces israelli.*

In some embodiments the peptide antigen comprises an antigen from a *Mycobacterium tuberculosis* protein, such as an ESAT-6 protein or a 85B protein.

In some embodiments, the peptide antigen comprises an antigen from an infectious fungi protein. Non-limiting examples of infectious fungi include, but are not limited to, *Cryptococcus neoformans, Histoplasma capsulatum, Coccidioides immitis, Blastomyces dermatitidis, Chlamydia trachomatis,* and *Candida albicans.*

Other infectious agents include *Plasmodium falciparum, Plasmodium vivax, Leishmania major, Trypanosoma cruzi, Giardia lablia,* and *Toxoplasma gondii.*

In additional embodiments, the antigen is a toxin or immunogenic portion thereof, such as a protein-based toxins produced by bacteria, such as Anthrax and Tetanus toxins. In additional embodiments, the antigen is a toxin or immunogenic portion thereof, such as a manmade toxin or drug of abuse, such as protein toxins (ricin).

In additional embodiments, the peptide antigen comprises a tumor associated antigen. For example, the antigen can be a conserved cancer-associated self-antigen, such as NYESO1 (testicular cancer), Na17 (melanoma), gp100 (melanoma). In additional embodiments, the antigen is a neoantigen that is a mutated self-protein that can be unique to a particular tumor or cancer from a particular individual.

In some embodiments, the antigen can be from a hematological tumor. Non-limiting examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the antigen can be from a solid tumor. Non-limiting examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

In some embodiments, the tumor associated antigen is from a breast cancer, such as a ductal carcinoma or a lobular carcinoma. In some embodiments, the tumor associated antigen is from a prostate cancer. In some embodiments, the tumor associated antigen is from a skin cancer, such as a basal cell carcinoma, a squamous cell carcinoma, a Kaposi's sarcoma, or a melanoma. In some embodiments, the tumor associated antigen is from a lung cancer, such as an adenocarcinoma, a bronchiolaveolar carcinoma, a large cell carcinoma, or a small cell carcinoma. In some embodiments, the tumor associated antigen is from a brain cancer, such as a glioblastoma or a meningioma. In some embodiments, the tumor associated antigen is from a colon cancer. In some embodiments, the tumor associated antigen is from a liver cancer, such as a hepatocellular carcinoma. In some embodiments, the tumor associated antigen is from a pancreatic cancer. In some embodiments, the tumor associated antigen is from a kidney cancer, such as a renal cell carcinoma. In some embodiments, the tumor associated antigen is from a testicular cancer.

Nanoparticles and Polymer Nanoparticles

The conjugate comprising the peptide antigen can be included in a nanoparticle. For example, the conjugate or the conjugate linked to the polymer can form polymer nanoparticles in phosphate buffered saline, pH 7.4 that can be taken up into a cell (such as an immune cell, for example, an antigen presenting cell). An appropriate adjuvant can be incorporated in the nanoparticles by pendantly arraying the adjuvant on the polymer (in the case of polymer nanoparticles), or by admixing the adjuvant with the conjugate or the conjugate linked to a polymer. The nanoparticles are of a size that can be taken up into the endosomal system of cells (such as immune cells). In a population of such nanoparticles the nanoparticles can be all of the same type (e.g., the same size, or including the same peptide antigen) or the nanoparticles can be made up of two or more different types (e.g., including varying sizes, or including peptide antigens) in any combination and in any ratio. The nanoparticles can be in an average size range of about 20 nm to about 1000 nm in diameter, such as about 50 nm to about 1000 nm in diameter. Thus, the nanoparticles can have an average diameter about 50 nm, about 50 nm, about 75 nm, about 100 nm, about 150 nm, about 200 nm, about 250 nm, about 300 nm, about 400 nm, about 500 nm, about 750 nm, about 1000 nm, or can have an average diameter range of about 50 nm to about 500 nm, from about 100 nm to about 500 nm, from about 100 nm to about 750 nm, from about 100 nm to about 1000 nm, from about 250 nm to about 750 nm, from about 500 nm to about 1000 nm, from about 250 nm to about 500 nm. The nanoparticles in the composition can vary in size, but will generally fall within the size range set forth herein. In some embodiments, the nanoparticles may be included in larger particle structures, including those that are too large for uptake by immune cells (e.g., particles larger than about 5000 nm) and that slowly release the nanoparticles including the peptide antigen as a function of their degradation.

Methods of generating nanoparticles from soluble polymer coils complexed with peptides are known (see, e.g., Green, J. J. et al. Electrostatic ligand coatings of nanoparticles enable ligand-specific gene delivery to human primary cells. *Nano letters* 7, 874-879 (2007); Kang, S. et al. Virus-mimetic polyplex particles for systemic and inflammation-specific targeted delivery of large genetic contents. *Gene Ther* 20, 1042-1052 (2013); Kim, S. W. Polylysine copolymers for gene delivery. *Cold Spring Harbor protocols* 2012, 433-438 (2012)). In a non-limiting example, dynamic light scattering or electron microscopy can be used to evaluate nanoparticle size.

Polymers

Polymers can form a complex with peptide antigens (e.g., by electrostatic interaction and pi orbital stacking), and can form polymer nanoparticles that can be administrated to a subject without causing toxic side effects. Any appropriate polymer can be used. The polymer can be a statistical copolymer or alternating copolymer. The polymer can be a block copolymer, such as the A-B type, or the polymer can be comprised of a grafted copolymer, whereby two polymers are linked through polymer analogous reactions.

The polymer may include naturally occurring and synthetic monomers and combinations thereof. Natural biopolymers may include single or double stranded RNA or DNA, comprised of nucleotides (e.g., adenosine, thymidine). The natural biopolymers can be peptides comprised of amino acids; a specific example is poly(lysine). Biopolymers can be polysaccharides, which may include but are not limited to glycogen, cellulose and dextran. Additional examples include polysaccharides that occur in nature, including alginate and chitosan. Polymers may also be comprised of naturally occurring small molecules, such as lactic acid or glycolic acid, or may be a copolymer of the two (i.e., PLGA). Suitable preformed particles may also be based on formulations (e.g., stabilized emulsions, liposomes and polymersomes) or may be mineral salts that form particles suitable for complexation or ion exchange on the surfaces of the particles, which may include aluminum-based salts.

In some embodiments, the polymer can be an anionic (e.g., poly(acidic)) polymer or cationic (e.g., poly(basic)) polymer. Cationic polymers can bind to negatively charged peptides by electrostatic interaction. In some embodiments, the cationic polymer can be a naturally occurring or synthetic poly(amine), such as poly(lysine) or poly(ethylenimine) (PEI). In additional embodiments, the cationic polymer can be a poly(amido amine) (PAA) or poly(beta amino ester) (PBAE) produced from the Michael addition reaction of amines with either bis(acrylamides) or bis(acrylesters). Non-limiting examples of cationic polymers that can be used in the disclosed embodiments include poly(ethylenimine), poly(allylanion hydrochloride; PAH), putrescine, cadaverine, poly(lysine) (PL), poly(arginine), poly(trimethylenimine), poly(tetramethylenimine), poly(propylenimine), aminoglycoside-polyamine, dideoxy-diamino-b-cyclodextrin, spermine, spermidine, cadaverine, poly(2-dimethylamino)ethyl methacrylate, poly(histidine), cationized gelatin, dendrimers, chitosan, and any combination thereof. The cationic polymer may contain a quaternary ammonium group, such as that present on methylated chitosan. The adjuvant (e.g., TLR-7/8a) can be linked to the polymer through one of the various aforementioned linker groups. The polycation polymer (e.g., PEI or PL) can be complexed with the antigen via physical electrostatic force (e.g., wherein the negative charges in the antigen can bind with the positive charges in the poly(cation).

Anionic polymers can bind to positively charged peptides by electrostatic interaction. In some non-limiting examples, the polyanionic polymer is poly(glutamic acid). In alternative embodiments, the polyanionic polymer is poly(aspartic acid). The polymer can be a polyphosphoester-based polymer. The polymer may comprise natural anionic polysaccharides, including, e.g., alginic acid, comprised of (1-4)-linked β-D-mannuronate and guluronic acid. Other polyanionic polymers may be equally suited.

In some embodiments, the polymer can be a poly(diethylene glycol methacrylate)-based polymer.

In additional embodiments, the polymer may include monomers of (meth)acrylates, (meth)acrylamides, styryl and vinyl moieties. Specific examples of (meth)acrylates, (meth) acrylamides, as well as styryl- and vinyl-based monomers include N-2-hydroxypropyl(methacrylamide) (HPMA), hydroxyethyl(methacrylate) (HEMA), styrene and vinylpyrrolidone (PVP), respectively. The polymer can be a thermoresponsive polymer comprised of monomers of N-isopropylacrylamide (NIPAAm); N-isopropylmethacrylamide (NIPMAm); N,N'-diethylacrylamide (DEAAm); N-(L)-(1-hydroxymethyl)propyl methacrylamide (HMPMAm); N,N'-dimethylethylmethacrylate (DMEMA), or 2-(2-methoxyethoxy)ethyl methacrylate (DEGMA). Polymers can also be based on cyclic monomers that include cyclic urethanes, cyclic ethers, cyclic amides, cyclic esters, cyclic anhydrides, cyclic sulfides and cyclic amines.

Polymers based on cyclic monomers may be produced by ring opening polymerization and include polyesters, polyethers, polyamines, polycarbonates, polyamides, polyurethanes and polyphosphates; specific examples may include but are not limited to polycaprolactone and poly(ethylenimine) (PEI). Suitable polymers may also be produced through condensation reactions and include polyamides, polyacetals and polyesters.

The polymers included in the peptide-based antigen delivery platform include a plurality of monomer units. In some embodiments, the polymer can include from 3 to 10000 monomer units, such as from 3 to 500 monomer units, from 3 to 100 monomer units, from 3 to 50 monomer units, from 3 to 10 monomer units, from 5 to 1000 monomer units, such as from 5 to 500 monomer units, from 5 to 100 monomer units, from 5 to 50 monomer units, from 5 to 10 monomer units, from 500 to 1000 monomer units, from 100 to 500 monomer units, from 250 to 500 monomer units, from 300 to 600 monomer units, or from 100 to 250 monomer units. Typically at least five monomers are needed to sufficiently complex the negatively charged antigen. In embodiments including a cationic polymer, increasing the number of monomer units (degree of polymerization) increases the strength of the interaction of the positively/negatively charged polymer and negatively/positively charged antigen. In some embodiments, the average molecular weight of the polymer may be between about 5,000 to 1,000,000 g/mol. The polydispersity indexes of the polymer may range from about 1.05 to about 5.0.

In several embodiments, the monomers of the polymer include a sidechain including at least one functional group that can be coupled to the adjuvant, or to a linker that can be coupled to the adjuvant. However, typically not all of the monomers in the polymer are linked to the adjuvant. For example, the ratio of adjuvant to monomer of the polymer can be from 1:100 to 1:1 mol/mol, such as from 1:20 to 1:10 mol/mol. In some embodiments, the ratio can be 1:20 as this imparts minimal effects on the overall physical and chemical properties of the polymer used to complex the antigen. Typically, the delivery platform includes a sufficiently high density of the adjuvant to enhance an immune response without impacting the ability of the polymer to complex with peptide antigen and form polymer nanoparticles in phosphate buffered saline, pH 7.4.

Linkers

The adjuvant can be linked to the polymer or conjugate by any suitable means. Both covalent and non-covalent attachment means may be used. The procedure for linking the adjuvant to the polymer or conjugate varies according to the chemical structure of the adjuvant and the polymer or conjugate. The linker can be any molecule used to link the polymer or conjugate to the adjuvant. Typically, the linker is capable of forming covalent bonds to both the polymer or conjugate and the adjuvant. Suitable linkers are well known to those of skill in the art and include, but are not limited to, straight or branched-chain carbon linkers, heterocyclic carbon linkers, peptide linkers, or a combination thereof. In some embodiments, the carbon linker can include a C1-C18 alkane linker. The linker molecule may comprise a hydrophilic or hydrophobic linker. In several embodiments, the linker includes a peptide that is cleavable by an intracellular enzyme (such as a cathepsin).

In some embodiments, the linker may comprise one or more PEG moieties. The linker, such as PEG, may be at least 2 monomers in length. The linker, such as PEG, may be between about 4 and about 24 monomers in length, or more. In some embodiments, where the linker comprises a carbon chain, the linker may comprise a chain of between about 1 or 2 and about 18 carbons. In some embodiments, where the linker comprises a carbon chain, the linker may comprise a chain of between about 12 and about 20 carbons. In some embodiments, where the linker comprises a carbon chain, the linker may comprise a chain of between no more than 18 carbons.

The linker may be linked to the polymer or conjugate by any suitable chemical moiety, for example any moiety resulting from a 'click chemistry' reaction, or thiol exchange chemistry. For example, a triazole group may attach the linker to the polymer or conjugate. An alkyne group and an azide group may be provided on respective molecules to be linked by "click chemistry". For example the PRR agonist may comprise, or be modified with, an N-terminal azide that allows for coupling to a polymer or conjugate having an appropriate reactive group such as an alkyne group. The skilled person will understand that there are a number of suitable reactions available to link the linking group to the polymer or conjugate. In one embodiment, the linker may be linked to the polymer backbone of the polymer by an amine. The link with an amine may be provided by reacting any suitable electrophilic group such as alkenes (via Michael addition), activated esters (for example, NHS ester), aldehydes, and ketones (via Schiff base). The adjuvant may be linked to the polymer or conjugate using split intein or SpyTag or other enzymatic ligase strategies.

In some embodiments, the linker may be a poly(basic) or poly(acidic) molecule that carries a positive or negative charge, respectively. The poly(basic) linker that can be electrostatically complexed to a poly(acidic) polymer or conjugate through charge neutralization. The poly(acidic) linker can be electrostatically complexed to a poly(basic) polymer or conjugate. The positive charge can be non-basic in origin and may result from a quaternary amine.

In some embodiments, the linker is cleavable under intracellular conditions, such that cleavage of the linker releases the adjuvant from the polymer in the intracellular environment.

For example, the linker can be cleavable by an enzyme that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease (such as a cathepsin). In some embodiments, the peptide linker is at least two amino acids long or at least three amino acids long. However, the linker can be 2, 3, 4, 5, 6, 7, 8, 9, 10, 11, 12, 13, 14 or 15, or more (such as up to 30) amino acids long, such as 2-5, 3-10, 3-15, 2-5, 2-10, 2-15, or more amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

Particular sequences for the cleavable peptide in the linker can be used to control the rate of cleavage of the linker. For tetrapeptide linkers (including four amino acids), for rapid cleavage, preferred amino acids at the P1 position of the tetrapeptide are K, R, Q, T, L, N (Norleucine), or M. For slow release, preferred amino acids at the P1 position of the tetrapeptide are H, D, E, G, P, F, A, V or I. In some embodiments, use of D amino acids in the linker provides another means of slowing the rate of hydrolysis. In some embodiments, the linker can include a cathepsin-cleavable peptide comprising L-amino acids or D-amino acids comprising the amino acid sequence set forth as one of: GFLG (SEQ ID NO: 16), KPLR (SEQ ID NO: 17), KLRP (SEQ ID NO: 18), SLVR (SEQ ID NO: 19), or SLRV (SEQ ID NO: 20).

In other embodiments, the cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In some embodiments, the linker can include a spacer element, which, when present, increases the size of the linker such that the distance between the polymer and the adjuvant is increased. Exemplary spacers are known to the person of ordinary skill, and include those listed in U.S. Pat. Nos. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Patent Publication Nos. 20110212088 and 20110070248, each of which is incorporated by reference in its entirety.

Adjuvants

The adjuvant linked to the polymer or conjugate may be, or be derived from, any suitable adjuvant compound. Suitable adjuvant compounds include small organic molecules, i.e., molecules having a molecular weight of less than about 3000 Daltons, although in some embodiments the adjuvant may have a molecular weight of less than about 700 Daltons and in some cases the adjuvant may have a molecular weight from about 500 Daltons to about 700 Daltons.

The density of the adjuvant included linked to the polymer or conjugate can be varied as needed for particular applications. For example, the adjuvant may be linked to the monomer units (such as co-monomer units) of the polymer or conjugate at a density of from 1 to 100 mol %, such as from 1 to 10 mol %, from 5 to 10 mol %, from 1 to 5 mol % of the polymer, from 5 to 15 mol %, from 10 to 20 mol %, from 10 to 15 mol %, from 7 to 13 mol %, from 8 to 10 mol %, from 1 to 25 mol %, from 5 to 25 mol %, from 10 to 25 mol %. The mol % of the adjuvant refers to the molar percentage of monomer units bearing the adjuvant incorporated to the polymer chain or conjugate. For example, 10 mol % adjuvant is equal to 10 monomer units linked to the adjuvant molecules from a total 100 monomer units. The remaining 90 may be macromolecule-forming monomeric units.

In some embodiments, the density of the attached to the polymer or conjugate can be from 1 to 3 mol %, from 2 to 4 mol %, from 3 to 5 mol %, from 4 to 6 mol %, from 5 to 7 mol %, from 6 to 8 mol %, from 7 to 9 mol %, from 8 to 10 mol %, from 9 to 11 mol %, from 10 to 12 mol %, from 11 to 13 mol %, from 12 to 14 mol %, from 13 to 15 mol %, from 14 to 16 mol %, from 15 to 17 mol %, from 16 to 18 mol %, from 17 to 19 mol %, from 18 to 20 mol %, from 20 to 22 mol %, from 21 to 23 mol %, from 22 to 24 mol % from 23 to 25 mol %.

In some embodiments, the density of the adjuvant attached to the polymer or conjugate can be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%.

In several embodiments, the adjuvant can be a pattern recognition receptor agonist. Non-limiting examples of pattern recognition receptor agonists include TLR-1/2/6 agonists (e.g., lipopeptides and glycolipids, such as Pam2cys or Pam3cys lipopeptides); TLR-3 agonists (e.g., dsRNA, such as PolyI:C, and nucleotide base analogs); TLR-4 agonist (e.g., lipopolysaccharide (LPS) derivatives and small molecule analogs of pyrimidoindole); TLR5 agonists (e.g., Flagellin); TLR-7/8 agonists (e.g., ssRNA and nucleotide base analogs, including derivatives of imidazoquinolines, hydroxy-adenine, benzonapthyridine and loxoribine); and TLR-9 agonists (e.g., unmethylated CpG); Stimulator of Interferon Genes (STING) agonists (e.g., cyclic dinucleotides, such as cyclic diadenylate monophosphate); C-type lectin receptor (CLR) agonists (such as various mono, di, tri and polymeric sugars that can be linear or branched, e.g., mannose, Lewis-X tri-saccharides, etc.); RIG-I-like receptor (RLR) agonists; and NOD-like receptor (NLR) agonists (such as peptidogylcans and structural motifs from bacteria, e.g., meso-diaminopimelic acid and muramyl dipeptide); and combinations thereof. In several embodiments, the pattern recognition receptor agonist can be a TLR agonist, such as an imidazoquinoline-based TLR-7/8 agonist. For example, the adjuvant can be Imiquimod (R837) or Resiquimod (R848), which are approved by the FDA for human use.

In several embodiments, the adjuvant can be a TLR-7 agonist, a TLR-8 agonist and/or a TLR-7/8 agonist. Numerous such agonists are known, including many different imidazoquinoline compounds.

Imidazoquinolines are of use in the methods disclosed herein. Imidazoquinolines are synthetic immunomodulatory drugs that act by binding Toll-like receptors 7 and 8 (TLR-7/TLR-8) on antigen presenting cells (e.g., dendritic cells), structurally mimicking these receptors' natural ligand, viral single-stranded RNA. Imidazoquinolines are heterocyclic compounds comprising a fused quinoline-imidazole skeleton. Derivatives, salts (including hydrates, solvates, and N-oxides), and prodrugs thereof also are contemplated by the present disclosure. Particular imidazoquinoline compounds are known in the art, see for example, U.S. Pat. Nos. 6,518,265; and 4,689,338. In some non-limiting embodiments, the imidazoquinoline compound is not imiquimod and/or is not resiquimod.

In some embodiments, the adjuvant can be a small molecule adjuvant having a 2-aminopyridine fused to a five membered nitrogen-containing heterocyclic ring, and include but are not limited to imidazoquinoline amines, including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Additional Embodiments

Clause 1. An immunogenic composition for inducing an immune response to a peptide antigen in a subject, the immunogenic composition comprising nanoparticles, the nanoparticles comprising:
a conjugate comprising the peptide antigen linked to a peptide tag; and
an adjuvant; and
wherein
the conjugate comprises a net negative or a net positive charge at pH 7.4;
the peptide tag comprises a ratio of positively charged amino acids to negatively charged amino acids of from 4:1 to 6:1 if the conjugate comprises the net positive charge;
the peptide tag comprises a ratio of negatively charged amino acids to positively charged amino acids of from 4:1 to 6:1 if the conjugate comprises the net negative charge;
the nanoparticles enter immune cells under physiological conditions to induce the immune response to the peptide antigen in the subject.

Clause 2. The immunogenic composition of claim 1, wherein the peptide antigen is a soluble peptide antigen, particularly wherein a peptide consisting of the peptide antigen dissolves to at least 0.1 mg/ml in phosphate buffered saline, pH 7.4 at room temperature.

Clause 3. The immunogenic composition of clause 1 or 2, wherein the peptide antigen is linked to the peptide tag by a linker.

Clause 4. The immunogenic composition of any one of the prior clauses, wherein the linker is a cathepsin-cleavable peptide linker.

Clause 5. The immunogenic composition of any one of the prior clauses, wherein the peptide tag comprises from 1 to 5 aromatic amino acids.

Clause 6. The immunogenic composition of clause 5, wherein the peptide antigen and the peptide tag together comprise a single aromatic amino acid.

Clause 7. The immunogenic composition of clause 5 or 6, wherein the aromatic amino acid is tryptophan.

Clause 8. The immunogenic composition of any one of the prior clauses, wherein the peptide antigen is no more than 50 amino acids in length.

Clause 9. The immunogenic composition of clause 8, wherein the peptide antigen is from 8-35 amino acids in length, particularly wherein the peptide antigen is from 8-12 amino acids in length or from 29-35 amino acids in length.

Clause 10. The immunogenic composition of any one of the prior clauses, wherein the peptide tag is C-terminal to the peptide antigen in the conjugate.

Clause 11. The immunogenic composition of any one of the prior clauses, wherein
the peptide tag comprises a ratio of positively charged amino acids to negatively charged amino acids of 5:1 if the conjugate comprises the net positive charge; or
the peptide tag comprises a ratio of negatively charged amino acids to positively charged amino acids of 5:1 if the conjugate comprises the net negative charge.

Clause 12. The immunogenic composition of any one of the prior clauses, wherein:
if the conjugate comprises the net positive charge, the peptide tag comprises 8, 9, 10, 11, or 12 positively charged amino acids and 2 negatively charged amino acids; or
if the conjugate comprises the net negative charge, the peptide tag comprises 8, 9, 10, 11, or 12 negatively charged amino acids and 2 positively charged amino acids.

Clause 13. The immunogenic composition of any one of the prior clauses, wherein
the conjugate comprises the net negative charge, and the peptide tag comprises 10 positively charged amino acids and 2 negatively charged amino acids; or the conjugate comprises the net negative charge, and the peptide tag comprises 10 negatively charged amino acids and 2 positively charged amino acids.

Clause 14. The immunogenic composition of any one of the prior clauses, wherein
the negatively charged residues in the peptide tag are selected from aspartic acid and glutamic acid; and
the positively charged residues in the peptide tag are selected from lysine, arginine, and histidine.

Clause 15. The immunogenic composition of any one of the prior clauses, wherein the adjuvant is polyI:C.

Clause 16. The immunogenic composition of any one of the prior clauses, wherein the adjuvant is linked to the conjugate.

Clause 17. The immunogenic composition of any one of the prior clauses, wherein the adjuvant is linked to the conjugate by a linker, optionally wherein the linker is a hydrophilic linker.

Clause 18. The immunogenic composition of clause 16 or 17, wherein a ratio of adjuvant to conjugate in the immunogenic composition is from 1:100 to 1:10 mol/mol, particularly wherein the ratio of adjuvant to conjugate in the immunogenic composition is from 1:20 to 1:10 mol/mol or about 1:20 mol/mol.

Clause 19. The immunogenic composition of any one of the prior clauses, wherein the adjuvant comprises a pattern recognition receptor agonist.

Clause 20. The immunogenic composition of clause 19, wherein the pattern recognition receptor agonist comprises a toll-like receptor (TLR) agonist, a Stimulator of Interferon Genes (STING) agonist, a C-type lectin receptor (CLR) agonist, a RIG-I-like receptor (RLR) agonist, or a NOD-like receptor (NLR) agonist.

Clause 21. The immunogenic composition of clause 20, wherein the toll-like receptor agonist is a toll-like receptor 7/8 agonist, particularly wherein the toll-like receptor 7/8 agonist is a imidazoquinoline-based toll-like receptor 7/8 agonist.

Clause 22. The immunogenic composition of any one of the prior clauses, wherein the antigen is a tumor associated peptide antigen, a viral peptide antigen, a bacterial peptide antigen, or a protozoan peptide antigen.

Clause 23. The immunogenic composition of any one of the prior clauses, wherein the conjugate and the adjuvant self-assemble into the nanoparticles in phosphate buffered saline, pH 7.4.

Composition Formulations

The immunogenic compositions disclosed herein can be formulated as pharmaceutical compositions prepared for administration to a subject and which include a therapeutically effective amount of one or more of the nanoparticle-based immunogens as described herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Immunogenic compositions for administration to a subject can be pharmaceutical compositions and can include at least one further pharmaceutically acceptable additive such as carriers, thickeners, diluents, buffers, preservatives, surface active agents and the like in addition to the molecule of choice. Immunogenic compositions can also include one or more additional active ingredients such as antimicrobial agents, anesthetics, and the like. The pharmaceutically acceptable carriers useful for these formulations are conventional. *Remington's Pharmaceutical Sciences*, by E. W. Martin, Mack Publishing Co., Easton, PA, 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

To formulate the immunogenic compositions, the disclosed nanoparticle components or a solution containing the disclosed nanoparticle components can be combined with various pharmaceutically acceptable additives, as well as a base or vehicle for dispersion of the nanoparticles. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The immunogenic compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The instant disclosure also includes kits, packages and multi-container units containing the herein described immunogenic compositions, active ingredients, and/or means for administering the same for use in the prevention and treatment of diseases and other conditions in mammalian subjects. In one embodiment, these kits include a container or formulation that contains one or more of the immunogenic compositions described herein. In one example, the immunogenic composition is formulated in a pharmaceutical preparation for delivery to a subject. The immunogenic composition is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

III. Methods of Inducing an Immune Response

The immunogenic compositions including a peptide antigen as described herein may be used to elicit an immune response to the peptide antigen in a subject. Subjects that can benefit from the disclosed methods include human and veterinary subjects.

In some embodiments, a subject is selected for treatment that has, or is at risk for developing, an infection with an infectious agent that comprises the peptide antigen, for example because of exposure or the possibility of exposure to the infectious agent. Following administration of a therapeutically effective amount of a disclosed immunogenic composition, the subject can be monitored for the infection, symptoms associated with the infection, or both.

In some embodiments, a subject is selected for treatment that has, or is at risk for developing, a cancer, such as a malignant tumor. Following administration of a therapeutically effective amount of a disclosed immunogen, the subject can be monitored for the presence of the cancer, a reduction in tumor burden, any appropriate symptom of the cancer, or a combination thereof.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize the disease or condition. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a therapeutically effective amount of an immunogenic composition including a peptide antigen as disclosed herein can be for prophylactic or therapeutic purpose. When provided prophylactically, the immunogenic composition is provided in advance of any symptom, for example in advance of infection or development of a tumor. The prophylactic administration of the immunogenic composition serves to prevent or ameliorate subsequent development of the disease or condition. Hence in some embodiments, the methods involve selecting a subject at risk for contracting an infection or developing a tumor, and administering a therapeutically effective amount of a disclosed therapeutically effective amount of a disclosed immunogenic composition. The immunogenic composition can thus be provided prior to the anticipated exposure to the infectious agent, or development of the tumor, so as to attenuate the anticipated severity, duration or extent of an infection or tumor, and/or any associated disease symptoms.

When provided therapeutically, the disclosed immunogenic composition can be provided at or after the onset of a symptom of disease or condition, for example after development of a symptom of infection, or diagnosis of infection, or development of a symptom of a tumor, or diagnosis of a tumor. Treatment of the infection or tumor can include delaying and/or reducing signs or symptoms of the infection or tumor in the subject. In some examples, treatment using the methods disclosed herein prolongs the time of survival of the subject.

The immunogenic composition can be used in coordinate immunization protocols or combinatorial formulations.

In some embodiments, a therapeutically effective amount of a disclosed immunogenic composition can be administered to a subject to treat or inhibit an infectious agent in a subject. An infectious agent is an agent that can infect a subject, including, but not limited to, viruses, bacteria, and fungi. The subject can be selected for treatment that has, is suspected of having or is at risk of developing an infection with the infectious agent. In some embodiments, the infectious agent is a virus, a bacteria, or a fungus as described above, and the peptide antigen includes an antigen from the particular virus, bacteria, or fungus.

In some embodiments, a therapeutically effective amount of a disclosed immunogenic composition can be administered to a subject to treat or inhibit a tumor and/or a cancer in a subject. The subject can be selected for treatment that has, is suspected of having or is at risk of developing the tumor and/or cancer. In some embodiments, treating the tumor and/or cancer in the subject decreases growth and/or proliferation of the tumor. The tumor can be any tumor of interest and can be benign or malignant.

Treatment of the tumor is generally initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

Treatment initiated after the development of a condition, such as malignant cancer, may result in decreasing the severity of the symptoms of one of the conditions, or completely removing the symptoms, or reducing metastasis, tumor volume or number of tumors. In some examples, the tumor becomes undetectable following treatment. In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased.

Subjects can be screened prior to initiating the disclosed therapies, for example to determine whether the subject has a tumor. The presence of a tumor can be determined by methods known in the art, and typically include cytological and morphological evaluation. The tumor can be an established tumor. The cells can be in vivo or ex vivo, including cells obtained from a biopsy. The presence of a tumor indicates that the tumor can be treated using the methods provided herein.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth, or the amount that is effective at reducing a sign or a symptom of the tumor. In another embodiment, a therapeutically effective amount is the amount necessary to inhibit infection by an infectious agent, or the amount that is effective at reducing a sign or a symptom of the infection. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells, or which reduce the load of infectious agent in the subject.

The actual dosage of the immunogenic composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

EXAMPLES

The following examples are provided to illustrate particular features of certain embodiments, but the scope of the claims should not be limited to those features exemplified.

Example 1

Enhancing the Magnitude and Breadth of Anti-Cancer T Cell Immunity with Peptide-Based Vaccines Vaccines comprised of peptide-based neoantigens offer a personalized approach for eliciting cancer-specific T cells able to mediate tumor clearance. However, the diverse properties of peptides (solubility, charge, etc.) can lead to variable and unpredictable immunogenicity. To limit this variability, a standardized approach for delivering peptide neoantigens in self-assembling nanoparticles that co-deliver Toll-like receptor-7/8 agonists (TLR-7/8a) was developed. The generalizability of this approach was evaluated for eliciting T cell responses and tumor clearance against a model antigen (SIINFEKL, SEQ ID NO: 1) and tumor neoantigens (MC38-derived) in syngeneic murine tumor models. Optimal immunogenicity and tumor clearance were observed when both the peptide and TLR-7/8a were co-delivered within the same nanoparticle. Moreover, it was shown that improved delivery led to enhanced breadth of responses by enabling a nearly 25-fold increase in the magnitude of CD8 T cell responses (~2.6% Dextramer$^+$) against MC38-derived neoantigens previously reported to be non-immunogenic (~0.1% Dextramer$^+$). Altogether, the data showing how peptide format and TLR agonist delivery can be optimized to maximize the breadth and potency of T cell mediated tumor clearance has implications for translating personalized cancer vaccine approaches to the clinic.

Cancers are characterized by genetic instability that can lead to non-synonymous mutations in exomic DNA resulting in the expression of altered self-proteins, referred to as neoantigens. Neoantigens presented as peptides in the context of MHC molecules on cancer cells represent a potential target for recognition by cytotoxic T lymphocytes (CTLs) that mediate tumor-specific killing.

The ability of immunotherapies to mediate tumor clearance and improve outcomes in patients by targeting neoantigens has been validated in clinical trials. Accordingly, prolonged survival and increased objective response rates using checkpoint inhibitors (CPIs), such as Pembrolizumab (anti-PD-1) and Ipilimumab (anti-CTLA-4), have been shown to correlate with tumor mutational burden (neoantigen load) that is associated with neoantigen-specific CTL responses. Moreover, retrospective evaluation of the T cell receptor (TCR) specificity of highly enriched tumor-infiltrating lymphocyte (TIL) cultures used in adoptive cell therapies (ACTs) have identified that both neoantigen-specific CD4+ and CD8+ CTLs against a single neoantigen specificity can mediate complete and durable regression of tumors. While these studies underscore the tremendous potential of targeting neoantigens with CTLs to improve patient outcomes, vaccines that elicit de novo CTL responses against tumor antigens are needed to improve treatment efficacy in patients who have little to no pre-existing cancer-specific CTL responses.

Immunizing patients with subunit vaccines comprising their unique set of neoantigens provides a potentially effective means of generating de novo neoantigen-specific CTL responses for use alone or in combination with other immunotherapies. Indeed, advances in sequencing technologies and in silico prediction algorithms have made it possible to rapidly identify neoantigens from tumors that can be exploited for use in individualized vaccines using a variety of delivery platforms, including live vectors, DNA, RNA and peptides[9-13]. Among these approaches, peptide-based vaccines manufactured by chemical synthesis provide the potential advantages over live vectors, in that they are scalable and are not limited by anti-vector immunity[14, 15], allowing for repeatable administration to boost T cell responses above a protective threshold[16]. Moreover, peptides can be combined with defined adjuvants to increase the magnitude and enhance the quality of CD4+ and CD8+ CTL responses[17, 18], which may provide an advantage over DNA and RNA approaches that rely on endogenous antigen production that can be shutdown by Interferons (IFNs) induced by adjuvants[19, 20].

Achieving safe and effective individualized peptide vaccines for cancer patients requires an understanding of how the various parameters of peptide vaccines (peptide length and composition, immunostimulant properties, delivery platform, etc.) can be optimally combined to reliably promote high magnitude T cell responses against any tumor associated antigen, including any possible patient-specific neoantigen.

Conventional peptide-based cancer vaccine approaches, which deliver minimal T cell epitopes within the context of ~20-30 amino acid synthetic long peptides (SLPs), are known[21-25]. These approaches are largely based on observations that SLPs can promote higher T cell responses as compared with both ~8-10 amino acid minimal epitopes and whole proteins[26]. While injection site retention (depot effect), favorable processing of SLPs to promote cross-presentation and increased persistence of antigen presentation in vivo have all been proposed as mechanisms to account for the improved activity of SLPs[27-29], it is unclear whether or how peptide length directly mediates these effects. Moreover, both short peptides and whole protein can induce high magnitude T cell immunity depending on how they are delivered, which suggests that mode of delivery but not length may be critical for activity. Less clear is the role of embedded CD4 T helper epitopes, composition (hydrophilic/hydrophobic, charge, etc.) and hydrodynamic behavior of the peptides towards immunogenicity.

In addition to the properties of the peptide, the immunostimulant and delivery platform (i.e., vaccine adjuvants) also play key roles in promoting T cell immunity to peptide vaccines[17, 18, 30-32]. Adjuvants, such as certain Toll-like receptor agonists (TLRa) that induce Type I IFNs and IL-12, are useful for promoting antigen cross-presentation and for priming Th1-type CD4 T cell immunity[18]. How TLRa and antigen are delivered also play a role. Conventional wisdom suggests that optimizing T cell responses to protein and peptide antigens with TLRa requires delivery platforms that restrict both components to lymph nodes draining the sites of administration, which provides persistent APC activation and antigen presentation in lymph nodes while at the same time preventing toxicity associated with systemic TLRa distribution[33-35].

There is currently no consensus as to the optimal parameters for constructing peptide-based vaccines to achieve T cell immunity. Indeed, the lack of generally agreed upon design principles for eliciting T cell responses to peptide-based vaccines may in part explain why the majority of neoantigens predicted to be immunogenic have been reported to be non-immunogenic delivered using gold-standard vaccination approaches based on synthetic long peptides and RNA[10, 11]. This presents a problem since potentially effective neoantigen targets may be discarded as "non-immunogenic" due to sub-optimal vaccine design rather than an inherent incompatibility with binding to host MHCs or recognition by the host's TCR repertoire.

To provide a greater understanding of the use of peptide antigens in vaccines to generate robust anti-cancer immunity, various properties of peptide antigens (length, composition, morphology and size) were systematically evaluated, and their co-delivery with either or both immunostimulatory Toll-like receptor-7 and -8 agonists (TLR-7/8a) and a CD4 T cell helper epitope influenced the magnitude of CTL responses and anti-cancer immunity following vaccination in vivo. Peptides of varying lengths and compositions containing CD8 epitopes from a model antigen (OVA) and MC38-derived tumor neoantigens were evaluated in combination with different TLR-7/8a formats (small molecule, particle or peptide-TLR-7/8a conjugate) for their capacity to elicit CD4+ and CD8+ T cell responses and tumor clearance in mice.

The results showed that the delivery of peptide antigens on rigid, globular structures that assemble into stable supramolecular associates together with an adjuvant that induces persistent, lymph node focused production of Type I IFNs and IL-12 can induce T cell immunity to peptide antigens. After controlling for the format of peptide delivery, it was found that modifying the length and composition of amino acids flanking minimal epitopes was not as useful in influencing T cell responses.

Figure 1B:
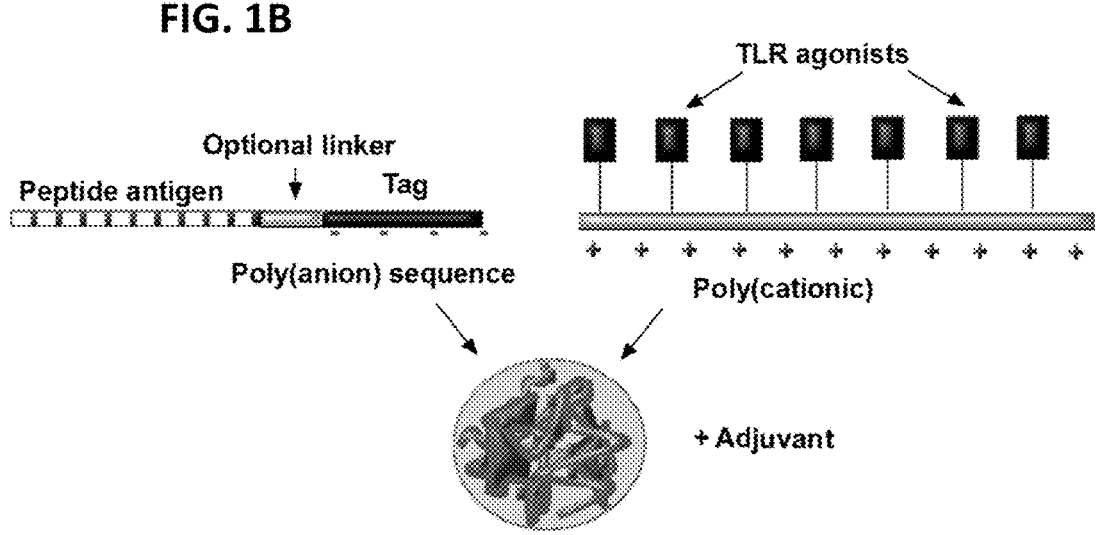
Figure 1C:
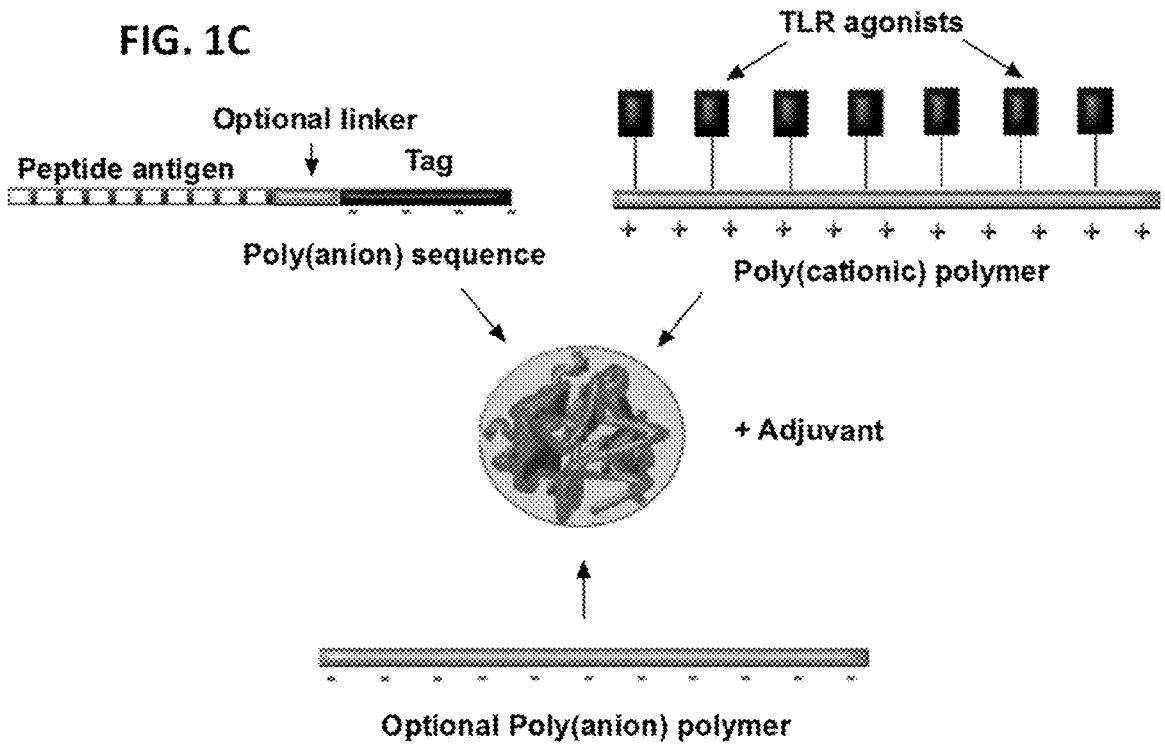
Figure 1D:
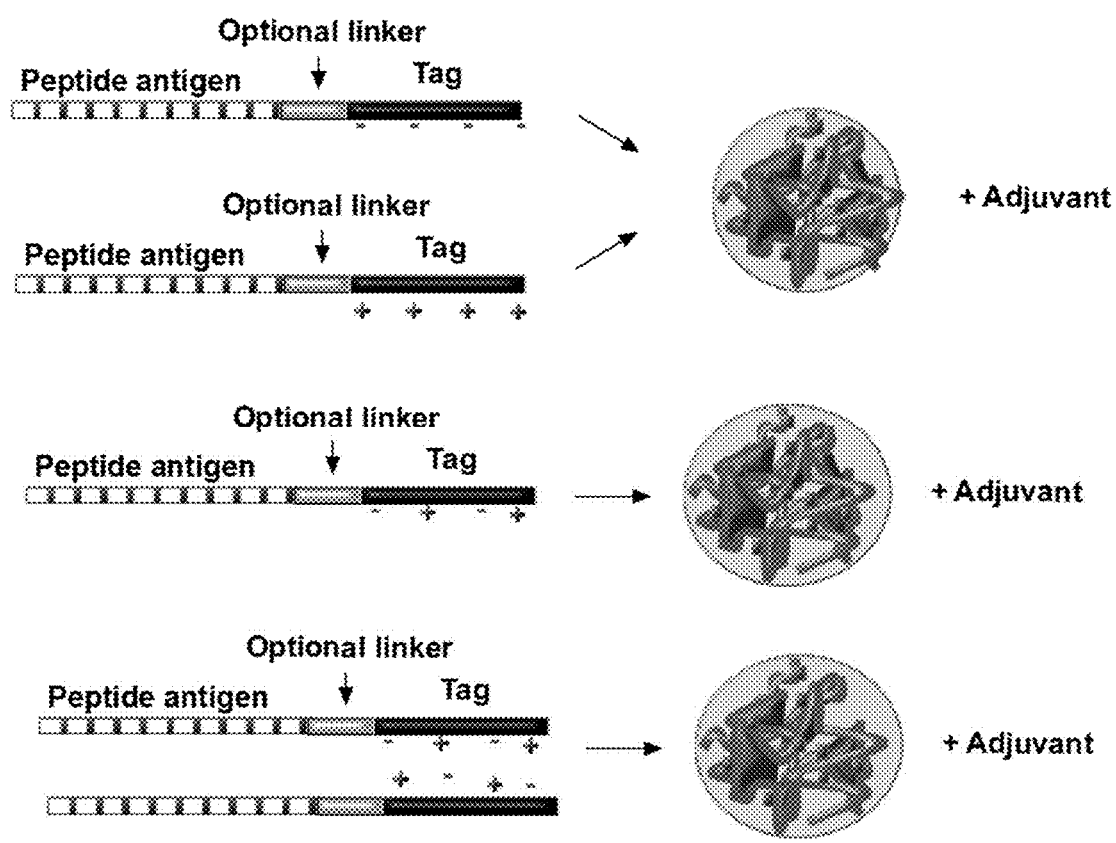

Based on the need to standardize the format of peptide delivery in rigid nanoparticles together with an adjuvant that provides persistent innate immune stimulation, a chemically defined and controlled approach was developed for co-delivering multiple peptide antigens with TLR-7/8a in self-assembling polymer nanoparticles comprised of polyelectrolyte complexes referred to herein as polyplexes (FIG. 1).

The highest magnitude CD8 T cell responses and tumor clearance were observed when both the peptide and TLR-7/8a were co-delivered within the same nanoparticle. Notably, polyplexes delivering short, peptide based minimal epitopes were as effective as long peptides, wherein the minimal epitope is embedded within a longer peptide sequence, with or without co-delivered CD4+ helper T cell epitopes, which suggests that long peptides and CD4 helper epitopes are not strictly required for eliciting T cell responses to peptide-based minimal epitopes co-delivered with potent innate immunostimulants in a nanoparticle format.

To exhibit the important implications of these results, it was shown that neoantigens previously shown to be "non-immunogenic" when delivered as SLPs combined with polyICLC, which is being developed clinically, can be made to induce high magnitude (>1% dextramer+ CD8 T cell responses) when co-delivered in a particulate format together with TLR-7/8a. These data show how a chemically defined adjuvant delivery platform can utilize the breadth and potency of T cell mediated immunity and tumor clearance with peptide antigens.

Results

Insoluble but not Soluble Long Peptides Promote Anti-Tumor CD8 T Cell Immunity

Figure 2D:
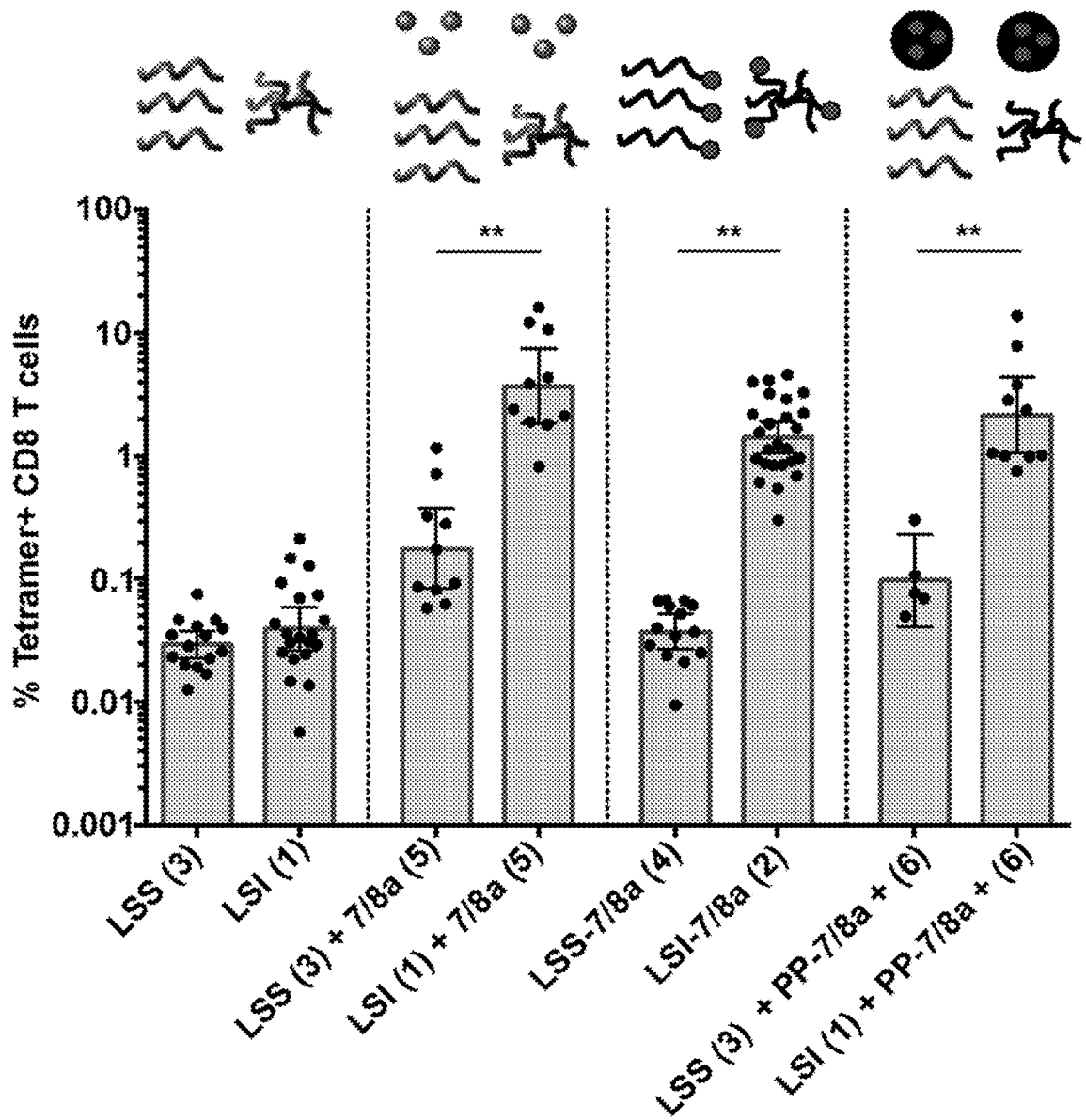

Prior studies have investigated how the length of peptides delivering minimal cytotoxic T cell (CTL) epitopes influence vaccine immunogenicity, however, these studies have not investigated how the composition of amino acid residues flanking the CTL epitope influence peptide solubility and innate and adaptive immunity in vivo. To investigate how the composition of amino acids flanking minimal epitopes influences the immunogenicity of synthetic long peptide (SLP)-based vaccines, a long peptide comprised of the minimal CTL epitope from Ovalbumin, referred to as SIINFEKL ($OVA_{257-264}$, SEQ ID NO: 1) fused to a model flanking sequence containing a human CD4 T cell epitope derived from cytomegalovirus (CMV) was synthesized (FIG. 1A). Notably, it was found that the long peptide containing the SIINFEKL (SEQ ID NO: 1) epitope was insoluble in aqueous buffers at pH 7.4, but that replacing 9 hydrophobic amino acid residues with hydrophilic residues restored the solubility of the peptide (FIGS. 2A and 2B). The insoluble and soluble long peptide SIINFEKL (SEQ ID NO: 1) constructs are referred herein as LSI and LSS for simplicity.

As peptides alone are tolerogenic and require combination with vaccine adjuvants, the long peptides used in these studies were combined with different forms of Toll-like receptor-7 and -8 agonist (TLR-7/8a) to be used as model adjuvants that induce T cell immunity. TLR-7/8a were chosen for these studies because they induce broad-based activation of dendritic cells and the production of cytokines (e.g., IL-12, Type I IFNs and IP-10) that promote ThI-type CD4 and CD8 T cell responses to exogenously delivered protein and peptide antigens. It is known that the method of adjuvant delivery can impact innate and adaptive immunity, thus the long peptides were combined with different formats of TLR-7/8a adjuvants to systematically evaluate how both peptide and adjuvant format together impact immunity in vivo. Accordingly, the TLR-7/8a was either attached site-specifically to the C-terminal residue of the peptides so as to not disrupt the CTL epitope (FIGS. 2A and 2B), or the long peptides were simply mixed with small molecule or particulate forms of the TLR-7/8a that have been shown to induce high magnitude $CD8^+$ T cell immunity when combined with protein antigens (FIG. 2C).

Figure 2E:
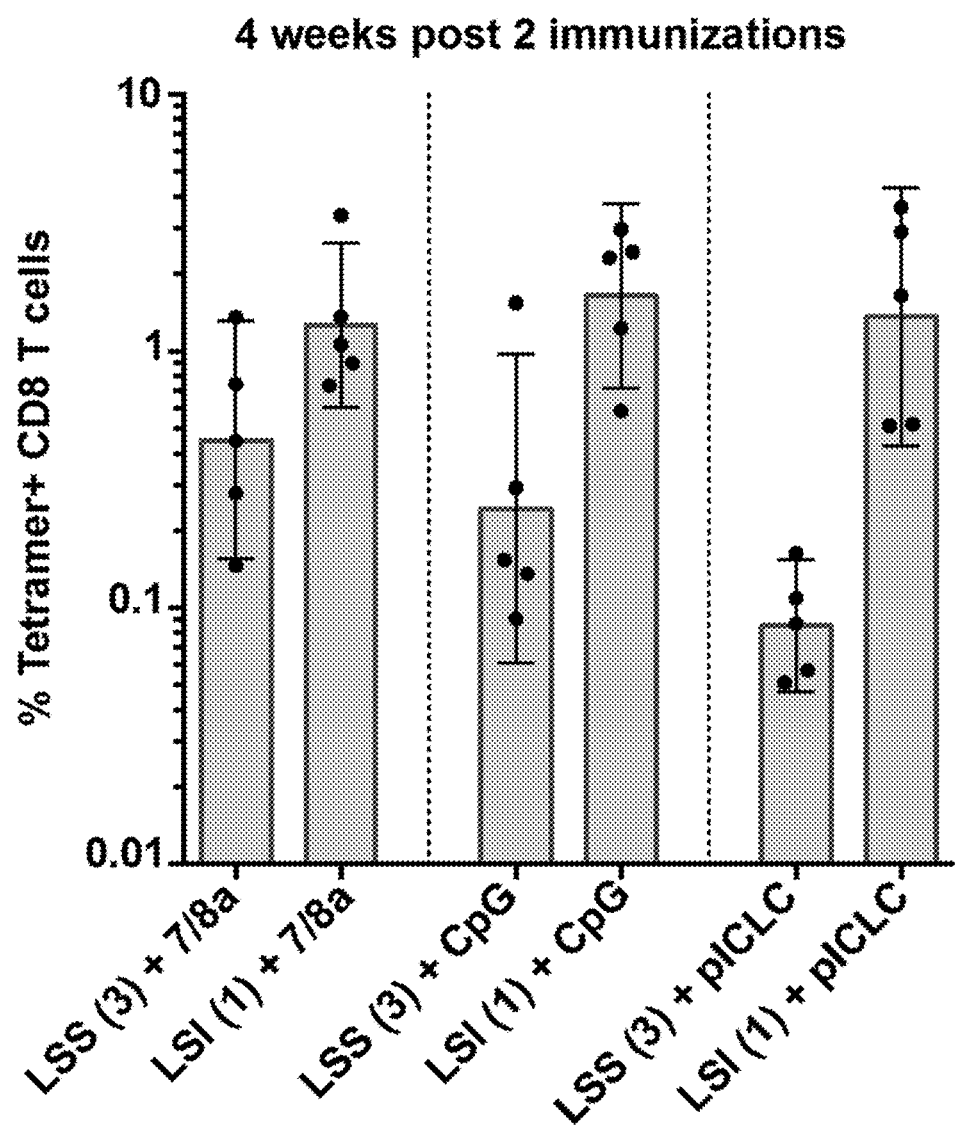

The first series of studies evaluated the impact of peptide solubility and adjuvant delivery format on $CD8^+$ T cell anti-tumor immunity was investigated. Surprisingly, only the insoluble long peptide (LSI) combined with adjuvant induced $CD8^+$ T cell responses to the SIINFEKL (SEQ ID NO: 1) epitope (FIG. 2D), while the soluble long peptides alone or combined with different formats of the TLR-7/8a were unable to induce a CD8+ T cell response above background. Both LSS and LSI were combined with the TLR-9 and TLR-3 agonists, CpG and polyICLC, respectively, to assess whether these observations are generalizable to other adjuvants. Notably, the insoluble long peptide combined with either CpG or polyICLC elicited nearly 10-fold higher levels of $CD8^+$ T cell responses as compared with the soluble peptide co-administered with the same adjuvants (FIG. 2E).

Figure 3A:
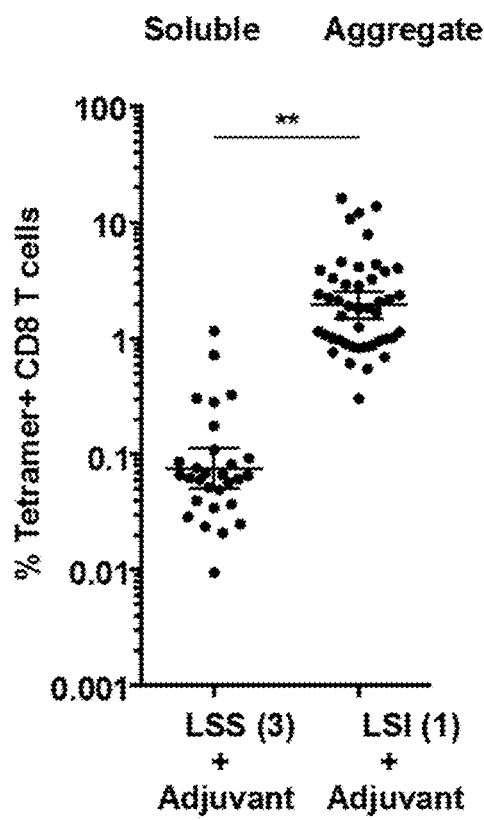
FIGS. 3A-3D: Influence of peptide solubility on $CD8^+$ T cell responses. (3A) Data stratified according to peptide format (soluble or aggregate) (n=30 and 45). (3B) Survival was assessed in mice that were immunized with Listeria-OVA (n=5), LSS+adjuvant (n=15) or LSI+adjuvant (n=15) at days 0 and 14 and were then intravenously challenged with $1\times10^5$ B16 melanoma cells expressing full-length Ovalbumin at day 42. (3C and 3D) Mice were injected subcutaneously in the flank with $1\times10^5$ B16 melanoma cells expressing full-length Ovalbumin at day 0 and then were vaccinated subcutaneously in the footpad at days 3 and 17 post. (3C) Tetramer$^+$ CD8 T cell responses were evaluated from whole blood of mice after a single immunization at day 16 (n=10) and (3D) Tumor volumes (n=10) were assessed at serial timepoints; day 18 timepoint is shown. Data on log scale are reported as geometric mean with 95% confidence interval (CI). Student's T test was used for comparison of 2 groups; comparison of multiple groups for statistical significance was determined using one-way ANOVA with Bonferroni correction; ns, not significant (P>0.05); *, P<0.05; **, P<0.01.
Figure 3B:
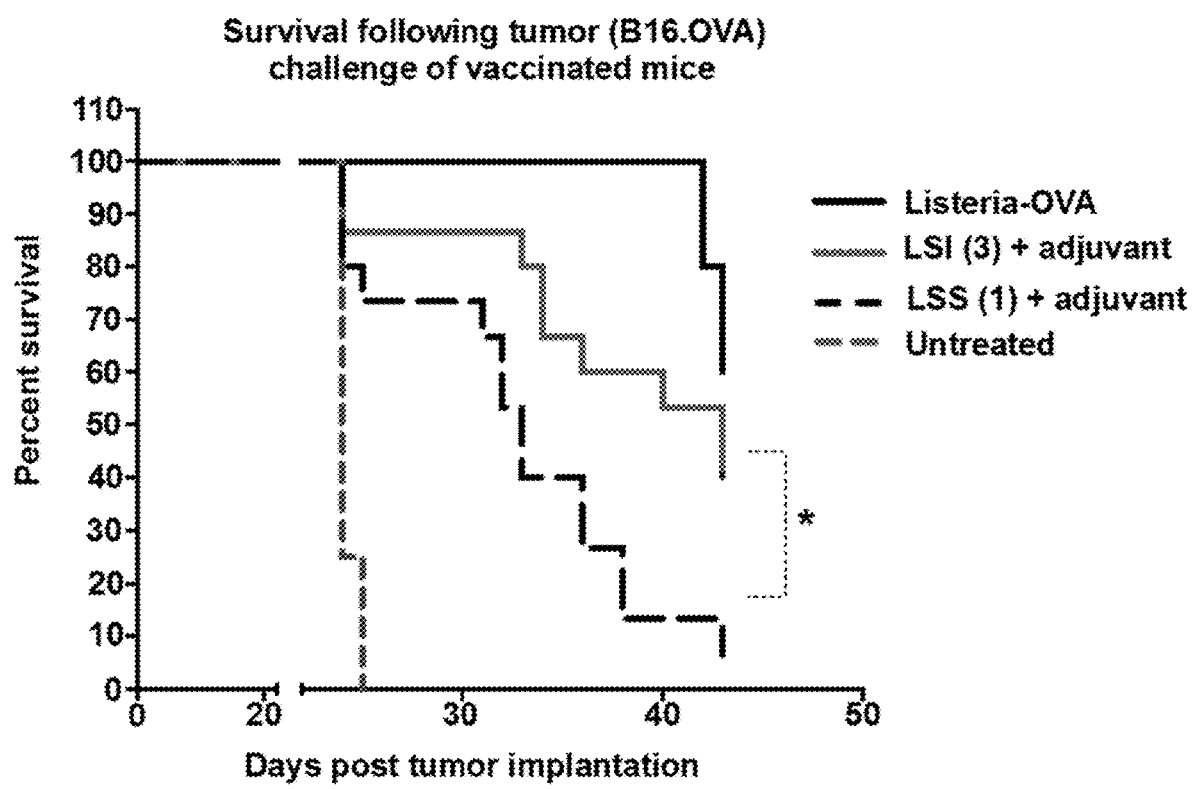
Figure 3C:
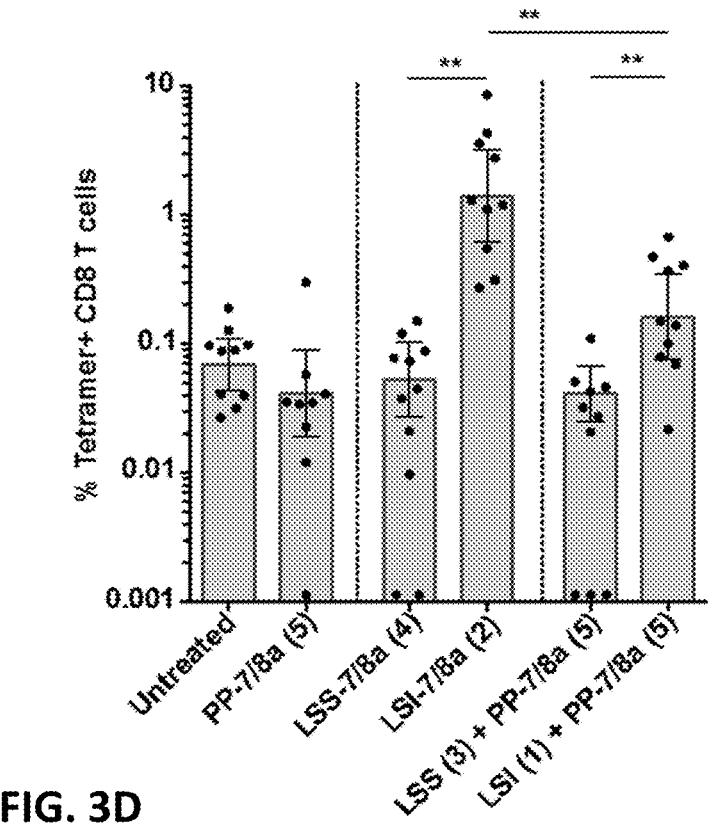
Figure 3D:
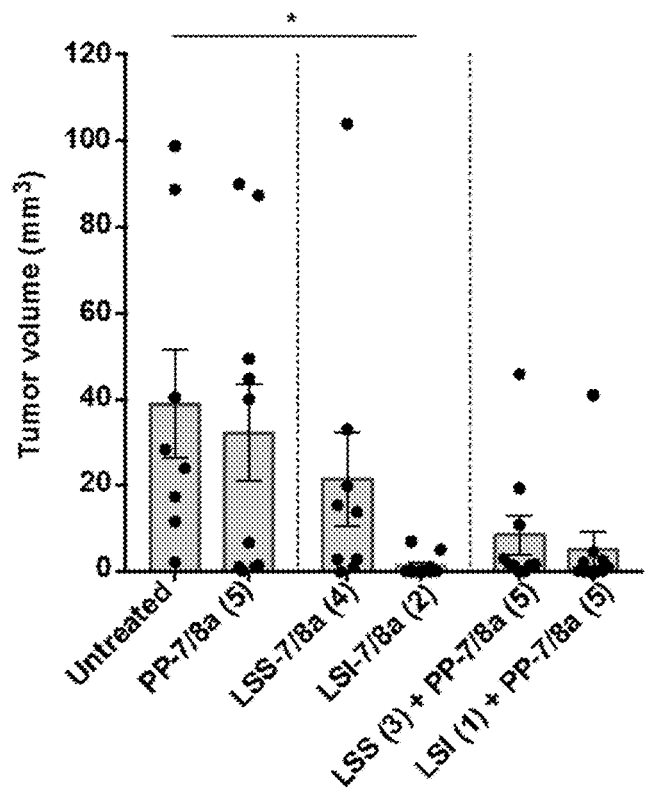

To assess the functional capacity of the $CD8^+$ T cells elicited by the long peptide vaccines, mice were intravenously challenged with B16 melanoma cells expressing full-length Ovalbumin that contains the SIINFEKL (SEQ ID NO: 1) epitope at 4 weeks after receiving 2 immunizations of either LSI or LSS admixed with either the small molecule or particle TLR-7/8a adjuvants. Increased CD8 T cell responses (FIG. 3A) for mice that received LSI was closely associated with improvements in median survival as compared with mice that received the soluble long peptide with adjuvant (43 versus 33 days) (FIG. 3B). We next assessed whether the $CD8^+$ T cell elicited by the insoluble long peptides could also provide superior efficacy in the treatment of established tumors as compared with the soluble long peptides (FIGS. 3C and 3D). Consistent with our earlier findings, the insoluble long peptides (LSI) combined with any format of TLR-7/8a adjuvants induced significantly higher magnitude of CD8+ T cell responses (FIG. 3C) and reduced tumor volumes (FIG. 3D) as compared with soluble long peptides administered with the same formats of adjuvant. Importantly, co-delivery of the TLR-7/8a together with the insoluble peptide antigen (LSI-7/8a) resulted in the highest CD8 T cells and greatest reductions in tumor volume (FIGS. 3C and 3D).

Induced Aggregation of Long Peptide Neoantigens Enhances CTL Responses

Figure 4A:
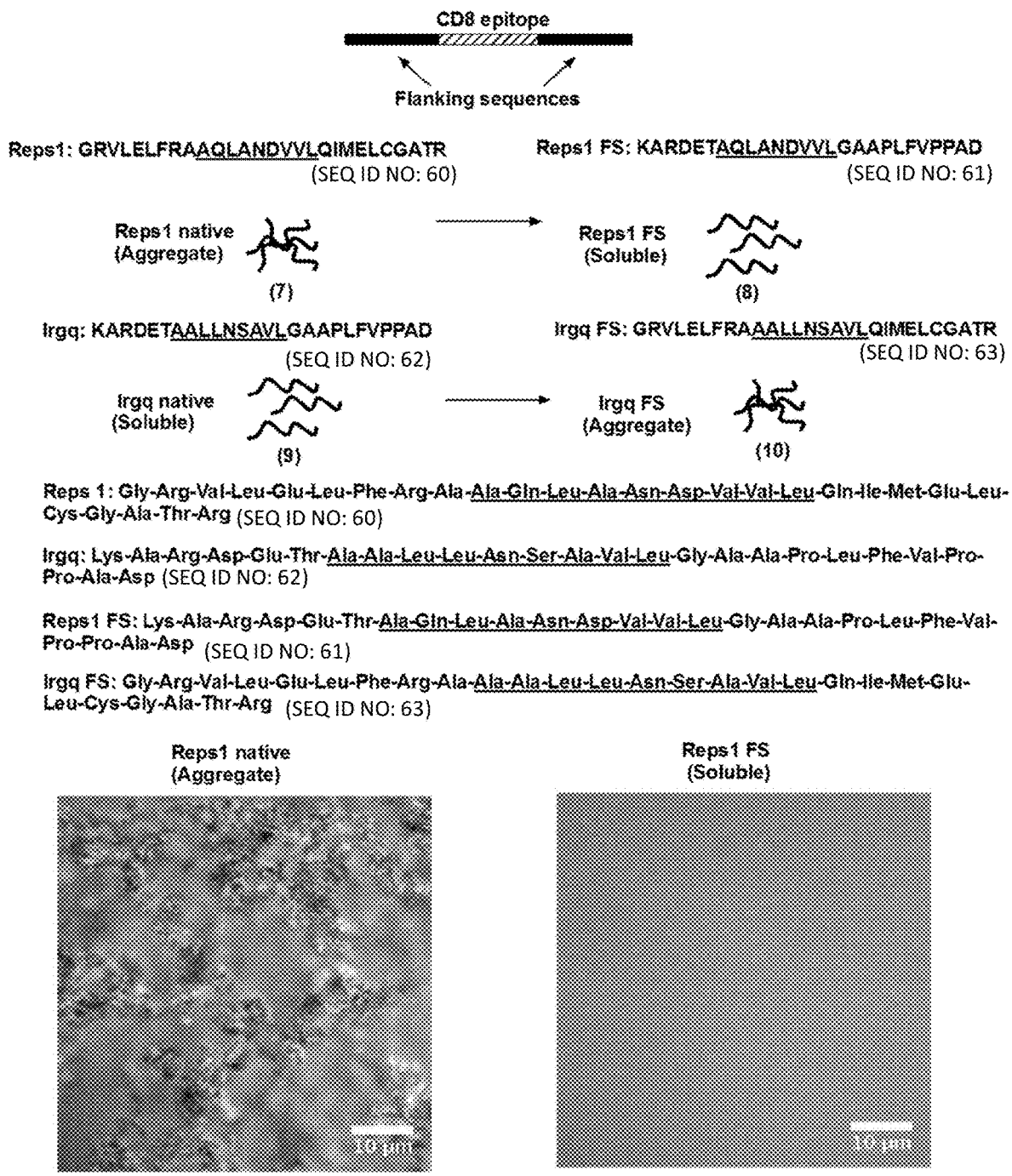

The next series of studies sought to address the impact of peptide format on the immunogenicity of peptide-based neoantigen vaccines. Most current peptide-based vaccine approaches for cancer treatment deliver CTL epitopes within the context of 25-35 amino acid synthetic long peptides. These approaches have also been applied to the delivery of predicted neoantigens identified from tumor biopsies for use as individualized cancer vaccines. It has not been determined, however, how the sequences of amino acids flanking minimal CTL epitopes influence peptide solubility and immunogenicity in vivo. To investigate the effects of the sequences flanking predicted neoantigen CTL epitopes, the hydrodynamic behavior and immunogenicity of two long peptide neoantigens (Reps1 and Irgq) was evaluated. These peptides were derived from MC38 murine melanoma either as the native sequences or as chimeric antigens where the amino acids flanking the epitopes of Reps (Ala-Gln-Leu-Ala-Asn-Asp-Val-Val-Leu, SEQ ID NO: 21) and Irgq (Ala-Ala-Leu-Leu-Asn-Ser-Ala-Val-Leu, SEQ ID NO: 22) were exchanged to create chimers: Reps FS and Irgq FS (FIG. 4A). Notably, whereas Reps1 alone is insoluble in aqueous buffers, the minimal CTL epitope of Reps1 delivered with the flanking sequences of the Irgq neoantigen was found to give a water-soluble long peptide (Reps1 FS) (FIG. 4A). In contrast, the native Irgq long peptide alone was found to assemble into some supramolecular structures in aqueous buffers but Irgq FS assembled into an aggregate in aqueous buffer.

Figure 4B:
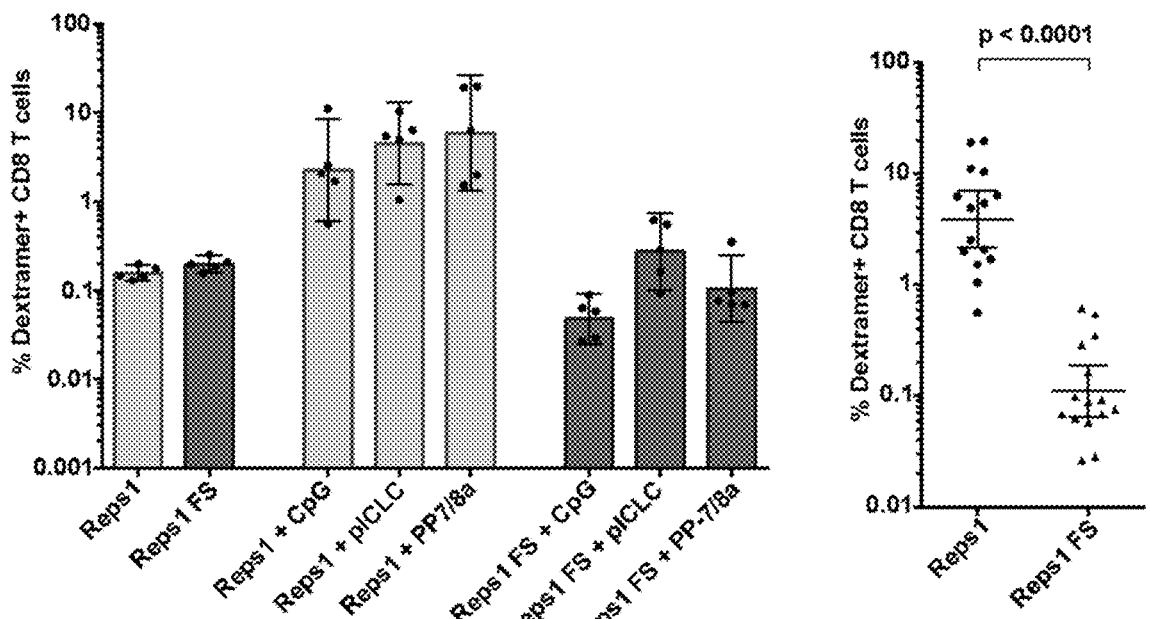
Figure 4C:
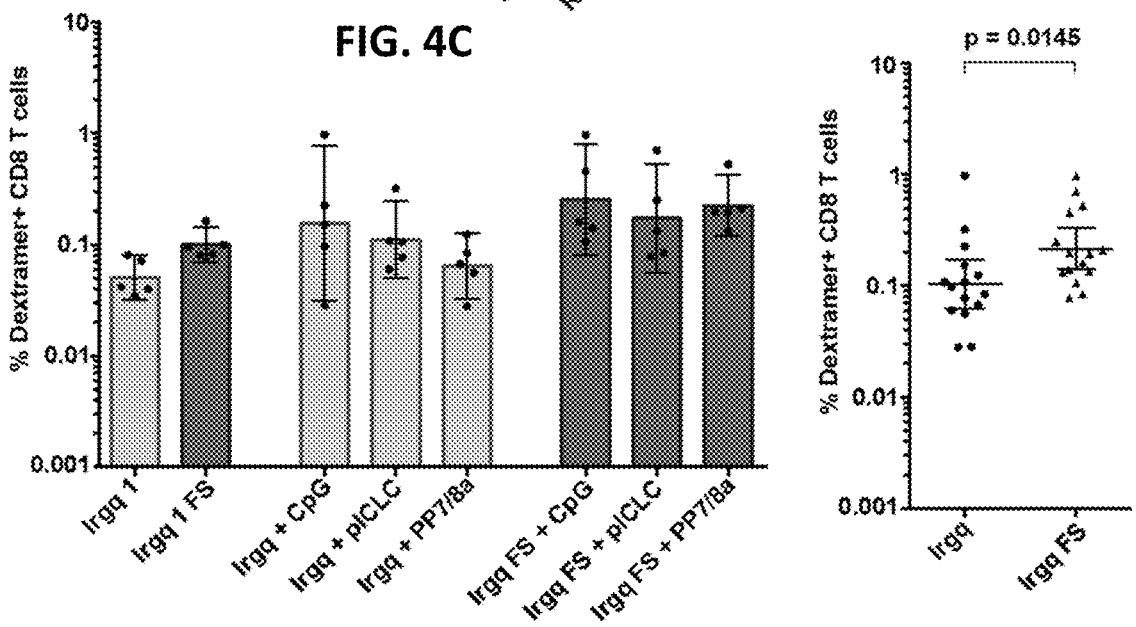
Figure 4D:
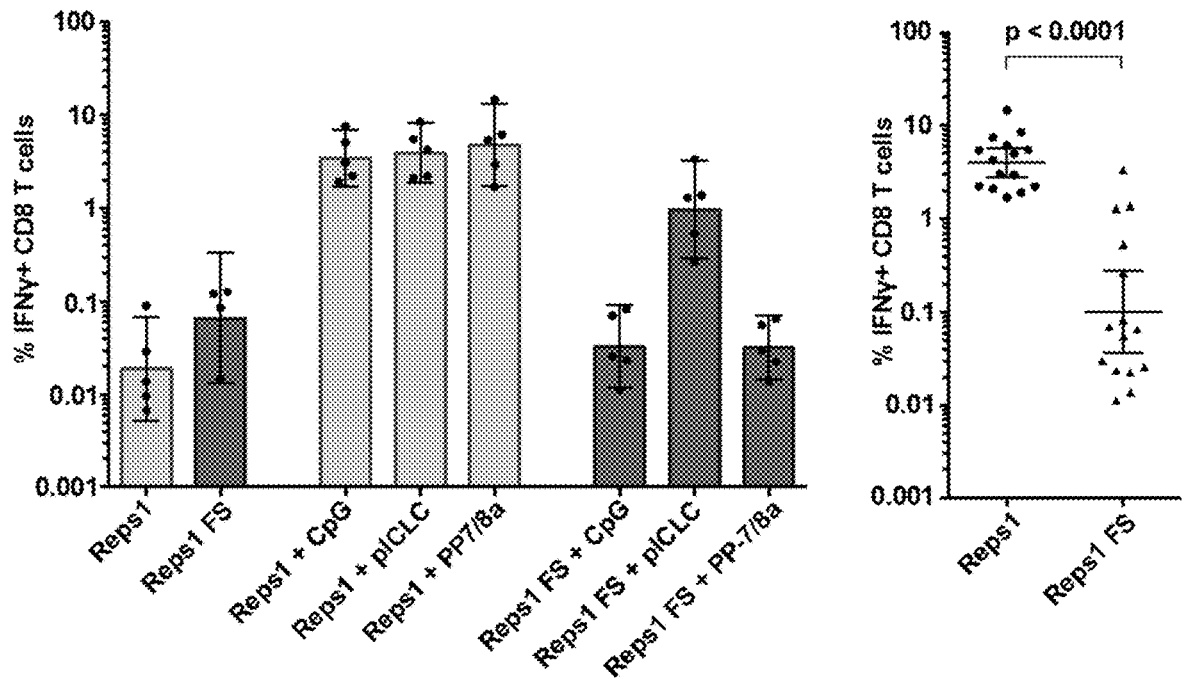
Figure 4E:
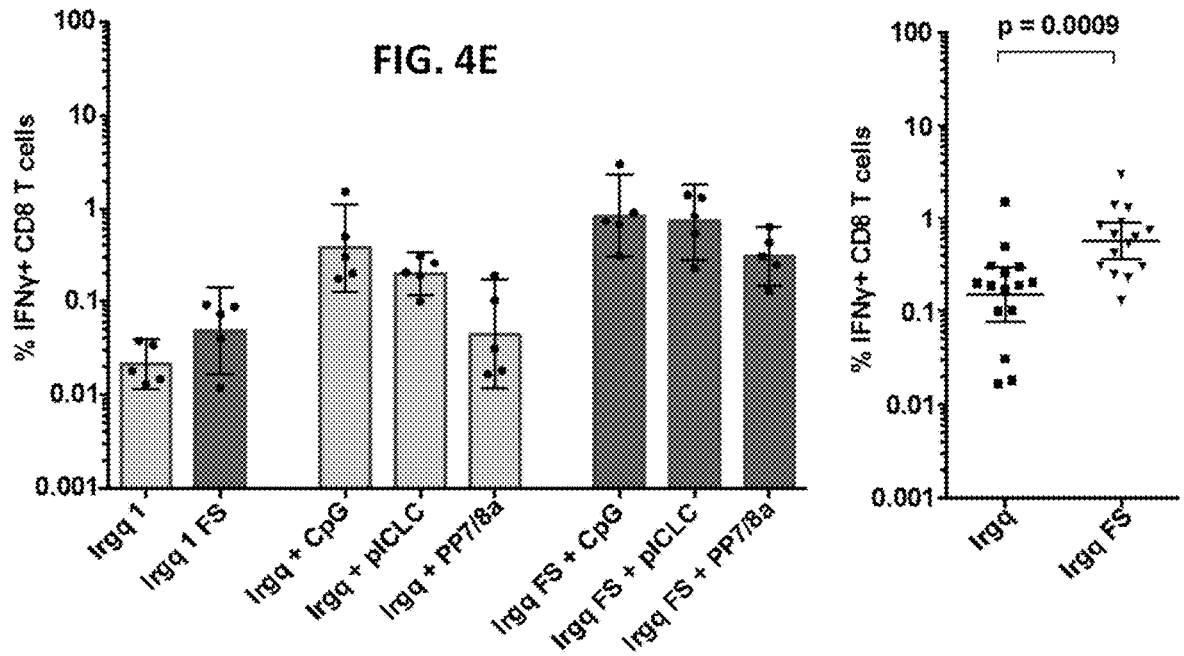

It was then assessed how the flanking sequence composition of long peptide neoantigens influences CTL responses following vaccination. Unexpectedly, the aggregated peptides (Reps1 and Irgq FS) admixed with the particulate TLR-7/8a (PP-7/8a) elicited nearly 20- and 100-fold higher magnitude $CD8^+$ T cell responses against the Reps1 and Irgq epitopes as compared with the soluble sequences delivering the same minimal epitopes admixed with PP-7/8a (FIGS. 4B and 4C). Because TLR-3 and TLR-9 agonists, polyICLC and CpG are currently being used as adjuvants that are admixed with long peptides in cancer vaccines, an investigation of how long peptide neoantigen format influences T cell responses when combined with these adjuvants was performed (FIG. 4B-4G). Antigen-specific $CD8^+$T cell responses were significantly higher for both epitopes (Reps1 and Irgq) delivered within the context of water insoluble long peptides, providing between 2-100-fold higher responses as compared with the soluble long peptides admixed with the same adjuvants (FIG. 4B-4G). Altogether, these data suggest that amino acids flanking minimal CTL epitopes are a major determinant of long peptide-based neoantigen hydrodynamic behavior and immunogenicity.

Aggregated Long Peptides Increase the Persistence of Antigen Presentation In Vivo The effect of how long peptide solubility impacts the magnitude and duration of antigen presentation in vivo was investigated. Soluble (LSS) or insoluble (LSI) long peptides delivering the minimal CTL epitope from Ovalbumin (SIINFEKL, SEQ ID NO: 1) were either admixed with small molecule TLR-7/8a or particulate TLR-7/8a, or directly conjugated to the TLR-7/8a (LSS-7/8a and LSI-7/8a) and were administered to mice on day 0. To evaluate antigen presentation in vivo, CFSE-labeled OT-I cells that recognize and undergo cellular division in response to antigen-presenting cells presenting the minimal epitope, SIINFEKL (SEQ ID NO: 1), were administered to vaccinated mice at either days 0, 3 or 6. The labeled cells were then isolated 6 days after administration and enumerated to determine whether the cells proliferated in response to antigen presentation in vivo. In all combinations with adjuvant, the insoluble long peptide (LSI) led to increased CD8 T cell expansion that led to a higher overall magnitude of antigen-specific CD8 T cells (FIGS. 5A-5B). Notably, while differences in expansion of CD8 T cells were comparable for mice that received either LSS and LSI admixed with the small molecule TLR-7/8a at day 0, the insoluble peptide provided markedly higher expansion of CD8 T cells that were transferred to mice at days 3 and 6 after vaccination, suggesting that the insoluble peptide provided increased durability of antigen presentation in vivo as compared with the soluble peptide (FIGS. 5A-5B).

Nanoparticle Polymer Complexes (Polyplexes) as Carriers of Peptide-Based Neoantigens and TLR-7/8 Agonist Adjuvants The above studies showed that the hydrodynamic behavior of peptide-based vaccines has a major effect on their immunogenicity in vivo. Minimal CTL epitopes delivered within the context of water insoluble long peptides were found to lead to ~20-100 fold higher CD8 T cell responses as compared with the same epitopes delivered as soluble long peptides. Moreover, co-delivering, i.e. physically linking, a potent TLR-7/8a adjuvant to the insoluble peptides further increased T cell responses and improved clearance of established tumors. These data suggest that delivering peptide-based minimal CTL epitopes on particulate carriers co-delivering immuno-stimulants that induce the production of IL-12 and Type-I IFNs is critical to optimizing their immunogenicity for eliciting CD8 T cell responses.

While the prior studies established that insoluble peptides are markedly more immunogenic than soluble peptide sequences, translating the use of highly hydrophobic peptides for clinical use is limited by manufacturing as well as regulatory challenges. Accordingly, hydrophobic peptide sequences are often difficult to manufacture during solid-phase peptide synthesis and can lead to sequence truncation or may have limited solubility in common solvent systems required for purification by reverse-phase HPLC. Moreover, insoluble peptides form aggregates in aqueous buffers, which prevent a limitation to administering such vaccines to patients in aqueous buffers or necessitate the use of organic solvents, such as DMSO.

Indeed, one alternative to the use of hydrophobic peptides is to physically link or incorporate the peptide antigen in particles based on PLGA, liposomes or emulsions. Such particle-based systems have been shown to markedly improve the activity of protein and peptide-based antigens; however, a limitation of this approach is that incorporation efficiency of peptides into different particle systems varies depending on the sequence (and therefore physical and chemical properties) of the peptide antigen. Thus, the use of pre-formed particles may offer limited utility in the setting of a personalized cancer vaccine approach, where each patient will require a unique set of peptide-based neoantigens, that must be optimized for incorporation into the particles, followed by challenging analytical methods to determine the amount of peptide attachment/incorporation.

Here the use of polymer nanoparticle polyplexes is reported as an alternative to the use of pre-formed particles as scaffolds for delivering peptide-based neoantigens for cancer vaccines. To incorporate peptides into polymer nanoparticle polyplexes, a peptide tag sequence that carriers a net positive or negative charge is linked to a peptide antigen through an optional linker during solid-phase peptide synthesis, or off-resin, to create a peptide antigen conjugate (FIG. 1). The tag sequence of the peptide antigen conjugate ("conjugate") serves two functions: (1) the tag improves promotes water solubility during manufacturing; and (2) the tag provides a net charge that allows the peptide antigen conjugate to bind to a polymer carrier of opposite charge, which together undergo assembly of polymer complexes, referred to as polyplexes, through charge neutralization (FIG. 1). To ensure co-delivery of the peptide antigen with a potent immunostimulant, such as a TLR-7/8 agonist, the TLR-7/8a can be linked to either the peptide antigen or a polymer that incorporated in the polyplex.

The initial studies focused on optimizing the activity of poly(cationic) polymer carriers of TLR-7/8 for electrostatic complexation of peptide antigen conjugates wherein the peptide antigen tag carries a net negative charge. Initial work focused on the use of polyethylenimine (PEI)-based polymers as prior studies established that PEI is an effective poly(cationic) polymer for complexation of DNA plasmids to form nanoparticle complexes, or polyplexes, that can effectively enter cells and deliver DNA into the cytosol for expression. The ability of PEI-based polymers to deliver poly(anions) into the cytosol of the cells could also be an effective approach for improving the efficiency of antigen cross-presentation, as peptide entry into the cytosol has been proposed as a rate-limiting step for presentation of exogenously delivered antigens in the context of MHC-I molecules.

PEI-Based Carriers of TLR-7/8a

Figure 6:
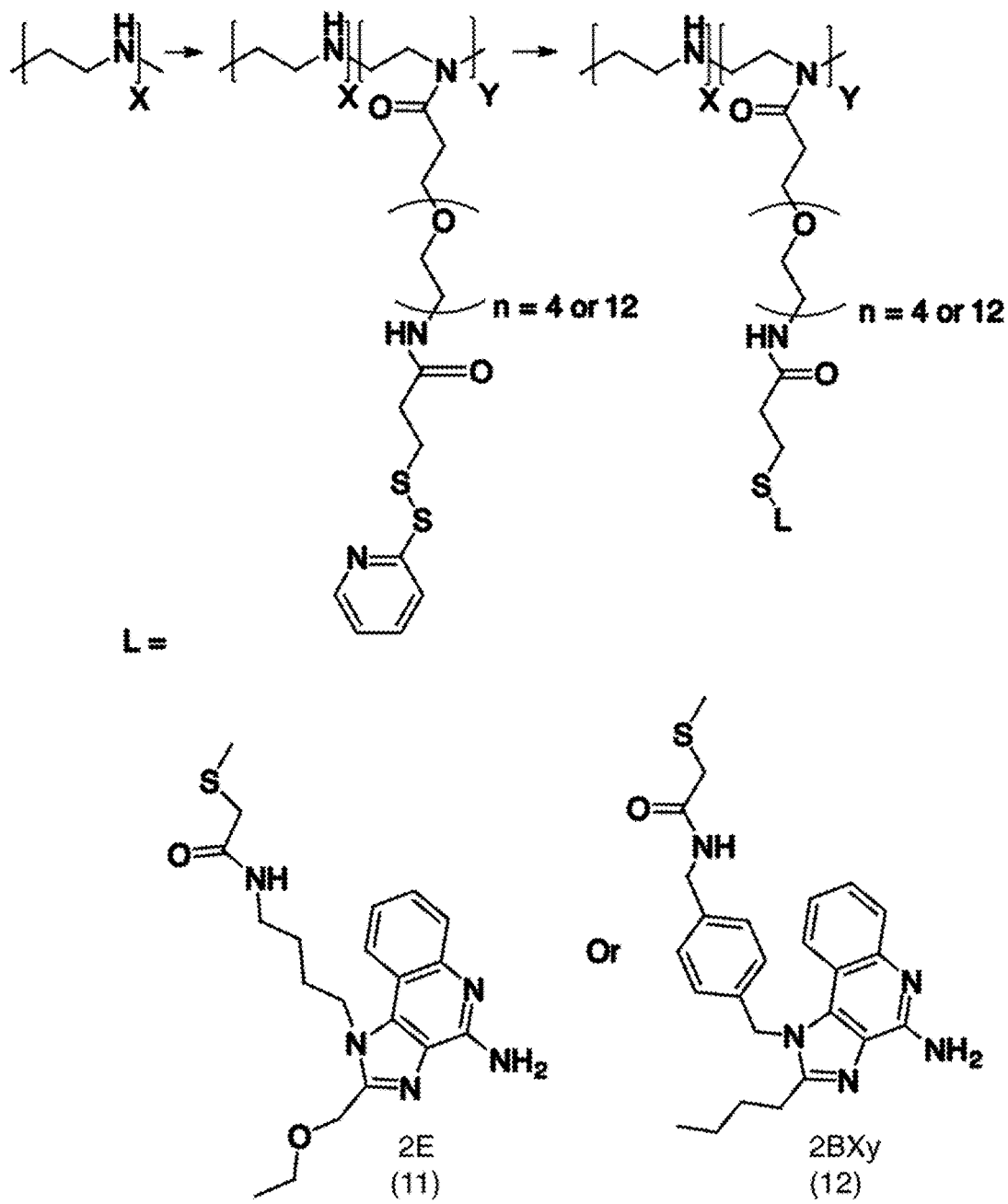
FIG. 6: Poly(cationic) poly(ethylenimine) (PEI)-based carriers of TLR-7/8a. Linear PEI (L-PEI) was modified with a heterofunctional PEG cross-linker, NHS-PEG-PDS to generate a thiol-reactive PEI that was further modified with the TLR-7/8a, 2E (11) or 2BXy (12).

PEI-based carriers were prepared by reacting 25 kDa linear or 10 kDa branched PEI polymers with different amounts of NHS-PEG4-Pyridyldisulfide (PDS) and NHS-PEG12-PDS in methanol at room temperature, followed by the addition of moderate (2E) or high potency (2BXy) TLR-7/8a modified with a thiol linker that displaces the PDS to form a disulfide bond between the TLR-7/8a and the PEG cross-linker (FIG. 6). The PEI-TLR-7/8a conjugates were purified by dialysis against methanol and then transferred into DMSO. Importantly, special care was taken not to concentrate the PEI-TLR-7/8a conjugates wherein the TLR-7/8a was linked to the polymer backbone through a disulfide bond as the polymers were prone to cross-linking at high concentrations, possibly through thiol-exchange. The characteristics of the polymer TLR-7/8a are summarized in Table 1. Notably, an unexpected finding was that the maximal loading of PEG-TLR-7/8a to the polymer backbone was 3%, or only 3 out of 100 monomer units could be linked to PEG-TLR-7/8a.

Figure 7A:
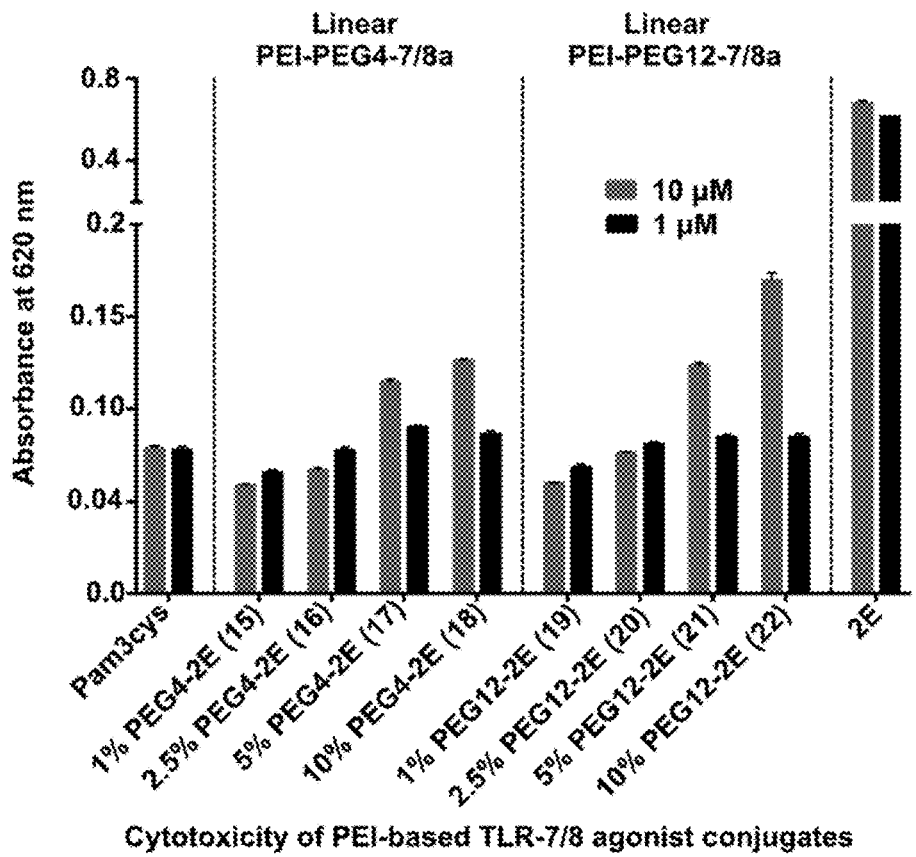
FIGS. 7A-7B: In vitro activity of PEI-based carriers of TLR-7/8a. Linear PEI-based carriers linked to different densities (mol %) of TLR-7/8a through either PEG4 (4 ethylene oxide units) or PEG12 (12 ethylene oxide units) were incubated with HEK293 cells expressing a plasmid that encodes human TLR-7 and a reporter enzyme, SEAP, that is expressed following signaling through TLR-7. After incubation overnight, the HEK293 cells were assessed for TLR-7 binding by measuring conversion of a substrate that absorbs at 620 nm (7A) as well as for viability (7B).
Figure 7B:
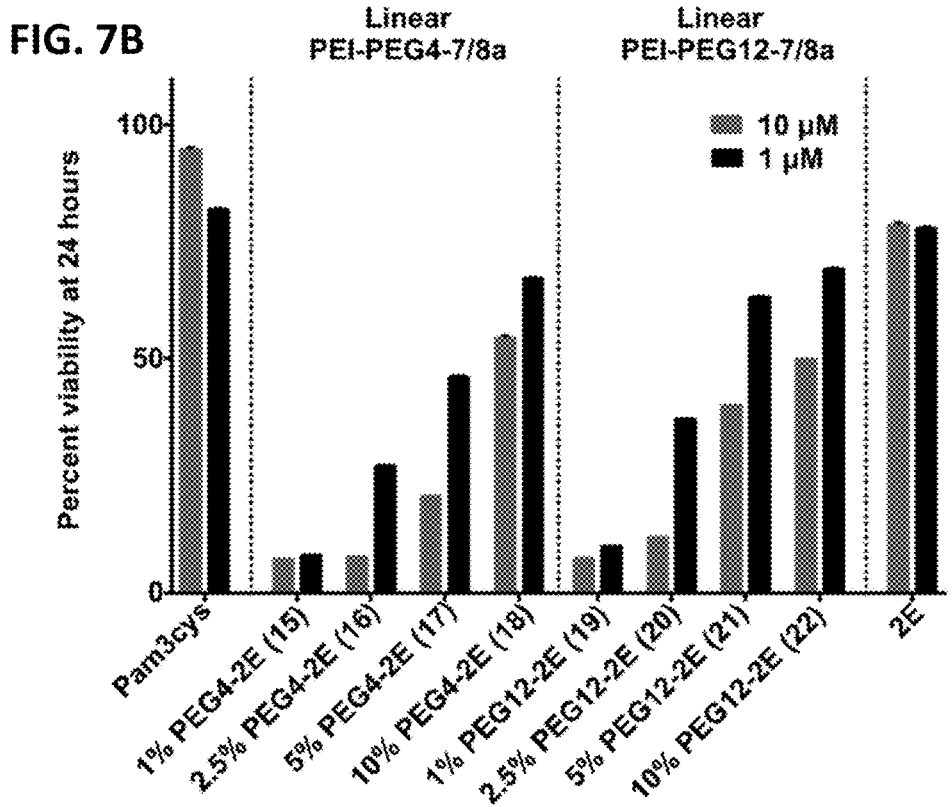

The PEI-TLR-7/8a conjugates were screened for activity in vitro against HEK293 cells expressing human TLR-7 (hTLR-7). TLR-7 agonist binding to hTLR-7 in these cells results in secretion of a reporter enzyme that can be detected using a chromophore that absorbs at 620 nm (FIG. 7A). As shown in FIG. 7A, increasing density of the PEG linked TLR-7/8a was associated with increased TLR-7 activity that was independent of PEG linker length. Notably, as PEI is known to be cytotoxic, the viability of the HEK293 cells were evaluated 24 hours after incubation with the different PEI-TLR-7/8a conjugates (FIG. 7B). PEI-TLR-7/8a conjugates with the lowest density (1% of total monomers; or 1 out of 100 monomers linked to TLR-7/8a) of TLR-7/8a attached were less than 10% viable after 24 hours, indicating that 90% of the cells were killed by the PEI-TLR-7/8a compounds, whereas >50% of cells treated with the highest density of attached PEG-TLR-7/8a were viable after 24 hours (FIG. 7B). These results indicate that increasing the density of PEG linked TLR-7/8a on the polymer backbones can improve TLR-7 activity and reduce cellular cytotoxicity.

Figure 8A:
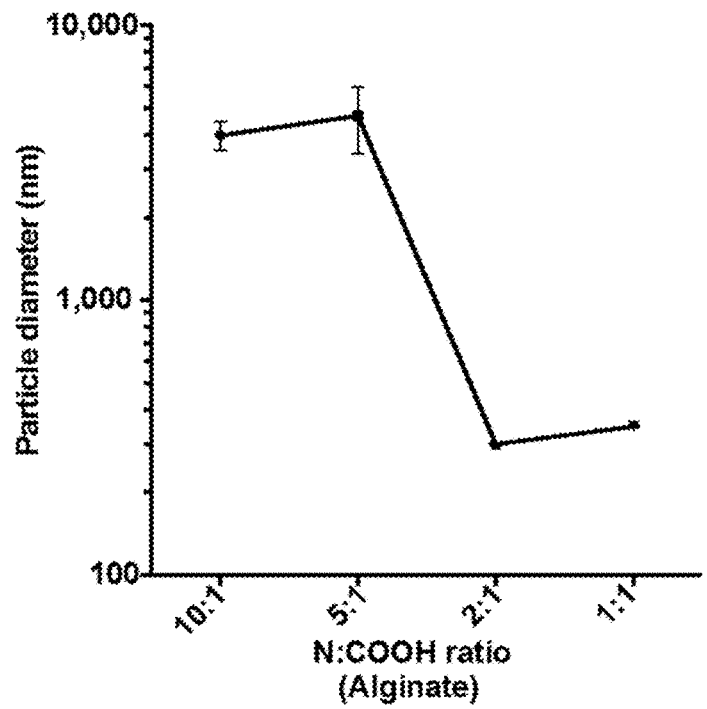
FIGS. 8A-8B: Formation of nanoparticle polyplexes between PEI-based carriers of TLR-7/8a and the poly(anion) sodium alginate. L-PEI 2.5% PEG4-2BXy, compound 27, was formulated with different charge ratios of sodium alginate at a concentration of 0.1 mg/mL in PBS at pH 7.4 and then assessed for particle size (8A) and zeta potential (8B) using dynamic light scattering and electrophoretic mobility measurements.
Figure 8B:
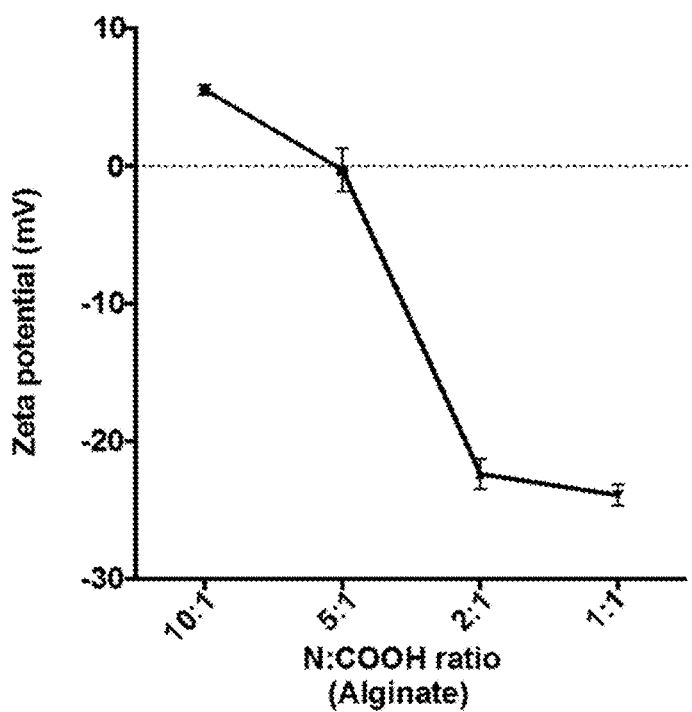
Figure 10:
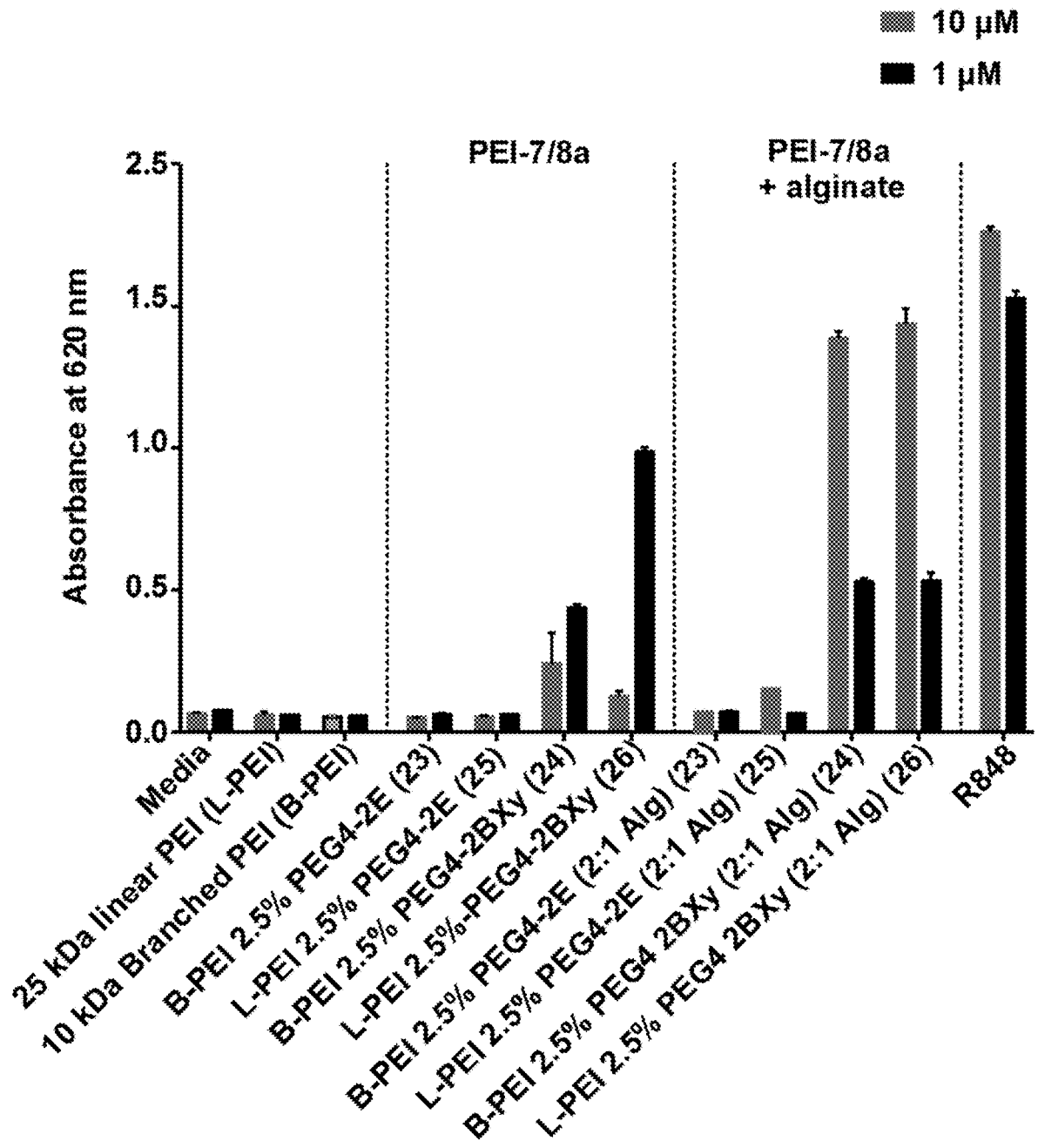
FIG. 10: Charge neutralization of poly(cationic) PEI-based carriers of TLR-7/8a with sodium alginate, increased agonist potency and density improves in vitro activity for binding TLR-7. HEK293 cells expressing hTLR-7 were incubated with either 10 or 1 μM (normalized for TLR-7/8a concentration) of linear (L-PEI) or branched (B-PEI)-based polymer carriers linked to either compound (11) or compound (12) used alone or complexes with alginate at a charge ratio of 2:1. After incubation overnight, the HEK293 cells were assessed for TLR-7 binding by measuring conversion of a substrate that absorbs at 620 nm.

As a means to reduce the cellular cytotoxicity of PEI-based TLR-7/8a, a polyanionic poly(saccharide) biopolymer, Alginate, was complexed with PEI-TLR-7/8a at different charge ratios (N:COOH) to neutralize the high charge density that has been postulated to account for the cytotoxicity of PEI (FIG. 8A). While the PEI/Alginate complexes formed aggregates at ratios between 10:1 and 5:1, stable nanoparticles (~200-300 nm in diameter) with negative zeta potential (FIGS. 8A and 8B) were formed at charge ratios of 2:1 and 1:1. Importantly, these studies identified that ~2:1 to 1:5 N:COOH charge ratio is optimal for complexation of PEI-TLR-7/8a conjugates with Alginate to form stable nanoparticles. To evaluate the impact of the poly(anion) on the cytotoxicity of PEI, linear PEI (L-PEI) was complexed with either Alginate or single stranded RNA, poly(I:C), at different charge ratios and then incubated at different concentrations (10 or 1 µg/mL) with HEK293 cells for 24 hours (FIG. 9). Complexation of PEI with both Alginate and poly(I:C), which has an anionic poly(phosphoester) backbone, resulted in a marked reduction in cellular cytotoxicity caused by PEI, with a nearly 50% increase in cell viability using Alginate and pIC at charge ratios of 2:1 and 5:1, respectively, which are also found to lead to optimal sizes and stability of the nanoparticle complexes.

Figure 12A:
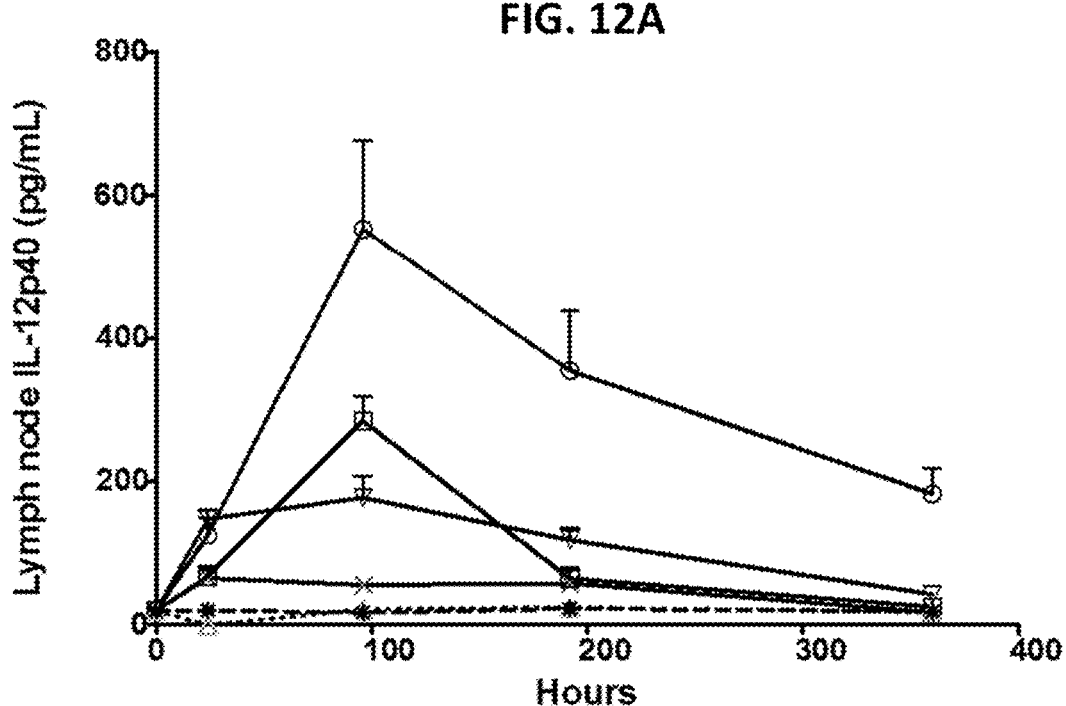
FIGS. 12A-12B: TLR-7/8a linked to PEI through a stable amide bond leads to prolonged immune activation in vivo. Mice were administered either compound (26) or compound (27) (normalized for Molarity of the TLR-7/8a, 50 or 10 μM) complexed with sodium alginate at a charge ratio of 2:1 delivered in 50 μL volume of PBS pH 7.4 solution given into both hind footpads at day 0. Lymph nodes draining the site of immunization were isolated at serial timepoints thereafter and then assessed for IL-12 (12A) and IP-10 (12B) by ELISA.
Figure 12B:
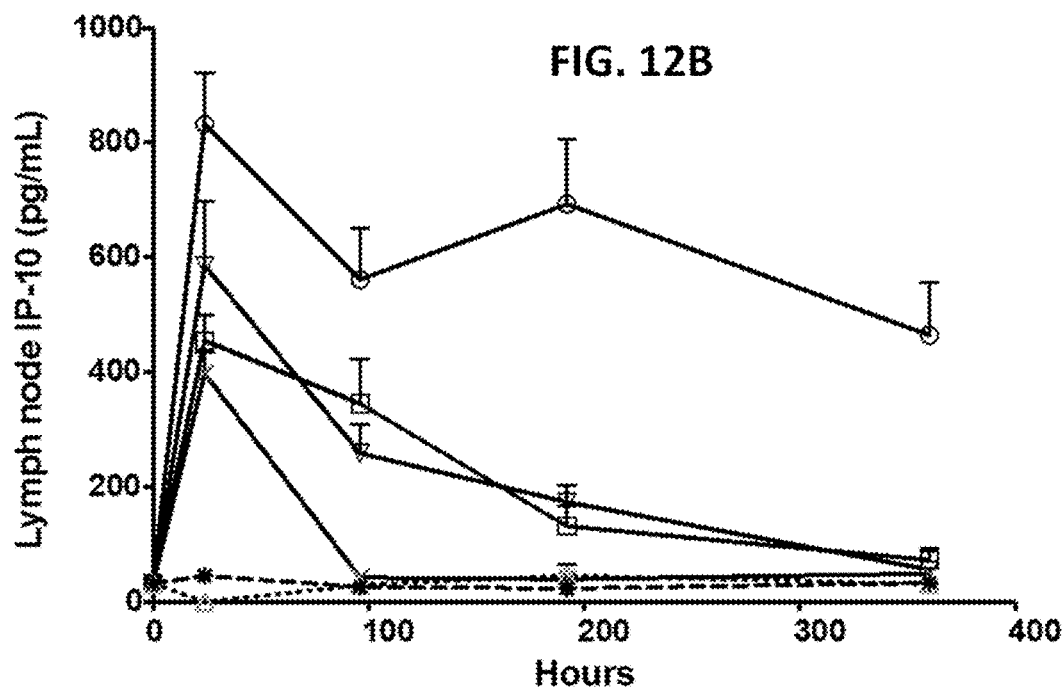
Figure 13A:
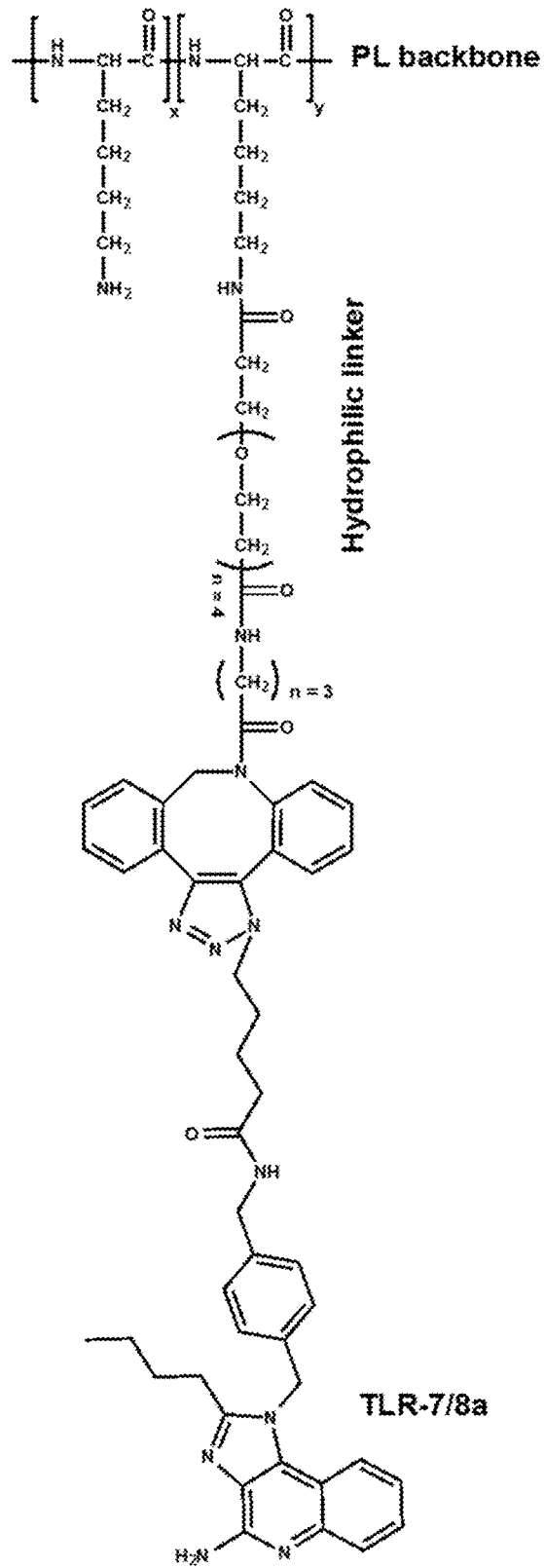

Next, how polymer architecture (linear versus branched), TLR-7/8a potency (2E versus 2BXy) and the use of alginate to form nanoparticle polyplexes impact the activity of PEI-based TLR-7/8a conjugates, was assessed (FIG. 10). Increasing TLR-7/8a potency and the use of alginate resulted in a marked increase in measured TLR-7 activity, whereas there were no discernible differences in activity between the linear and branched polymers (FIG. 10). Notably, complexation of PEI-TLR-7/8a with alginate resulted in nearly a doubling of activity at the highest concentration (10 μM) of PEI-TLR-7/8a used. These results indicate that increasing TLR-7/8a potency and charge neutralization of poly(cationic) based polymers through complexation with poly(anions) are effective means for improving activity of poly(cationic) polymer carriers of TLR-7/8a.

PEI-Based Carriers of TLR-7/8a Linked Through a Stable Amide Bond Lead to Prolonged Innate Immune Activation In Vivo The prior studies established that increasing the density and potency of TLR-7/8 agonists linked to linear PEI-based polymers complexed with poly(anions) improves their in vitro activity for signaling through TLR-7. The next studies evaluated the in vivo activity of PEI-based polymer carriers of TLR-7/8a, wherein the TLR-7/8a was linked to the PEI backbone either through a reducible disulfide bond ((26) FIG. 11) or through a stabile amide bond ((27) FIG. 11). Different linkages (disulfide versus amide) were used to determine how linker group stability impact in vivo activity. The PEI-TLR-7/8a conjugates complexed with Alginate were administered to the hind footpad of mice in 50 μL of PBS and then lymph nodes draining the site of vaccine administration were isolated at serial timepoints thereafter and assessed for the production of the cytokines IL-12 and IP-10, which are critical for promoting ThI CD4 T cell response and CD8 T cell immunity. Unexpectedly, the linkage of the TLR-7/8a to the PEI carrier through a stable amide bond resulted in higher magnitude and more persistent production of IL-12 and IP-10 as compared the PEI-TLR-7/8a conjugates wherein the TLR-7/8a was linked to the polymer backbone through a disulfide bond. Notably, 15 days after administration only the PEI-TLR-7/8a conjugates with a stable amide bond linking the TLR-7/8a to the polymer backbone were still inducing the production of IL-12 and IP-10 in draining lymph nodes. Based on the unexpected findings that the amide bond improves the magnitude and persistence of lymph node cytokine production in draining lymph nodes, which has been shown to be critical for promoting T cell responses to protein and peptide antigens, the remainder of the studies herein focused on using stable amide bonds to link the TLR-7/8a to the poly(cationic) polymer backbone.

Poly(Lysine)-Based Carriers of TLR-7/8a

While the studies using PEI-based carriers of TLR-7/8a identified several characteristics of poly(cationic) polymers carriers of TLR-7/8a that are critical for improving immune activity while at the same time reducing cytotoxicity, PEI-based polymers are considered non-biodegradable and may therefore may be limited for clinical use due to potential safety concerns. To overcome the potential safety issues with respect to PEI, poly(amino acid) based polymer carriers based on Poly(L-Lysine) (PLK) were used.

A 16,000 kDA linear PLK·HCl polymer was used as a starting material for linking TLR-7/8a. As the polymer is not soluble in methanol, the polymer was instead dissolved in 0.1M HEPES solution at pH 8.0 and then reacted with different amounts of a heterofunctional NHS-PEG4-DBCO cross-linker (FIG. 13A). The NHS-PEG4-DBCO has limited water solubility but quickly goes into solution following reaction with the PLK backbone. While the maximal loading of TLR-7/8a on PEI-based backbones was found to be less than 3%, possibly due to steric hindrance, loading of up to 45 mol % was achieved for linkage of the TLR-7/8a to the PLK backbones; however, increasing the density of the TLR-7/8a linked to the polymer backbone above 10% led to the formation of nano- and micro-sized supramolecular associates due to increasing density of the attached amphiphilic ligand molecule. Thus, it is preferred to link TLR-7/8a to PLK based polymers at densities less than 10 mol % but above ~1 mol % to prevent particle formation/aggregation but to ensure sufficient density of TLR-7/8a is linked to the polymer to allow for optimal immune activity. A summary of the characteristics of the different PLK-based TLR-7/8a carriers is summarized in Table 2.

The in vivo activity of two PLK-based carriers was evaluated next, wherein the TLR-7/8a was either linked through a stable amide bond, or an enzyme-degradable tetrapeptide linker at 5 mol % agonist density. Similar to the results observed for the PEI-based carriers of TLR-7/8a (FIG. 12), PLK based carriers of TLR-7/8a complexed with the poly(anion) alginate led to high magnitude and persistent lymph node IL-12 production (FIG. 13B). Notably, the PLK-based carrier linked to TLR-7/8a through the enzyme degradable linker resulted in lower magnitude IL-12 production at earlier time points (days 1 and 4) (FIG. 13B).

Altogether, these studies reveal how parameters of TLR-7/8a linked to poly(cationic) polymers can be optimized to promote lymph node cytokines, e.g., IL-12 and IP-10, that promote T cell immunity. Unexpectedly, densities of high potency TLR-7/8a agonists between 1-3 mol % and 1-10% linked to PEI and PLK-based polymers, respectively, through stable amide bonds using PEG linkers were identified as critical parameters for inducing high magnitude and persistent innate immune activation in vivo. Moreover, poly(anions), i.e., Alginate and poly(IC), were found to mitigate toxicity of the poly(cationic)-based polymer carriers of TLR-7/8a and promote the formation of stable nanoparticles that were found to be immuno-stimulatory in vivo.

Peptide Antigen Conjugates for Complexation to Poly(Cationic)-Based Polymer TLR-7/8a The next series of studies sought to evaluate the optimal parameters for electrostatically complexing peptide antigen conjugates, wherein a peptide antigen is linked to an optional linker that is linked to a peptide tag sequence that carriers a net negative charge, to poly(cationic) polymer carriers of TLR-7/8a.

The rationale for using charged peptide tag sequences is two-fold: (1) the charged tag sequence improves aqueous solubility of the peptides to facilitate manufacturing, and (2) the tag allows for electrostatic complexation to oppositely charged polymers that together self-assemble into nanoparticles complexes, termed polyplexes.

The initial studies focused on using peptide antigens linked to an optional linker that is fused to a negatively charged peptide sequence (FIG. 14A). As a proof-of-concept, and to determine the optimal charge density on the peptide antigens, i.e. neoantigens, needed to ensure reliable polyplex formation, the Reps1 neoantigen was fused to different lengths of poly(glutamic) acid sequences, either $(Glu)_5$ (residues 1-5 of SEQ ID NO: 23), $(Glu)_{10}$ (residues 1-10 of SEQ ID NO: 23), or $(Glu)_{15}$ (SEQ ID NO: 23) (FIG. 14A). To assess water solubility, Reps1 with or without a $(Glu)_n$ tag were suspended in PBS pH 7.4 at 0.5 mg/mL in a 200 μL volume and assessed for absorbance (OD) at 490 nm to indirectly assess turbidity due to scattering of light by insoluble particles in the buffer. Notably, whereas the native Reps1 sequence was found to be insoluble, addition of either the 5-, 10- or 15-mer glutamic acid sequences led to complete water solubility.

Figure 14C:
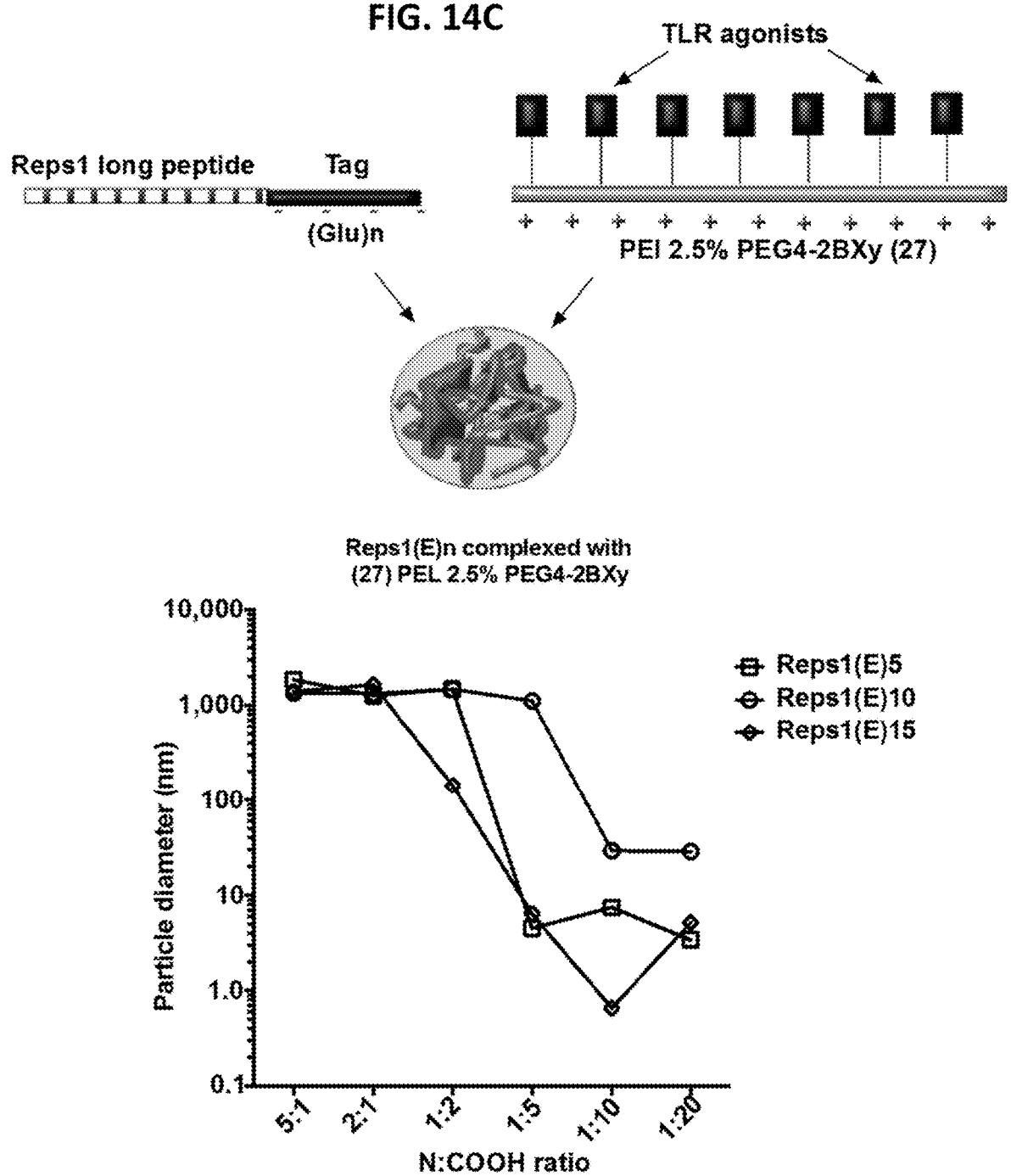
Figure 14D:
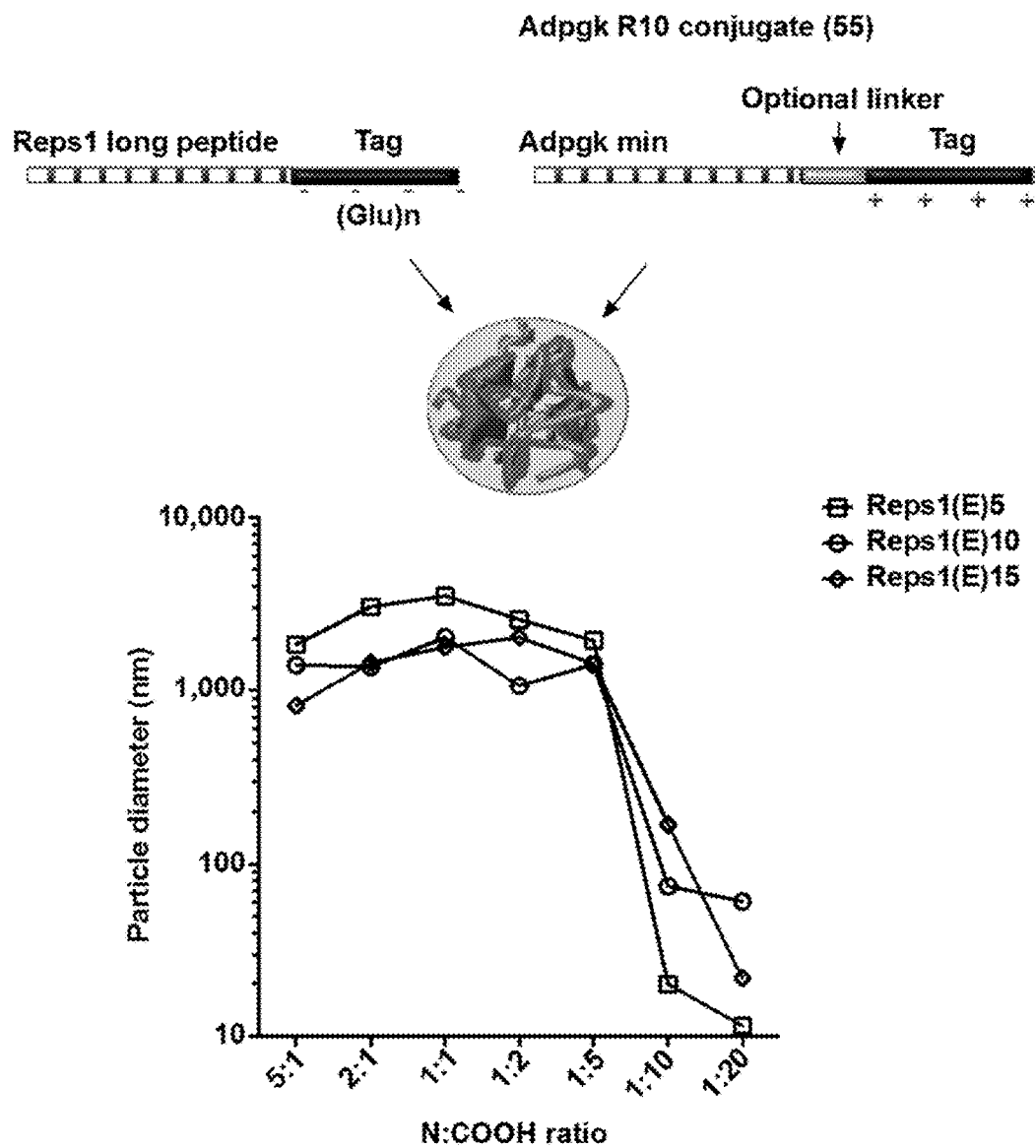

How the length of the peptide tag sequence (($Glu)_5$ (residues 1-5 of SEQ ID NO: 23), $(Glu)_{10}$ (residues 1-10 of SEQ ID NO: 23), or $(Glu)_{15}$ (SEQ ID NO: 23)) impacts the formation of polyplexes when combined with poly(cationic) polymers at different charge ratios was assessed next (FIG. 14B-14D). Unexpectedly, the optimal charge ratio to achieve 20-500 nm sized nanoparticle polyplexes was highly dependent on the cationic polymer used. The optimal charge ratio for peptide antigen conjugates utilizing a poly(Glu)$_n$ tag sequence combined with poly(Lysine)-based polymer TLR-7/8a carriers was found to be 5:1 (FIG. 14B); whereas the optimal charge ratio for peptide antigen conjugates utilizing a poly(Glu)$_n$ tag sequence combined with PEI-based polymer carriers was found to be between 1:2 and 1:5 (FIG. 14C). Next, polyplexes formed between two oppositely charged peptide antigen conjugates were evaluated; for peptide antigen conjugates utilizing a poly(Glu)$_n$ tag sequence combined with a peptide antigen conjugate utilizing an $(Arg)_{10}$ (residues 1-10 of SEQ ID NO: 3) tag sequence, the optimal charge ratio was found to be 1:10, with higher charge ratios (5:1 to 1:5) leading to formation of aggregates (FIG. 14D). Altogether, these studies identify the optimal parameters for combining peptide antigen conjugates with polymers carriers of opposite charge to ensure reliable formation of nanoparticle complexes.

Self-Assembling Nanoparticles Co-Delivering Long Peptides and TLR-7/8a Enhance CTL Responses The prior studies established that peptide antigens linked to peptide tag sequences comprised of 5 or more glutamic acid residues can be used to ensure (1) peptide solubility during manufacturing and (2) promote reliable nanoparticle polyplex formation when combined with a cationic polymer TLR-7/8a carrier at a specific charge ratio. The next studies focused on using peptide antigen conjugates linked to 10 glutamic acid (($Glu)_{10}$, (residues 1-10 of SEQ ID NO: 23)) residues as this is of sufficient length to ensure water solubility of nearly any peptide neoantigen and provides sufficient charge density to ensure a stable interaction with oppositely charged polymers. The peptide antigen conjugates using 10-mer glutamic acid tags were then complexed at a 5:1 (N:COOH) charge ratio with PLK-based carriers of TLR-7/8a using the optimal parameters identified in the prior studies.

Figure 15A:
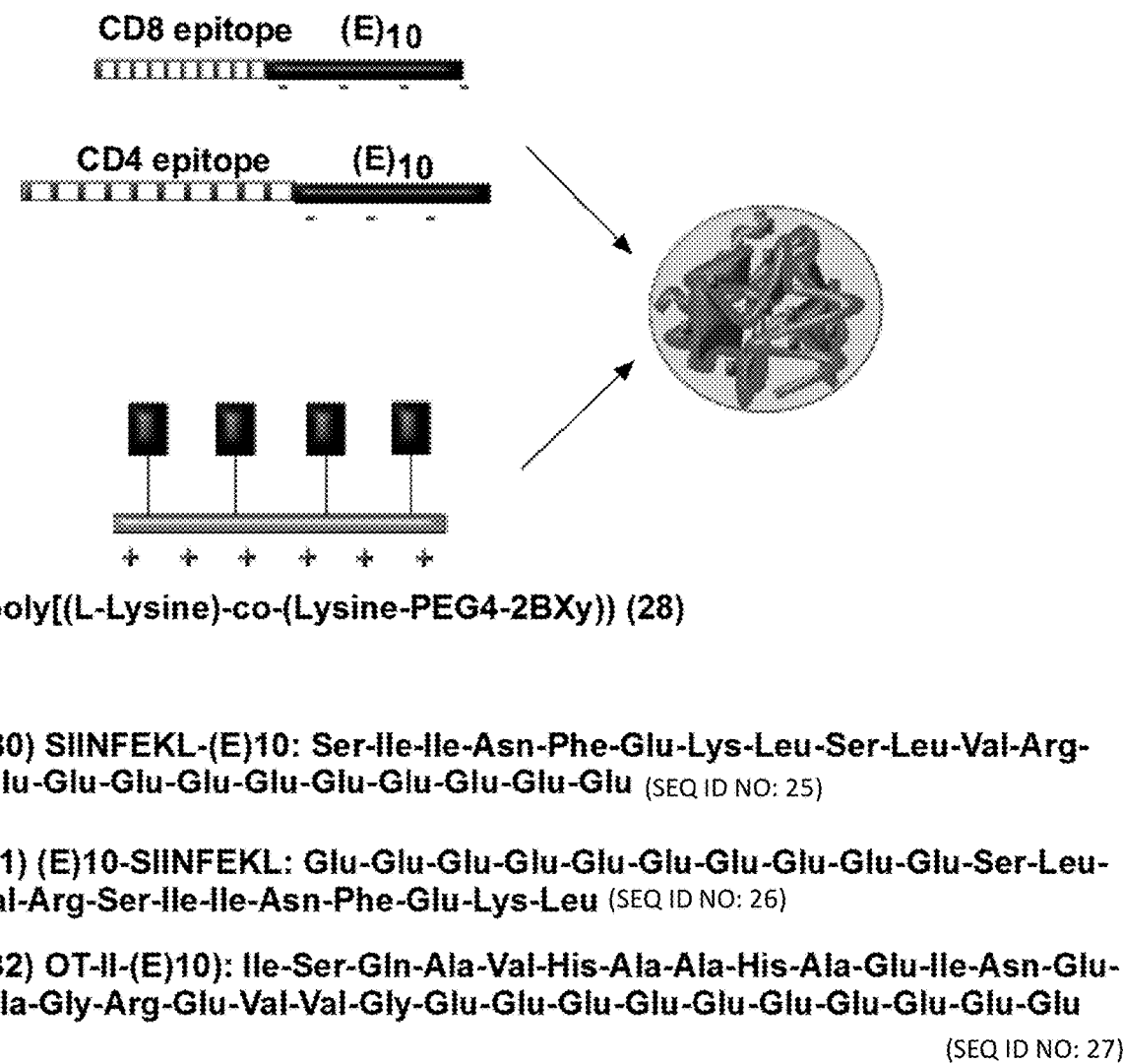
Figure 15B:
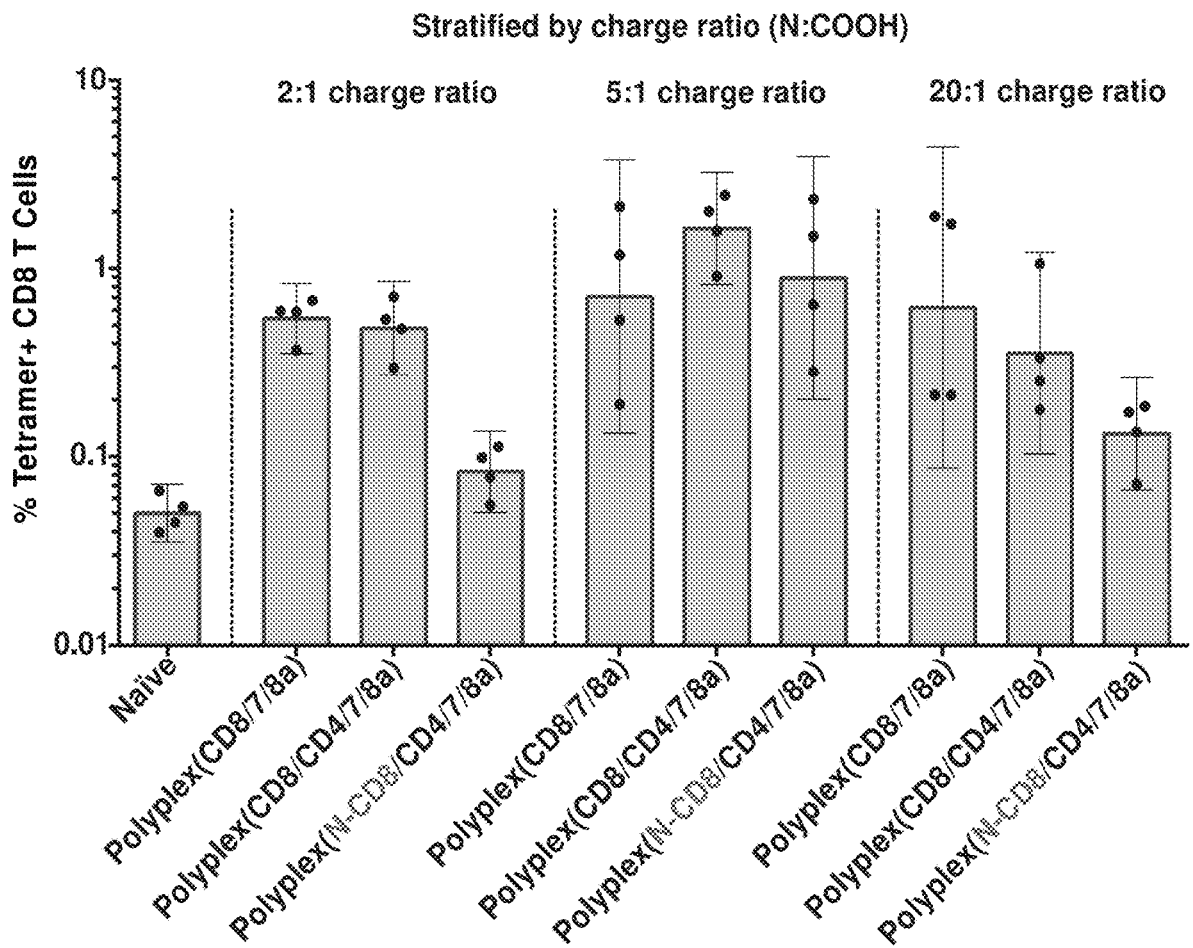

A systematic evaluation of how different properties of the nanoparticle polyplexes influence T cell responses to a model CTL epitope, SIINFEKL (SEQ ID NO: 1) (FIG. 15). The molar charge ratio (i.e., mol NH3+: mol COO—) had the largest impact on CTL responses induced by the polyplexes carrying a minimal epitope and was found to be optimal at a ratio of 5:1 (FIGS. 15B and 15C). Though attachment of the $(Glu)_{10}$ tag to the CTL epitope at either the N- or C-terminus elicited CTL responses above background, placing the $(Glu)_{10}$ tag at the C-terminus resulted in nearly 3-fold higher responses as compared with polyplexes delivering the minimal epitope with an N-terminal $(Glu)_{10}$ tag (FIG. 15C). Including a CD4 T helper epitope did not impact the magnitude of CD8 T cell responses elicited (FIG. 15D). Finally, as prior studies have shown that co-delivering TLRa with protein antigen can improve antigen cross-presentation, whether co-delivering TLR-7/8a within the polyplex or admixing the polyplex with TLR-7/8a led to higher magnitude CTL responses was evaluated. Strikingly, co-delivering TLR-7/8a within the polyplex led to significantly (~5-fold) higher magnitude responses as compared with polyplexes simply mixed with adjuvants (FIGS. 16A and 16B).

How the composition of the polymer carrier (PEI versus PLK) and co-complexation with a poly(anion), sodium alginate, impacts immune activity was investigated next (FIG. 17). Interestingly, it was found that the composition of the polymer-TLR-7/8a carrier and the addition of a poly (anion) to coat the surfaces of preformed polyplexes had no impact on the magnitude of CTL responses elicited (FIG. 17). As the use of Alginate unexpectedly had no deleterious impact on immune responses, the coating of the pre-formed peptide/PEI polyplexes with alginate may be an effective approach for ensuring nanoparticle polyplex formation through co-complexation.

Enhanced Tumor Clearance by Self-Assembling Nanoparticles Co-Delivering Long Peptides and TLR-7/8a The functional capacity of the CD8$^+$ T cells elicited by the nanoparticle polyplexes was assessed in both prophylaxis and tumor treatment models by challenging mice with B16 melanoma cells expressing full-length Ovalbumin. Consistent with the prior findings, co-delivery of the TLR-7/8a and minimal epitope within the same nanoparticle polyplex led to significantly higher CTL responses and improved survival in the prevention and treatment of tumors (FIGS. 18A-18E). While the polyplex vaccine alone provided only modest improvements in survival when used for the treatment of established tumors, the combination of the polyplex with the immune checkpoint inhibitor (CPI), anti-PD1, led to significant reductions in survival and even cured 30% of treated mice (FIG. 19A-19C).

Improved Breadth of CD8 T Cell Responses to Tumor Neoantigens by Self-Assembling Nanoparticles Co-Delivering Long Peptides and TLR-7/8a Also, the ability of the nanoparticle polyplex to elicit T cell responses against the minimal epitope of the Irgq neoantigen, which has been previously reported to be non-immunogenic, was assessed. Consistent with the findings above, it was observed that the native Irgq long peptide neoantigen is non-immunogenic, but that delivering the minimal Irgq epitope within the context of an insoluble peptide or as a minimal epitope within a nanoparticle polyplex co-delivering TLR-7/8a leads to high magnitude CTL responses (FIG. 15).

Formation of Nanoparticle Polyplexes Through Electrostatic Complexation of Positively Charged Peptides Neoantigen Conjugates with Anionic Polymers The prior studies determined the optimal parameters for combining peptide antigen conjugates, comprised of peptide antigens linked to negatively charged peptide tag sequences, with cationic polymer carriers of TLR-7/8a to form stable nanoparticle complexes that elicit high magnitude CD8 T cell responses against weakly immunogenic epitopes. The next studies sough to evaluate optimal parameters for delivering positively charged peptide antigen conjugates, comprised of peptide antigens linked to positively charged peptide tag sequences, with anionic polymers.

Peptide tag sequences, comprised of charged amino acid residues, can be added to synthetic peptide antigens during solid-phase peptides synthesis or in solution. The advantage of linking the peptide tag sequence to the peptide antigen, via an optional linker, is that shorter peptide sequences can be produced on the solid-phase resin thereby preventing sequence truncation or other potential problems associated with the generation of longer peptide sequences by solid-phase synthesis. Accordingly, we prepared a series of peptide-based minimal epitopes linked to a peptide linker sequence (SLVR, SEQ ID NO: 19) that was linked to a C-terminal azide-bearing amino acid, Lys(N3) through solid-phase peptide synthesis. The peptide antigen-Ser-Leu-Val-Arg-Lys(N3) (SEQ ID NO: 24, "Lys(N3)" refers to azidolysine) was then cleaved from the resin, isolated and then reacted to a peptide tag sequence, DBCO-(R)10 (37), comprised of a dibenzyl cyclo-ocytne (DBCO) molecule linked to a PEG linker that was linked to a poly(arginine) sequence (FIG. 21A). As a proof-of-concept of this approach, 10 unique peptide neoantigens were linked to DBCO-(R)10, and the resulting conjugates (Table 3) were characterized for purity and identity by LC-MS as well as the capacity to form polyplexes (FIG. 21) and induce CD8 T cell responses (FIG. 22).

The next series of studies used a model peptide antigen conjugate, Adpgk-(R)10 (compound 53) to evaluate the optimal charge ratio for combination with different anionic polymers. Sodium alginate was selected as a representative anionic polysaccharide; a nucleic acid oligomer, CpG ODN 1826, was selected as a representative polyphoshoester, which also has adjuvant properties; poly(methacrylic acid) (PMA) was selected as a representative acrylate-based polymer; and, poly(L-glutamic acid) (PLE) was chosen as a representative negatively charged poly(amino acid).

The optimal charge ratio was found to be highly dependent on the type of poly(anion) used (FIG. 21B).

One potential challenge is that the length of the peptide antigen tag sequence may limit the strength of the interaction of the peptide antigen conjugate with the polymer backbone. There are several potential strategies to overcome this challenge: (1) hydrophobic molecules, such as aromatic molecules that can undergo pi-stacking, can be placed on either or both the peptide antigen tag sequence and the polymer backbone as a means of strengthening the stability of the polyplexes; (2) the length of the peptide tag sequence and polymers can be increased to increase the surface area of interaction between any two molecules; and/or, the peptide antigen conjugates can be co-complexed with two oppositely charged polymers. As a proof-of-concept for the co-complexation approach, the Adpgk-(R)10 peptide antigen conjugates was dissolved in DMSO with different mass ratios (0.5, 1.0 and 3.0 equivalents) of 25 kDa linear PEI, which was then suspended in PBS pH 7.4 and then combined with Alginate to form polplexes that were characterized by DLS (FIG. 21C). Notably, 1 mass equivalent (normalized for mass of the peptide antigen conjugate) provide the optimal conditions for stable nanoparticle formation, which was observed across a broad range of charge ratios, ranging from 2:1 to 1:5 (N:COOH) (FIG. 21C).

Polyplexes Using Positively Charged Peptide Antigen Conjugates Complexed to Poly(Anions) Expand the Breadth of CD8 T Cell Responses to Peptide-Based Neoantigens The next studies evaluated the immunogenicity of different peptide-based neoantigens derived from the MC38 tumor cell line that were linked to a positively charged peptide tag (compound 37). The positively charged peptide antigen conjugates (Table 3) were either complexed with the poly(anion) alginate at a 1:5 charge ratio (N:COOH) and either mixed with adjuvant (groups 2 and 3) or co-complexed with a poly(cationic) carrier of TLR-7/8a (groups 4 and 5); alternatively, the positively charged peptide antigen conjugates were complexed with a poly(anion) adjuvant, CpG at a charge ratio of 5:1 (FIG. 22). Mice were immunized with the resulting polyelectrolyte complexes and CD8 T cell responses to 10 unique peptide-based neoantigens were assessed on day 6 (FIG. 22). The summed responses in vaccinated mice (groups 2-6) were all greater than the summed responses (<0.25% of total CD8 T cells) observed in the naïve group. Notably, responses were highest when the adjuvant was co-delivered with the peptide antigen conjugate in the nanoparticle (Groups 3-6). Altogether, these results indicate that electrostatic complexation of peptide antigen conjugates is a generalizable approach for generating immunogenic compositions that can elicit CD8 T cell responses against a broad array of different peptide-based neoantigens.

Synthesis of Conjugatable TLR-7/8a and Peptide TLR-7/8a Conjugates

Several conjugatable TLR-7/8a were prepared to permit linkage to peptide antigen conjugates or to polymers that form nanoparticle polyplexes with the peptide antigen conjugates. These TLR-7/8a use a linker site that does not interfere with TLR-7/8 binding and, therefore, permits immediate onset immune activity. The synthesis, purification and characterization of these compounds are described below.

Synthesis of compounds 5, 6 and 11-14 were carried out as previously described with slight modifications (See Shukla et al., *J Med Chem* 53, 4450-4465 (2010); Nanba, R. J., Iizuka, Takao (JP), Ishii, Takeo (JP) (TERUMO CORP (JP), 1999); Shukla et al., *Bioorg Med Chem Lett* 20, 6384-6386 (2010); Lynn, G. M. et al., *Nat Biotechnol* 33, 1201-1210 (2015); each of which is incorproated by reference herein).

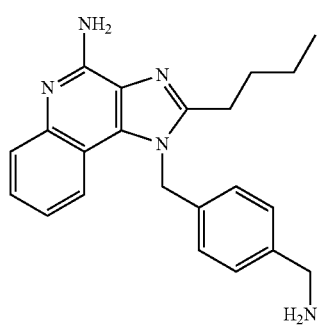

(5)

Compound (5) 1-(4-(aminomethyl)benzyl)-2-butyl-1H-imidazo[4,5-c]quinolin-4-amine $^1$H NMR (400 MHz, DMSO-d6) δ 7.77 (dd, J=8.4, 1.4 Hz, 1H), 7.55 (dd, J=8.4, 1.2 Hz, 1H), 7.35-7.28 (m, 1H), 7.25 (d, J=7.9 Hz, 2H), 7.06-6.98 (m, 1H), 6.94 (d, J=7.9 Hz, 2H), 6.50 (s, 2H), 5.81 (s, 2H), 3.64 (s, 2H), 2.92-2.84 (m, 2H), 2.15 (s, 2H), 1.71 (q, J=7.5 Hz, 2H), 1.36 (q, J=7.4 Hz, 2H), 0.85 (t, J=7.4 Hz, 3H). MS (APCI) calculated for $C_{22}H_{25}N_5$ m/z 359.2, found 360.3 (M+H)$^+$.

Compound (11) is a conjugatable TLR-7/8a with a terminal thiol group that permits attachment to polymer, for example, through thiol-exchange or Michael-addition reactions.

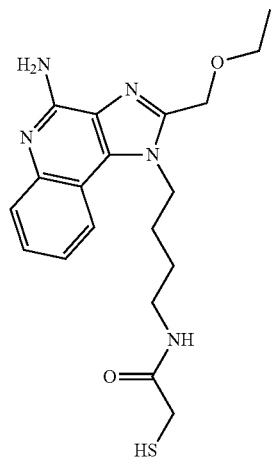

(11)

Synthesis of the precursor to compound (11), 1-(4-aminobutyl)-2-(ethoxymethyl)-1H-imidazo[4,5-c]quinolin-4-amine, was carried out as previously described by Lynn, G. M. et al., *Nat Biotechnol* 33, 1201-1210 (2015). To 100 mg of 1-(4-aminobutyl)-2-(ethoxymethyl)-1H-imidazo[4,5-c]quinolin-4-amine (0.32 mmol, 1 eq) in 5 mL of methanol was added 115 g of S-acetyl thioglycolic acid pentafluorophenyl ester (0.38 mmol, 1.2 eq) while stirring vigorously. The reaction was complete after 1 hour and then evaporated to dryness to obtain yellow oil that was loaded onto a silica column and purified on a flash system using a gradient of 2-10% methanol in DCM. The intermediate, 47.3 mg (34% yield) was isolated as a spectroscopically pure (>95% at 254 nm) white solid. The acetyl-protecting group was then removed by adding the intermediate to methanol under argon gas followed by the addition of 0.2 molar equivalents of $K_2CO_3$. The deprotected thiol compound was then immediately used for conjugation. MS (APCI) calculated for $C_{19}H_{25}N_5O_2S$ m/z 387.17, found 388.2 (M+H)$^+$ Compound (12) is a conjugatable TLR-7/8a with a terminal thiol group that permits attachment to polymer, for example, through thiol-exchange or Michael-addition reactions.

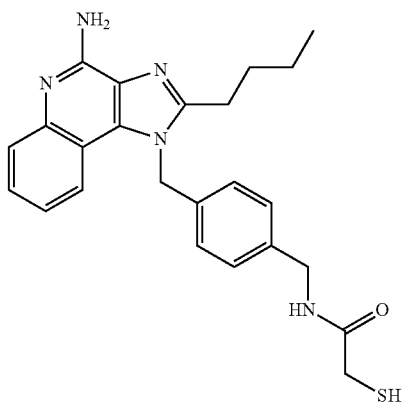

(12)

Synthesis of compound (12) was the same as for compound 11. (APCI) calculated for $C_{24}H_{27}N_5OS$ m/z 433.19, found 434.3 (M+H)$^+$.

Compound (13) is a conjugatable TLR-7/8a with a terminal azide group that permits attachment to polymers or peptide antigen conjugates, for example, through "click chemistry" reactions.

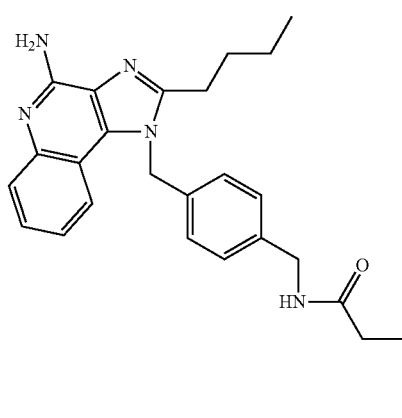

(13)

Synthesis of compound (13). To 2 mL of ethyl acetate was added 100 mg (0.28 mmol, 1 eq) of compound (5), 50 mg (0.14 mmol, 1 eq) of CDMT and 22 mg (0.15 mmol, 1.1 eq) of Azidopentanoic acid, followed by the dropwise addition of 20 μl (0.17 mmol, 1.2 eq) of NMM, while stirring vigorously. After 16 hours at room temperature, the reaction mixture was filtered and then washed 3×50 mL with 1 M HCl. The organic phase was dried with Na₂SO₄ and then evaporated to dryness. The resulting solid was purified by reverse phase HPLC chromatography using a 15-45% acetonitrile/H₂O (0.05% TFA) gradient over 15 minutes. The resulting fractions were collected, frozen and lyophilized to obtain a spectroscopically pure (>95% at 254 nm) white solid. MS (APCI) calculated for $C_{27}H_{32}N_8O$ m/z 484.3, found 485.3 $(M+H)^+$.

Compound (14) is a conjugatable TLR-7/8a with an enzyme-degradable tetrapeptide (Lys-Pro-Leu-Arg) linker. The Lys-Pro-Leu-Arg peptide is recognized and hydrolyzed by cathepsin proteases localized to endosomal compartments of cells.

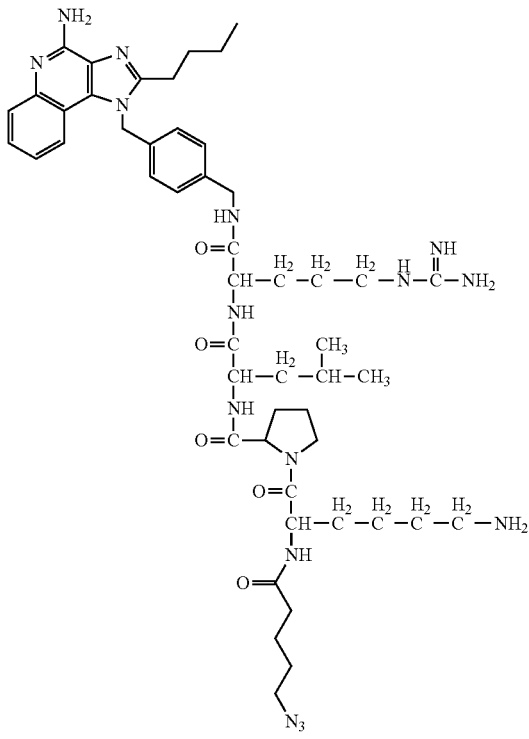

(14)

Synthesis of compound (14). To 2 mL of ethyl acetate was added 20 mg (0.055 mmol, 1.1 eq) of (5), 9 mg (0.061 mmol, 1 eq) of CDMT and 50 mg (0.051 mmol, 1 eq) of an azide-terminated tetrapeptide with protected side groups (X-Lys-Pro-Leu-Arg-COOH (SEQ ID NO: 17), where x=azido-pentanoic acid) and a free acid C-terminus, followed by the dropwise addition of 20 μl (0.17 mmol, 1.2 eq) of NMM, while stirring vigorously. After 16 hours at room temperature, the reaction mixture was filtered and then washed 3×50 mL with 1 M HCl. The organic phase was dried with Na₂SO₄ and then evaporated to dryness. The resulting solid was treated with 1 mL of an 88:5:5:2 solution of TFA/TIPS/Phenol/H₂O to remove the protecting groups on the side chains of the tetrapeptide. After 1 h, the reaction mixture was added to 50 mL of ethyl ether and the deprotected product (3) precipitated from solution. The resulting crude product was purified by reverse phase HPLC chromatography using a 20-55% acetonitrile/H₂O (0.05% TFA) gradient over 15 minutes (column=Zorbax SBC18 9.4×150 mm). The resulting fractions were collected, frozen and lyophilized to obtain a spectroscopically pure (>95% at 254 nm) white solid. MS (APCI) calculated for $C_{50}H_{74}N_{16}O_5$ m/z 978.6, found 979.7 $(M+H)^+$.

Synthesis of PEI-Based Carriers of TLR-7/8a

Figure 11:
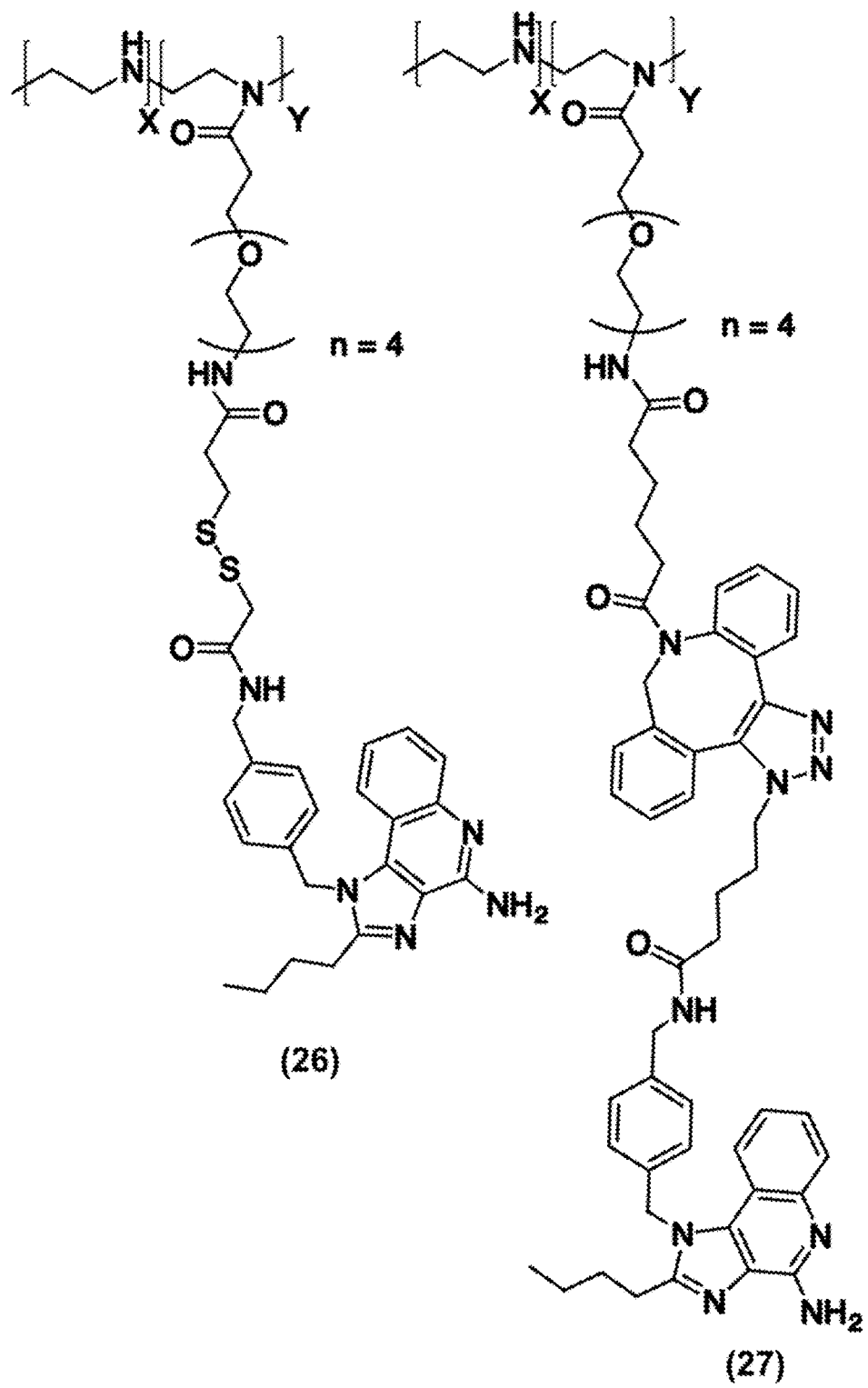
FIG. 11: Compound (12) linked to L-PEI either through a disulfide linkage (26) or through an amide bond (27).

Linear and branched PEI-based polymers were chemically modified with NHS-PEG cross-linkers bearing either thiol reactive, pyridyl disulfide (NHS-PEG4-PDS), or azide-reactive, dibenzylcyclooctyne (NHS-PEG4-DBCO) end groups to facilitate linkage to either thiol- or azide-modified TLR-7/8a (FIG. 11). The pyridyl disulfide reacts with thiol groups at room temperature and does not require the addition of a catalyst. Similarly, the DBCO group reacts with azide groups at room temperature and does not require addition of a catalyst, unlike acetylene groups that require Cu(I) to catalyze the cycloaddition reaction, thus permitting a facile strategy for attaching azide-bearing active TLR-7/8a to polymer backbones.

Synthesis of PEI-based carriers of TLR-7/8a was carried out in a simple 2-step reaction in methanol.

Example reactions used to generate PEI-based polymer carriers of TLR-7/8a are described here.

(26) To 15.4 mg of 25 kDa linear PEI (0.36 mmol NH, 1 eq) was added 5 mg of NHS-PEG4-PDS (0.009 mmol, 0.025 EQ) in 2 mL of methanol while stirring vigorously at room temperature. After 1 hour, 5.8 mg of (12) (0.013 mmol, 0.0375 eq) was added and allowed to proceed for 2 hours. The reaction mixtures was then purified by dialysis against in methanol using regenerated cellulose dialysis membranes with molecular weight cutoff of 10 kDa.

(27) To 500 μL of methanol was added 13.2 mg (308 moles, 1 eq) of 25 kDA PEI (free base) followed by addition of 5.0 mg (8 moles, 0.025 EQ) NHS-PEG4-DBCO. After 1 hour, 4.85 mg (10.4 moles, 0.033 eq) of compound (13) was added and the reaction proceeded at room temperature for 18 hours. The polymer-TLR-7/8a conjugate was then purified by dialysis in methanol and characterized for TLR-7/8a content and polymer molecular weight.

TABLE 1

PEI-based carriers of active TLR-7/8a. Note that the ligand density is the percentage of monomer units of the polymer that have TLR-7/8a attached.

| Compound # | Architecture | MW[1] (Da) | Cross-linker | Ligand | Ligand density (mol %) Actual (theoretical) |
|---|---|---|---|---|---|
| 15 | Linear PEI | 25,000 | NHS-PEG4-PDS | (11) | 0.7 (1.0) |
| 16 | Linear PEI | 25,000 | NHS-PEG4-PDS | (11) | 1.1 (2.5) |
| 17 | Linear PEI | 25,000 | NHS-PEG4-PDS | (11) | 2.1 (5) |
| 18 | Linear PEI | 25,000 | NHS-PEG4-PDS | (11) | 1.9 (10) |
| 19 | Linear PEI | 25,000 | NHS-PEG12-PDS | (11) | 1.0 (1.0) |
| 20 | Linear PEI | 25,000 | NHS-PEG12-PDS | (11) | 1.8 (2.5) |
| 21 | Linear PEI | 25,000 | NHS-PEG12-PDS | (11) | 2.6 (5) |
| 22 | Linear PEI | 25,000 | NHS-PEG12-PDS | (11) | 3.0 (10) |
| 23 | Branched PEI | 10,000 | NHS-PEG4-PDS | (11) | 1.8 (2.5) |
| 24 | Branched PEI | 10,000 | NHS-PEG4-PDS | (12) | 1.3 (2.5) |

TABLE 1-continued

PEI-based carriers of active TLR-7/8a. Note that the ligand density is the percentage of monomer units of the polymer that have TLR-7/8a attached.

| Compound # | Architecture | MW[1] (Da) | Cross-linker | Ligand | Ligand density (mol %) Actual (theoretical) |
|---|---|---|---|---|---|
| 25 | Linear PEI | 25,000 | NHS-PEG4-PDS | (12) | 1.5 (2.5) |
| 26 | Linear PEI | 25,000 | NHS-PEG4-PDS | (12) | 1.3 (2.5) |
| 27 | Linear PEI | 25,000 | PEG4-DBCO-2BXy | (13) | 2.1 (2.5) |

[1] MW of the polymer precursor used for conjugation to the PEG cross-linker and TLR-7/8a.

Synthesis of PLK-Based Carriers of TLR-7/8a

Synthesis of poly(L-lysine) (PLK)-based carriers of TLR-7/8a was carried out in a simple 2-step reaction in methanol.

Example reactions to generate PL-based polymer (compound 28) (including to compound (13), with a hydrolytically stable amide bond) and polymer (compound 29) (including compound (3), with an enzyme degradable tetrapeptide linker) are provided below. The (28) and (29) polymers include a DBCO-based chemical cross-linker.

(28) To 1 mL of 0.1 Molar HEPES (pH 8.0) was added 10 mg (48 moles, 1 EQ) of Poly(L-Lysine)·HBr, followed by addition of 1.55 mg (2.4 moles, 0.05 EQ) of NHS-PEG4-DBCO. The reaction mixture appeared cloudy but then became translucent as the cross-linker reacted with the soluble polymer. After 1 hour, 1.27 mg (2.6 moles, 0.055 EQ) of compound (13) was added and the reaction proceeded at room temperature for 18 hours. The polymer-TLR-7/8a conjugate was purified by dialysis in methanol and characterized for TLR-7/8a content and polymer molecular weight. The same procedure was carried out for (28_10%) except 4.8 and 5.2 moles of NHS-PEG4-DBCO and compound (13), respectively, were used in the reaction to produce a polymer with a higher density of the active TLR-7/8a.

(29) To 1 mL of 0.1 Molar HEPES (pH 8.0) was added 10 mg (48 moles, 1 EQ) of Poly(L-Lysine)·HBr, followed by addition of 1.24 mg (2 moles, 0.04 EQ) NHS-PEG4-DBCO. The reaction mixture appeared cloudy but then became translucent as the cross-linker reacted with the soluble polymer. After 1 hour, 2 mg (2 moles, 0.04 EQ) of compound (14) was added and the reaction proceeded at room temperature for 18 hours. The polymer-TLR-7/8a conjugate was purified by dialysis in methanol and characterized for TLR-7/8a content and polymer molecular weight.

TABLE 2

PLK-based carriers of active TLR-7/8a. Note that the ligand density is the percentage of monomer units of the polymer that have TLR-7/8a attached.

| Compound # | MW (Da) | Cross-linker | Ligand | Ligand density (mol %) Actual (theoretical) |
|---|---|---|---|---|
| 28 | 16,000 | NHS-PEG4-DBCO | (13) | 4.73 (5.0) mol % |
| 28' | 16,000 | NHS-PEG4-DBCO | (13) | 10.83 (10.0) mol % |
| 29 | 16,000 | NHS-PEG4-DBCO | (14) | 3.55 (4.0) mol % |

[1] MW of the polymer precursor used for conjugation to the PEG cross-linker and TLR-7/8a.

Synthesis of Peptide Antigen Conjugates

Peptide antigen conjugates, comprised of peptide antigens linked to a tag via an optional linker can be synthesized by solid-phase peptide synthesis or by linking a peptide antigen, which is synthesized by solid-phase peptide synthesis, to a tag off-resin in solution phase. Both schemes were used to generate the peptide antigen conjugates summarized in Table 3, below.

Peptide antigen conjugates, compounds 30 through 36, were prepared entirely by solid-phase peptide synthesis, followed by purification by HPLC. Peptide antigen conjugates, compounds 39, 41, 43, 45, 47, 49, 51, 53, 55, 57, 59 and 61 by coupling a DBCO-modified peptide tag sequence, comprising 10 Arginine residues, DBCO-(R) 10 to the C-terminal non-natural amino acid residue Lys(N3), X, of peptide antigens 38, 40, 42, 44, 46, 48, 50, 52, 54, 56, 58 and 60, respectively.

TABLE 3 peptide antigen conjugates

| Compound # | Relevant peptide sequence and conjugate | Relevant SEQ ID NO | MW Da |
|---|---|---|---|
| 30 | SIINFEKLSLVREEEEEEEEE | 25 | 2710.0 |
| 31 | EEEEEEEEEESLVRSIINFEKL | 26 | 2710.0 |

TABLE 3 -continued peptide antigen conjugates

| Compound # | Relevant peptide sequence and conjugate | Relevant SEQ ID NO | MW Da |
|---|---|---|---|
| 32 | ISQAVHAAHAEINEAGREVVGEEEEEEEEEE | 27 | 3449.5 |
| 33 | AALLNSAVLGAAPEEEEEEEEEE | 28 | 2459.6 |
| 34 | GRVLELFRAAQLANDVVLQIMELCGATREEEEE | 29 | 3732.9 |
| 35 | GRVLELFRAAQLANDVVLQIMELCGATREEEEEEEEEE | 30 | 4377.2 |
| 36 | GRVLELFRAAQLANDVVLQIMELCGATREEEEEEEEEEEEEEE | 31 | 5021.4 |
| 37 | DBCO-(R)10 | 32 | 2515.0 |
| 38 | KSFHFYCPLSLVRK' | 33 | 1750.1 |
| 39 | KSFHFYCPLSLVRK'-(37) | 34 | 4265.1 |
| 40 | QIYAFLQGFSLVRK' | 35 | 1695.0 |
| 41 | QIYAFLQGFSLVRK'-(37) | 36 | 4210.0 |
| 42 | VATINFRRLSLVRK' | 37 | 1698.0 |
| 43 | VATINFRRLSLVRK'-(37) | 38 | 4213.0 |
| 44 | AWLSKVSRLSLVRK' | 39 | 1668.0 |
| 45 | AWLSKVSRLSLVRK'-(37) | 40 | 4183.0 |
| 46 | IMTQHLEPISLVRK' | 41 | 1690.0 |
| 47 | IMTQHLEPISLVRK'-(37) | 42 | 4205.0 |
| 48 | SSSVLFEYMSLVRK' | 43 | 1670.9 |
| 49 | SSSVLFEYMSLVRK'-(37) | 44 | 4185.9 |
| 50 | AALLNSAVLGSLVRK' | 45 | 1536.7 |
| 51 | AALLNSAVLGSLVRK'-(37) | 46 | 4051.7 |
| 52 | AALLNSAVLRK' | 47 | 1180.2 |
| 53 | AALLNSAVLRK'-(37) | 48 | 3695.2 |
| 54 | ASMTNMELMSSLVRK' | 49 | 1723.1 |
| 55 | ASMTNMELMSSLVRK'-(37) | 50 | 4238.1 |
| 56 | MAPIDHTTMSSLVRK' | 51 | 1712.0 |
| 57 | MAPIDHTTMSSLVRK'-(37) | 52 | 4227.0 |
| 58 | SSPYSLHYLSSLVRK' | 53 | 1762.0 |
| 59 | SSPYSLHYLSSLVRK'-(37) | 54 | 4277.0 |
| 60 | AKFVAAWTLKAAA-SLVRK' | 55 | 3240.8 |
| 61 | AKFVAAWTLKAAA-SLVRK'-(37) | 56 | 5755.8 |
| 62 | 2BXy-(R)10 | 57 | 2999.3 |

In Table 3, K' refers to azidolysine.
The "(37)" structure is shown in in FIG. 21A.

Formulation of Nanoparticle Polyplexes

Immunogenic compositions comprised of nanoparticles polyplexes that are comprised of peptide antigens electrostatically complexed with polymers of opposite charge are generated through charge neutralization.

The charge of a compound is estimated based on the pKa of the acidic and basic residues that comprise the compound and is therefore dependent on the pH of the solution in which the compound is dispersed. The pH of the solutions used for formulation of the nanoparticle polyplexes described herein is about pH 7.4 and is used as the basis for estimating the charge of the positively or negatively charged compounds described herein. Certain compounds, such as tetra-alkyl-ammonium species, carry a permanent positive charge and are not dependent on the pH. The conjugate based of strong acids, such as sulfates and phosphates effectively carry a permanent negative charge in aqueous conditions due to their low pKa values.

The charge of a peptide antigen conjugate is determined by calculating the net charge of the peptide antigen conjugate assuming pH 7.4. The C-terminus as well as glutamic and aspartic acid residues are considered to be negatively charged at pH 7.4, whereas the N-terminus, lysine and arginine residues are considered to be positively charged at pH 7.4. The net charge of the peptide antigen conjugate is determined by summing the charge of all charged residues comprising the peptide antigen conjugate. For a given mass of peptide antigen, a molar amount of charge can be calculated based on the estimated net charge and the known molecular weight. Based on the estimated molar amount of charge, the amount of compound with an opposing charge can be determine to achieve the desired charge ratio.

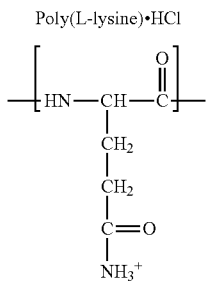

1 mole charge/164.04 g

Example: Formulation of peptide antigen conjugate, compound 30, with poly(L-Lysine)·HCl using a charge ratio of 5:1 (N:C). First, the net charge of compound 30 is determined by summing the positively and negatively charged groups at pH 7.4 and is estimated to have a net charge of −9.0. In other words there are −9.0 moles of charge for every 2207.9 g of this material, which gives a molar charge ratio of 0.0041 moles charge/g of compound 30. To prevent aggregation of the nanoparticle polyplexes, the peptide antigen conjugates were typically suspended at a final concentration of 1 mg/mL or less in PBS pH 7.4 prior to combining with the polymer of opposite charge. Thus, in this example, 1 mg of compound 30 would be suspended in 500 µL of PBS to give a 2 mg/mL solution of compound 30. To determine the amount of poly(L-lysine)·HCl that is required to give a charge ratio of 5:1, the moles of charge for 1 mg of compound 30 is multiplied by a factor of 5 (5 moles of N per 1 mole of COOH; 5 to 1 charge ratio) and then divided by the molar charge ratio for poly(L-lysine)·HCl, which is 1 mole charge (NH3+) per 164.04 g.

Thus:

$$1 \text{ mg compound 30} \times \frac{0.0041 \text{ moles } (-) \text{ charge}}{\text{g of compound 30}} \times$$

$$\frac{5 \text{ moles of } (+) \text{ charge}}{1 \text{ mol } (-) \text{ charge}} \times \frac{164.04 \text{ g poly}(L\text{-Lysine})\cdot\text{HCl}}{1 \text{ mole of } (+) \text{ charge}} =$$

3.3 mg of poly(L-lysine)·HCl

The 3.3 mg of poly(L-lysine)·HCl would be suspended in a volume of 1.65 mL of PBS to give 2 mg/mL poly(L-lysine)·HCl. To generate polyplexes of compound 30 and poly(L-lysine)·HCl at a 5:1 charge ratio, the 1.65 mL of 2 mg/mL poly(L-lysine)·HCl would be added to the 500 µL solution of compound 30 at 2 mg/mL while stirring vigorously. The resulting polyplexes would then be characterized by dynamic light scattering to assess particle size of the resulting polyplexes.

REFERENCES

1. Platten, M. & Offringa, R. *Cell Res* 25, 887-888 (2015).
2. Chen, D. S. & Mellman, I. *Immunity* 39, 1-10 (2013).
3. Le, D. T. et al. *N Engl J Med* 372, 2509-2520 (2015).
4. Snyder, A. et al. *N Engl J Med* 371, 2189-2199 (2014).
5. van Rooij, N. et al. *J Clin Oncol* 31, e439-442 (2013).
6. Tran, E. et al. *Science* 344, 641-645 (2014).
7. Lu, Y. C. et al. *Clin Cancer Res* 20, 3401-3410 (2014).
8. Tran, E. et al. *Science* 350, 1387-1390 (2015).
9. Castle, J. C. et al. *Cancer Res* 72, 1081-1091 (2012).
10. Yadav, M. et al. *Nature* 515, 572-576 (2014).
11. Kreiter, S. et al. *Nature* 520, 692-696 (2015).
12. Linnemann, C. et al. *Nature medicine* 21, 81-85 (2015).
13. Schumacher, T. N. & Schreiber, R. D. *Science* 348, 69-74 (2015).
14. Barouch, D. H. et al. *Vaccine* 29, 5203-5209 (2011).
15. Roberts, D. M. et al. *Nature* 441, 239-243 (2006).
16. Ulmer, J. B., Valley, U. & Rappuoli, R. *Nat Biotechnol* 24, 1377-1383 (2006).
17. Brito, L. A. & O'Hagan, D. T. *Journal of controlled release: official journal of the Controlled Release Society* 190C, 563-579 (2014).
18. Coffman, R. L., Sher, A. & Seder, R. A. *Immunity* 33, 492-503 (2010).
19. Hensley, S. E. et al. *Mol Ther* 15, 393-403 (2007).
20. Hyde, S. C. et al. *Nat Biotechnol* 26, 549-551 (2008).
21. Perez, S. A. et al. *Cancer* 116, 2071-2080 (2010).
22. Aranda, F. et al. *Oncoimmunology* 2, e26621 (2013).
23. Noguchi, M. et al. *Cancer Immunol Immunother* (2016).
24. Rosario, M. et al. *Eur J Immunol* 40, 1973-1984 (2010).
25. Sabbatini, P. et al. *Clin Cancer Res* 18, 6497-6508 (2012).
26. Bijker, M. S. et al. *J Immunol* 179, 5033-5040 (2007).
27. Bijker, M. S. et al. *Eur J Immunol* 38, 1033-1042 (2008).
28. Zhang, H. et al. *J Biol Chem* 284, 9184-9191 (2009).
29. Rosalia, R. A. et al. *Eur J Immunol* 43, 2554-2565 (2013).
30. Perrie, Y., Mohammed, A. R., Kirby, D. J., McNeil, S. E. & Bramwell, V. W. *Int J Pharm* 364, 272-280 (2008).
31. Bachmann, M. F. & Jennings, G. T. *Nat Rev Immunol* 10, 787-796 (2010).
32. Dubensky, T. W., Jr. & Reed, S. G. *Seminars in immunology* 22, 155-161 (2010).
33. Lynn, G. M. et al. *Nat Biotechnol* 33, 1201-1210 (2015).
34. Liu, H. et al. *Nature* 507, 519-522 (2014).
35. Dane, E. L. & Irvine, D. J. *Nat Biotechnol* 33, 1146-1148 (2015).

It will be apparent that the precise details of the methods or compositions described may be varied or modified without departing from the spirit of the described embodiments. We claim all such modifications and variations that fall within the scope and spirit of the claims below.

The invention claimed is:

1. An immunogenic composition for inducing an immune response to a peptide antigen in a subject, the immunogenic composition comprising polymer nanoparticles, the polymer nanoparticles comprising:
    a first polymer linked to a conjugate by an electrostatic interaction, the conjugate comprising the peptide antigen linked to a peptide tag; and
    optionally an adjuvant; and
wherein
    the electrostatic interaction is between the first polymer and the peptide tag;
    the first polymer comprises a net negative charge and the peptide tag comprises a net positive charge at pH 7.4;
    the peptide antigen from 8-12 amino acids in length or from 29-35 amino acids in length;
    the peptide antigen and the conjugate are soluble in phosphate buffered saline at pH 7.4;
    the peptide tag is C-terminal to the peptide antigen in the conjugate;
    the peptide tag comprises 5 to 15 amino acids; and
    wherein, when present, the adjuvant is a toll-like receptor 7/8 agonist and is linked to the first polymer through an amide bond; and a ratio of the adjuvant to monomer of the first polymer is from 1:100 to 1:10 mol/mol; and
    wherein the polymer nanoparticles enter immune cells under physiological conditions to induce the immune response to the peptide antigen in the subject.

2. The immunogenic composition of claim 1, wherein the peptide antigen is linked to the peptide tag by a linker.

3. The immunogenic composition of claim 2, wherein the linker is a cathepsin-cleavable peptide linker.

4. The immunogenic composition of claim 1, wherein the peptide tag comprises from 1 to 5 aromatic amino acids.

5. The immunogenic composition of claim 4, wherein the aromatic amino acid is selected from tryptophan, phenylalanine, tyrosine, histidine or glutamic acid gamma-benzyl ester.

6. The immunogenic composition of claim 1, wherein the peptide tag consists of 10 lysine residues.

7. The immunogenic composition of claim 1, wherein the ratio of the net charge of the first polymer to the net charge of the conjugate in the polymer nanoparticle at pH 7.4 is from about 20:1 to about 1:20 mol/mol.

8. The immunogenic composition of claim 1, wherein the first polymer is a
    sodium alginate, negatively charged nucleic acid sequence, poly(methacrylic acid) or poly(L-glutamic acid).

9. The immunogenic composition of claim 1, wherein:
    (a) the first polymer is a sodium alginate polymer, and a negative to positive charge ratio of the net charge of the conjugate to the net charge of the first polymer is from about 5:1 to about 2:1 mol/mol, or from about 1:10 to about 1:20 mol/mol;
    (b) the first polymer is a nucleic acid polymer, and a negative to positive charge ratio of the net charge of the conjugate to the net charge of the first polymer is from about 5:1 to about 2:1 mol/mol, or from about 1:10 to about 1:20 mol/mol; or
    (c) the first polymer is a poly(methacrylic acid) polymer, and a negative to positive charge ratio of the net charge of the conjugate to the net charge of the first polymer is from about 1:5 to about 1:10 mol/mol;
    (d) the first polymer is a poly(L-glutamic acid) polymer, and a negative to positive charge ratio of the net charge of the conjugate to the net charge of the first polymer is from about 1:5 to about 1:10 mol/mol.

10. The immunogenic composition of claim 1, further comprising a second polymer, wherein the second polymer is a poly(cationic) polymer that comprises a net electrostatic charge that is opposite to that of the first polymer.

11. The immunogenic composition of claim 10, wherein a negative to positive charge ratio of the net charge of the conjugate and the second polymer to the net charge of the first polymer is from about 1:5 to about 1:10, or about 2:1 mol/mol.

12. The immunogenic composition of claim 1, comprising the adjuvant, wherein the adjuvant is linked to the first polymer through an amide bond and wherein the adjuvant is a toll-like receptor 7/8 agonist.

13. The immunogenic composition of claim 12, wherein:
the first polymer sodium alginate polymer and a ratio of adjuvant to monomer of the first polymer is from 1:100 to 1:10 mol/mol;
the first polymer is poly(methacrylic acid) polymer and a ratio of adjuvant to monomer of the first polymer is from 1:100 to 1:10 mol/mol; or
the first polymer is poly(L-glutamic acid) polymer and a ratio of adjuvant to monomer of the first polymer is from 1:100 to 1:10 mol/mol.

14. The immunogenic composition of claim 1, wherein the first and/or second polymer comprises a plurality of monomers comprising from 5 monomers to 500 monomers.

15. The immunogenic composition of claim 1, wherein the antigen is a tumor associated peptide antigen, a viral peptide antigen, a bacterial peptide antigen, or a protozoan peptide antigen.

16. The immunogenic composition of claim 1, wherein the first polymer linked to the conjugate, and the adjuvant, and, if present, the second polymer, self-assemble into the polymer nanoparticles in phosphate buffered saline, pH 7.4.

17. The immunogenic composition of claim 1, wherein the polymer nanoparticles are from about 20 to about 200 nm in diameter.

18. The immunogenic composition of claim 1, wherein the polymer nanoparticles comprise from about 5 to about 10 different peptide antigen conjugates.

19. The immunogenic composition of claim 1, wherein the polymer nanoparticles are polyplex nanoparticles.

20. The immunogenic composition of claim 7, wherein the ratio of the net charge of the first polymer to the net charge of the conjugate in the polymer nanoparticle is from 4:1 to 6:1 mol/mol.

21. The immunogenic composition of claim 20, wherein the ratio of the net charge of the first polymer to the net charge of the conjugate in the polymer nanoparticle is about 5:1 mol/mol.

22. The immunogenic composition of claim 12, wherein the ratio of adjuvant to monomer of the first polymer is from 1:20 to 1:10 mol/mol.

23. The immunogenic composition of claim 1, wherein the peptide antigen is from a tumor associated antigen or a tumor neoantigen comprising an amino acid mutation not present in non-cancerous cells, and wherein the peptide antigen comprises 10-20 amino acids flanking the amino acid mutation of the tumor associated antigen or a tumor neoantigen.

24. The immunogenic composition of claim 1, wherein the peptide tag comprises from 5 to 15 aspartic acid or glutamic acid residues.

25. A method of inducing an immune response in a subject to a peptide antigen, comprising administering an effective amount of the immunogenic composition of claim 1 to the subject, thereby inducing the immune response.

26. The method of claim 25, comprising administering the immunogenic composition to a target location in the subject.

27. The method of claim 25, comprising intravenous administration of the immunogenic composition to the subject.

* * * * *

SEQUENCE LISTING

<160> NUMBER OF SEQ ID NOS: 63

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Ile Ile Asn Phe Glu Lys Leu
1               5

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Lys Lys Lys Lys Lys Lys Lys Lys Lys Lys Lys Lys Lys Lys Lys Lys
1               5                   10                  15

Lys Lys Lys Lys
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Arg Arg Arg Arg Arg Arg Arg Arg Arg Arg Arg Arg Arg Arg Arg Arg
1               5                   10                  15

Arg Arg Arg Arg
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

Lys Lys Lys Lys Lys Lys Lys Lys Lys Lys Lys Lys Lys Lys Lys Lys
1               5                   10                  15

Lys Lys Lys Lys Trp Trp
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Lys Lys Lys Lys Lys Lys Lys Lys Lys Lys Lys Lys Lys Lys Lys Glu
1               5                   10                  15

Glu Glu Glu Glu
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Lys Lys Lys Lys Lys Glu Glu Glu Glu Glu Glu Glu Glu Glu Glu
1               5                   10                  15

Glu Glu Glu Glu
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Lys Lys Lys Lys Lys Lys Lys Lys Lys Lys Lys Lys Lys Lys Lys
1               5                   10                  15

Glu Glu Glu Glu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Lys Lys Lys Lys Glu Glu Glu Glu Glu Glu Glu Glu Glu Glu Glu
1               5                   10                  15

Glu Glu Glu Glu
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Lys Lys Lys Lys Lys Lys Lys Lys Lys Lys Lys Glu Glu Glu Glu
1               5                   10                  15

Glu Glu Glu Glu
            20

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Lys Lys Glu Lys Lys Glu Lys Lys Glu Lys Lys Glu Lys Lys
1               5                   10

<210> SEQ ID NO 11

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Glu Lys Lys Lys Lys Lys Glu Glu Lys Glu Lys Lys Lys Lys
1               5                   10                  15

<210> SEQ ID NO 12
<211> LENGTH: 22
<212> TYPE: PRT
<213> ORGANISM: Artificial Sequence
<220> FEATURE:
<223> OTHER INFORMATION: Synthetic peptide

<400> SEQUENCE: 12

Lys Lys Lys Lys Lys Lys Lys Lys Lys Lys Lys Lys Lys Lys Lys Lys
1               5                   10                  15

Glu Glu Glu Glu Trp Trp
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic peptide

<400> SEQUENCE: 13

Lys Lys Lys Lys Glu Glu Glu Glu Glu Glu Glu Glu Glu Glu Glu Glu
1               5                   10                  15

Glu Glu Glu Glu Trp Trp
            20

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Glu Glu Glu
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Glu Glu Glu Glu Glu Glu Glu Lys Lys Lys
1               5                   10

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16
```

```
Gly Phe Leu Gly
1

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide

<400> SEQUENCE: 17

Lys Pro Leu Arg
1

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide

<400> SEQUENCE: 18

Lys Leu Arg Pro
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide

<400> SEQUENCE: 19

Ser Leu Val Arg
1

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide

<400> SEQUENCE: 20

Ser Leu Arg Val
1

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Ala Gln Leu Ala Asn Asp Val Val Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Ala Ala Leu Leu Asn Ser Ala Val Leu
```

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Glu Glu Glu Glu Glu Glu Glu Glu Glu Glu Glu Glu Glu Glu Glu
1               5                   10                  15

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Ser Leu Val Arg Lys
1               5

<210> SEQ ID NO 25
<211> LENGTH: 22
<212> TYPE: PRT
<213> ORGANISM: Artificial Sequence
<220> FEATURE:
<223> OTHER INFORMATION: Synthetic peptide

<400> SEQUENCE: 25

Ser Ile Ile Asn Phe Glu Lys Leu Ser Leu Val Arg Glu Glu Glu
1               5                   10                  15

Glu Glu Glu Glu Glu Glu Glu
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic peptide

<400> SEQUENCE: 26

Glu Glu Glu Glu Glu Glu Glu Glu Glu Ser Leu Val Arg Ser Ile
1               5                   10                  15

Ile Asn Phe Glu Lys Leu
            20

<210> SEQ ID NO 27
<211> LENGTH: 31
<212> TYPE: PRT
<213> ORGANISM: Artificial Sequence
<220> FEATURE:
<223> OTHER INFORMATION: Synthetic peptide

<400> SEQUENCE: 27

Ile Ser Gln Ala Val His Ala Ala His Ala Glu Ile Asn Glu Ala Gly
1               5                   10                  15

Arg Glu Val Val Gly Glu Glu Glu Glu Glu Glu Glu Glu Glu Glu
            20                  25                  30

<210> SEQ ID NO 28
<211> LENGTH: 23

```
<212> TYPE: PRT
<213> ORGANISM: Artificial Sequence
<220> FEATURE:
<223> OTHER INFORMATION: Synthetic peptide

<400> SEQUENCE: 28

Ala Ala Leu Leu Asn Ser Ala Val Leu Gly Ala Ala Pro Glu Glu
1               5                   10                  15

Glu Glu Glu Glu Glu Glu Glu
                20

<210> SEQ ID NO 29
<211> LENGTH: 33
<212> TYPE: PRT
<213> ORGANISM: Artificial Sequence
<220> FEATURE:
<223> OTHER INFORMATION: Synthetic peptide

<400> SEQUENCE: 29

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg Glu Glu Glu Glu
            20                  25                  30

Glu

<210> SEQ ID NO 30
<211> LENGTH: 38
<212> TYPE: PRT
<213> ORGANISM: Artificial Sequence
<220> FEATURE:
<223> OTHER INFORMATION: Synthetic peptide

<400> SEQUENCE: 30

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg Glu Glu Glu Glu
            20                  25                  30

Glu Glu Glu Glu Glu Glu
        35

<210> SEQ ID NO 31
<211> LENGTH: 43
<212> TYPE: PRT
<213> ORGANISM: Artificial Sequence
<220> FEATURE:
<223> OTHER INFORMATION: Synthetic peptide

<400> SEQUENCE: 31

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg Glu Glu Glu Glu
            20                  25                  30

Glu Glu Glu Glu Glu Glu Glu Glu Glu Glu Glu
            35                  40

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32
```

```
Arg Arg Arg Arg Arg Arg Arg Arg Arg Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

Lys Ser Phe His Phe Tyr Cys Pro Leu Ser Leu Val Arg Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic peptide

<400> SEQUENCE: 34

Lys Ser Phe His Phe Tyr Cys Pro Leu Ser Leu Val Arg Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic peptide

<400> SEQUENCE: 35

Gln Ile Tyr Ala Phe Leu Gln Gly Phe Ser Leu Val Arg Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic peptide

<400> SEQUENCE: 36

Gln Ile Tyr Ala Phe Leu Gln Gly Phe Ser Leu Val Arg Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic peptide

<400> SEQUENCE: 37

Val Ala Thr Ile Asn Phe Arg Arg Leu Ser Leu Val Arg Lys
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Val Ala Thr Ile Asn Phe Arg Arg Leu Ser Leu Val Arg Lys
```

```
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: Synthetic peptide

<400> SEQUENCE: 39

```
Ala Trp Leu Ser Lys Val Ser Arg Leu Ser Leu Val Arg Lys
1               5                   10
```

<210> SEQ ID NO 40
<211> LENGTH: 14
<212> TYPE: PRT
<213> ORGANISM: Artificial Sequence
<220> FEATURE:
<223> OTHER INFORMATION: Synthetic peptide

<400> SEQUENCE: 40

```
Ala Trp Leu Ser Lys Val Ser Arg Leu Ser Leu Val Arg Lys
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

```
Ile Met Thr Gln His Leu Glu Pro Ile Ser Leu Val Arg Lys
1               5                   10
```

<210> SEQ ID NO 42
<211> LENGTH: 14
<212> TYPE: PRT
<213> ORGANISM: Artificial Sequence
<220> FEATURE:
<223> OTHER INFORMATION: Synthetic peptide

<400> SEQUENCE: 42

```
Ile Met Thr Gln His Leu Glu Pro Ile Ser Leu Val Arg Lys
1               5                   10
```

<210> SEQ ID NO 43
<211> LENGTH: 14
<212> TYPE: PRT
<213> ORGANISM: Artificial Sequence
<220> FEATURE:
<223> OTHER INFORMATION: Synthetic peptide

<400> SEQUENCE: 43

```
Ser Ser Ser Val Leu Phe Glu Tyr Met Ser Leu Val Arg Lys
1               5                   10
```

<210> SEQ ID NO 44
<211> LENGTH: 14
<212> TYPE: PRT
<213> ORGANISM: Artificial Sequence
<220> FEATURE:
<223> OTHER INFORMATION: Synthetic peptide

<400> SEQUENCE: 44

```
Ser Ser Ser Val Leu Phe Glu Tyr Met Ser Leu Val Arg Lys
1               5                   10
```

```
<210> SEQ ID NO 45
<211> LENGTH: 15
<212> TYPE: PRT
<213> ORGANISM: Artificial Sequence
<220> FEATURE:
<223> OTHER INFORMATION: Synthetic peptide

<400> SEQUENCE: 45

Ala Ala Leu Leu Asn Ser Ala Val Leu Gly Ser Leu Val Arg Lys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide

<400> SEQUENCE: 46

Ala Ala Leu Leu Asn Ser Ala Val Leu Gly Ser Leu Val Arg Lys
1               5                   10                  15

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide

<400> SEQUENCE: 47

Ala Ala Leu Leu Asn Ser Ala Val Leu Arg Lys
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide

<400> SEQUENCE: 48

Ala Ala Leu Leu Asn Ser Ala Val Leu Arg Lys
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Synthetic peptide

<400> SEQUENCE: 49

Ala Ser Met Thr Asn Met Glu Leu Met Ser Ser Leu Val Arg Lys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic peptide

<400> SEQUENCE: 50

Ala Ser Met Thr Asn Met Glu Leu Met Ser Ser Leu Val Arg Lys
1               5                   10                  15
```

```
<210> SEQ ID NO 51
<211> LENGTH: 15
<212> TYPE: PRT
<213> ORGANISM: Artificial Sequence
<220> FEATURE:
<223> OTHER INFORMATION: Synthetic peptide

<400> SEQUENCE: 51

Met Ala Pro Ile Asp His Thr Thr Met Ser Ser Leu Val Arg Lys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide

<400> SEQUENCE: 52

Met Ala Pro Ile Asp His Thr Thr Met Ser Ser Leu Val Arg Lys
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Ser Ser Pro Tyr Ser Leu His Tyr Leu Ser Ser Leu Val Arg Lys
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic peptide

<400> SEQUENCE: 54

Ser Ser Pro Tyr Ser Leu His Tyr Leu Ser Ser Leu Val Arg Lys
1               5                   10                  15

<210> SEQ ID NO 55
<211> LENGTH: 18
<212> TYPE: PRT
<213> ORGANISM: Artificial Sequence
<220> FEATURE:
<223> OTHER INFORMATION: Synthetic peptide

<400> SEQUENCE: 55

Ala Lys Phe Val Ala Ala Trp Thr Leu Lys Ala Ala Ser Leu Val
1               5                   10                  15

Arg Lys

<210> SEQ ID NO 56
<211> LENGTH: 18
<212> TYPE: PRT
<213> ORGANISM: Artificial Sequence
<220> FEATURE:
<223> OTHER INFORMATION: Synthetic peptide

<400> SEQUENCE: 56

Ala Lys Phe Val Ala Ala Trp Thr Leu Lys Ala Ala Ser Leu Val
1               5                   10                  15
```

Arg Lys

<210> SEQ ID NO 57
<211> LENGTH: 10
<212> TYPE: PRT
<213> ORGANISM: Artificial Sequence
<220> FEATURE:
<223> OTHER INFORMATION: Synthetic peptide

<400> SEQUENCE: 57

Arg Arg Arg Arg Arg Arg Arg Arg Arg Arg
1               5                   10

<210> SEQ ID NO 58
<211> LENGTH: 31
<212> TYPE: PRT
<213> ORGANISM: Artificial Sequence
<220> FEATURE:
<223> OTHER INFORMATION: Synthetic peptide

<400> SEQUENCE: 58

Ser Ile Ile Asn Phe Glu Lys Leu Val Phe Pro Arg Ser Pro Thr Val
1               5                   10                  15

Phe Tyr Asn Ile Pro Pro Met Pro Leu Pro Pro Ser Gln Leu Lys
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Synthetic peptide

<400> SEQUENCE: 59

Ser Ile Ile Asn Phe Glu Lys Leu Val Lys Pro Arg Ser Pro Thr Arg
1               5                   10                  15

Phe Asp Asn Ser Lys Pro Ser Pro Glu Pro Lys Ser Gln Asp Lys
            20                  25                  30

<210> SEQ ID NO 60
<211> LENGTH: 28
<212> TYPE: PRT
<213> ORGANISM: Artificial Sequence
<220> FEATURE:
<223> OTHER INFORMATION: Synthetic peptide

<400> SEQUENCE: 60

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 61
<211> LENGTH: 26
<212> TYPE: PRT
<213> ORGANISM: Artificial Sequence
<220> FEATURE:
<223> OTHER INFORMATION: Synthetic peptide

<400> SEQUENCE: 61

Lys Ala Arg Asp Glu Thr Ala Gln Leu Ala Asn Asp Val Val Leu Gly
1               5                   10                  15

Ala Ala Pro Leu Phe Val Pro Pro Ala Asp
            20                  25

```
<210> SEQ ID NO 62
<211> LENGTH: 25
<212> TYPE: PRT
<213> ORGANISM: Artificial Sequence
<220> FEATURE:
<223> OTHER INFORMATION: Synthetic peptide

<400> SEQUENCE: 62

Lys Ala Arg Asp Glu Thr Ala Ala Leu Leu Ser Ala Val Leu Gly Ala
1               5                   10                  15

Ala Pro Leu Phe Val Pro Pro Ala Asp
            20                  25

<210> SEQ ID NO 63
<211> LENGTH: 28
<212> TYPE: PRT
<213> ORGANISM: Artificial Sequence
<220> FEATURE:
<223> OTHER INFORMATION: Synthetic peptide

<400> SEQUENCE: 63

Gly Arg Val Leu Glu Leu Phe Arg Ala Ala Ala Leu Leu Asn Ser Ala
1               5                   10                  15

Val Leu Gln Ile Met Glu Leu Cys Gly Ala Thr Arg
            20                  25
```